United States Patent [19]
Borchardt et al.

[11] Patent Number: 5,672,584
[45] Date of Patent: Sep. 30, 1997

[54] CYCLIC PRODRUGS OF PEPTIDES AND PEPTIDE NUCLEIC ACIDS HAVING IMPROVED METABOLIC STABILITY AND CELL MEMBRANE PERMEABILITY

[75] Inventors: Ronald T. Borchardt; Teruna Siahaan; Sanjeev Gangwar; Valentino J. Stella, all of Lawrence, Kans.; Binghe Wang, Norman, Okla.

[73] Assignee: The University of Kansas, Lawrence, Kans.

[21] Appl. No.: 429,732

[22] Filed: Apr. 25, 1995

[51] Int. Cl.$^6$ ................................................ A61K 38/02
[52] U.S. Cl. .................................... 514/11; 530/317
[58] Field of Search ........................... 514/11; 530/317

[56] References Cited

U.S. PATENT DOCUMENTS 4,960,790 10/1990 Stella et al. ............................ 514/449

OTHER PUBLICATIONS

J.M. Balkovec et al., J. Med. Chem. 35:194–98 (1992).
Nutt et al., Klin Wochenschr. 64:71–73 (1986).
Oliyai et al., Annu. Rev. Pharmacol. Toxicol. 32:521–44, 1993.
Amsberry et al., Pharmaceutical Research, vol. 8, No. 4, 455–461 (1991).
Amsberry et al., Pharmaceutical Research, vol. 8, No. 3, 323–330 (1991).
Amsberry et al., J. Organic Chemistry, 55, 5867–5877 (1990).
Egholm, et al., J. Am. Chem. Soc., 114, 1895–1897 (1992).
Miller, Bio/Technology, vol. 9, pp. 358–362 (1991).
Moffat, Science, vol. 253, pp. 510–511 (1991).
Ratner, Bio/Technology, vol. 9, pp. 410–411 (1991).
Neckers, Oligodeoxynucleotides Antisense Inhibitors of Gene Expression, Edited by Jack S. Cohen, pp. 211–231 (1989).
Cohen, Antiviral Research, 16, pp. 121–133 (1991).
Nielsen et al., Science, 254, pp. 1497–1500 (1991).
Tidd, D.M., "Synthetic oligonucleotides as therapeutic agents", 25 Jul. 1990, pp. 6–8.

Primary Examiner—Jerry D. Johnson
Attorney, Agent, or Firm—Birch, Stewart, Kolasch, Birch, LLP

[57] ABSTRACT

Provided are cyclic prodrugs of biologically active peptides and peptide nucleic acids exhibiting improved cell membrane permeability and enzymatic stability, containing 3-(2'-hydroxy-4',6'-dimethyl phenyl)-3,3-dimethyl propionic acid and its deriveatives and acyloxyalkoxy linkers. Also provided are pharmaceutical compositions containing effective amounts of these cyclic prodrugs in combination with pharmaceutically acceptable carriers, excipients, or diluents.

5 Claims, 1 Drawing Sheet

SEQUENCE LISTING ( 1 ) GENERAL INFORMATION:

( i i i ) NUMBER OF SEQUENCES: 40

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

Trp Ala Gly Gly Asp Ala
    1                5

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( C ) STRANDEDNESS: single (D) TOPOLOGY: linear (i i) MOLECULE TYPE: peptide (i i i) HYPOTHETICAL: NO (i v) ANTI-SENSE: NO (i x) FEATURE:
    (A) NAME/KEY: Modified-site
    (B) LOCATION: 1
    (D) OTHER INFORMATION: /product="OTHER"
        / label= Boc
        / note= "Boc modification"

(i x) FEATURE:
    (A) NAME/KEY: Modified-site
    (B) LOCATION: 4
    (D) OTHER INFORMATION: /product="OTHER"
        / label= OBzl-OTce (x i) SEQUENCE DESCRIPTION: SEQ ID NO:2:

Ala  Gly  Gly  Asp
1

(2) INFORMATION FOR SEQ ID NO:3:

(i) SEQUENCE CHARACTERISTICS:
        (A) LENGTH: 4 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (i x) FEATURE:
        (A) NAME/KEY: Modified-site
        (B) LOCATION: 4
        (D) OTHER INFORMATION: /product="OTHER"
            / label= OBzl-OTce (x i) SEQUENCE DESCRIPTION: SEQ ID NO:3:

Ala  Gly  Gly  Asp
1

(2) INFORMATION FOR SEQ ID NO:4:

(i) SEQUENCE CHARACTERISTICS:
        (A) LENGTH: 6 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (i x) FEATURE:
        (A) NAME/KEY: Modified-site
        (B) LOCATION: 1
        (D) OTHER INFORMATION: /product="OTHER"
            / label= Boc (i x) FEATURE:
        (A) NAME/KEY: Modified-site
        (B) LOCATION: 2
        (D) OTHER INFORMATION: /product="OTHER"
            / label= OCH2COC
            / note= "links C-terminus of Ala to N-terminus of Trp"

( i x ) FEATURE:
  ( A ) NAME/KEY: Modified-site
  ( B ) LOCATION: 6
  ( D ) OTHER INFORMATION: /product="OTHER"
        / label= OBzl-OTce ( x i ) SEQUENCE DESCRIPTION: SEQ ID NO:4:

Ala Trp Ala Gly Gly Asp
1               5

( 2 ) INFORMATION FOR SEQ ID NO:5:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( i x ) FEATURE:
    ( A ) NAME/KEY: Modified-site
    ( B ) LOCATION: 1
    ( D ) OTHER INFORMATION: /product="OTHER"
          / label= Boc ( i x ) FEATURE:
    ( A ) NAME/KEY: Modified-site
    ( B ) LOCATION: 2
    ( D ) OTHER INFORMATION: /product="OTHER"
          / label= OCH2OCO
          / note= "links C-terminus of Ala with N-terminus of Trp"

( i x ) FEATURE:
    ( A ) NAME/KEY: Modified-site
    ( B ) LOCATION: 6
    ( D ) OTHER INFORMATION: /product="OTHER"
          / label= OBzl-OH ( x i ) SEQUENCE DESCRIPTION: SEQ ID NO:5:

Ala Trp Ala Gly Gly Asp
1               5

( 2 ) INFORMATION FOR SEQ ID NO:6:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( i x ) FEATURE:
    ( A ) NAME/KEY: Modified-site
    ( B ) LOCATION: 2
    ( D ) OTHER INFORMATION: /product="other"
          / label= OCH2OCO
          / note= "links C-terminus of Ala to N-terminus of Trp"

( i x ) FEATURE:
    ( A ) NAME/KEY: Modified-site
    ( B ) LOCATION: 6
    ( D ) OTHER INFORMATION: /product="other"
          / label= OBzl-OH ( x i ) SEQUENCE DESCRIPTION: SEQ ID NO:6:

```
Ala Trp Ala Gly Gly Asp
1               5
```

(2) INFORMATION FOR SEQ ID NO:7:

(i) SEQUENCE CHARACTERISTICS:
        (A) LENGTH: 6 amino acids
        (B) TYPE: amino acid
        (C) STRANDEDNESS: single
        (D) TOPOLOGY: circular (ii) MOLECULE TYPE: peptide (iii) HYPOTHETICAL: NO (ix) FEATURE:
        (A) NAME/KEY: Modified-site
        (B) LOCATION: 1
        (D) OTHER INFORMATION: /product="other"
            / note= "peptide cyclized between the N-terminal group
            of Trp and the C-terminus of Ala"

(ix) FEATURE:
        (A) NAME/KEY: Modified-site
        (B) LOCATION: 5
        (D) OTHER INFORMATION: /product="other"
            / label= OBzl (xi) SEQUENCE DESCRIPTION: SEQ ID NO:7:

```
Trp Ala Gly Gly Asp Ala
1               5
```

(2) INFORMATION FOR SEQ ID NO:8:

(i) SEQUENCE CHARACTERISTICS:
        (A) LENGTH: 6 amino acids
        (B) TYPE: amino acid
        (C) STRANDEDNESS: single
        (D) TOPOLOGY: circular (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 1
        (D) OTHER INFORMATION: /product="other"
            / note= "peptide cyclized between the N-terminus of
            Trp and the C- terminus of Ala"

(xi) SEQUENCE DESCRIPTION: SEQ ID NO:8:

```
Trp Ala Gly Gly Asp Ala
1               5
```

(2) INFORMATION FOR SEQ ID NO:9:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 1
        (D) OTHER INFORMATION: /product="other"

/ label= Boc (ix) FEATURE:
  (A) NAME/KEY: Modified-site
  (B) LOCATION: 4
  (D) OTHER INFORMATION: /product="other"
       / label= OBzl-OTce (xi) SEQUENCE DESCRIPTION: SEQ ID NO:9:

Trp Ala Gly Gly Asp
1               5

(2) INFORMATION FOR SEQ ID NO:10:

(i) SEQUENCE CHARACTERISTICS:
    (A) LENGTH: 5 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (ix) FEATURE:
    (A) NAME/KEY: Modified-site
    (B) LOCATION: 4
    (D) OTHER INFORMATION: /product="other"
         / label= OBzl-OTce (xi) SEQUENCE DESCRIPTION: SEQ ID NO:10:

Trp Ala Gly Gly Asp
1               5

(2) INFORMATION FOR SEQ ID NO:11:

(i) SEQUENCE CHARACTERISTICS:
    (A) LENGTH: 5 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (ix) FEATURE:
    (A) NAME/KEY: Modified-site
    (B) LOCATION: 4
    (D) OTHER INFORMATION: /product="other"
         / label= OBzl-O-CH2-CCl3

(xi) SEQUENCE DESCRIPTION: SEQ ID NO:11:

Trp Ala Gly Gly Asp
1               5

(2) INFORMATION FOR SEQ ID NO:12:

(i) SEQUENCE CHARACTERISTICS:
    (A) LENGTH: 6 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO ( i x ) FEATURE:
    ( A ) NAME/KEY: Modified-site
    ( B ) LOCATION: 1
    ( D ) OTHER INFORMATION: /product="other"
        / note= "Ala modified with ring group joined with
        N-terminus of Trp"

( i x ) FEATURE:
    ( A ) NAME/KEY: Modified-site
    ( B ) LOCATION: 6
    ( D ) OTHER INFORMATION: /product="other"
        / label= OBzl-O-CH2-CCl3

( i x ) FEATURE:
    ( A ) NAME/KEY: Modified-site
    ( B ) LOCATION: 1
    ( D ) OTHER INFORMATION: /product="other"
        / label= Boc ( x i ) SEQUENCE DESCRIPTION: SEQ ID NO:12:

Ala Trp Ala Gly Gly Asp
1              5

( 2 ) INFORMATION FOR SEQ ID NO:13:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( i x ) FEATURE:
    ( A ) NAME/KEY: Modified-site
    ( B ) LOCATION: 1
    ( D ) OTHER INFORMATION: /product="other"
        / note= "Ring group joining the C-terminus of Ala and the
        N-terminus of Trp"

( i x ) FEATURE:
    ( A ) NAME/KEY: Modified-site
    ( B ) LOCATION: 6
    ( D ) OTHER INFORMATION: /product="modified"
        / label= OBzl-O ( x i ) SEQUENCE DESCRIPTION: SEQ ID NO:13:

Ala Trp Ala Gly Gly Asp
1              5

( 2 ) INFORMATION FOR SEQ ID NO:14:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( i x ) FEATURE:
    ( A ) NAME/KEY: Modified-site
    ( B ) LOCATION: 1
    ( D ) OTHER INFORMATION: /product="other"
        / label= Boc ( i x ) FEATURE:
    ( A ) NAME/KEY: Modified-site ( B ) LOCATION: 1
( D ) OTHER INFORMATION: /product="other"
/ label= Prom ( i x ) FEATURE:
( A ) NAME/KEY: Modified-site
( B ) LOCATION: 6
( D ) OTHER INFORMATION: /product="other"
/ label= OBzl-OTce ( x i ) SEQUENCE DESCRIPTION: SEQ ID NO:14:

Ala Trp Ala Gly Gly Asp
1              5

( 2 ) INFORMATION FOR SEQ ID NO:15:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( i x ) FEATURE:
( A ) NAME/KEY: Modified-site
( B ) LOCATION: 1
( D ) OTHER INFORMATION: /product="other"
/ label= Boc ( i x ) FEATURE:
( A ) NAME/KEY: Modified-site
( B ) LOCATION: 1
( D ) OTHER INFORMATION: /product="Other"
/ label= Prom ( i x ) FEATURE:
( A ) NAME/KEY: Modified-site
( B ) LOCATION: 6
( D ) OTHER INFORMATION: /product="other"
/ label= OBzl-OH ( x i ) SEQUENCE DESCRIPTION: SEQ ID NO:15:

Ala Trp Ala Gly Gly Asp
1              5

( 2 ) INFORMATION FOR SEQ ID NO:16:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i x ) FEATURE:
( A ) NAME/KEY: Modified-site
( B ) LOCATION: 1
( D ) OTHER INFORMATION: /product="other"
/ label= Prom ( i x ) FEATURE:
( A ) NAME/KEY: Modified-site
( B ) LOCATION: 6
( D ) OTHER INFORMATION: /product="other"
/ label= OBzl-OH ( x i ) SEQUENCE DESCRIPTION: SEQ ID NO:16:

```
    Ala  Trp  Ala  Gly  Gly  Asp
    1                   5
```

( 2 ) INFORMATION FOR SEQ ID NO:17:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:17:

```
    Tyr  Gly  Gly  Phe  Leu
    1                   5
```

( 2 ) INFORMATION FOR SEQ ID NO:18:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 2
        ( D ) OTHER INFORMATION: /product="other"
            / label= D-Ala ( i x ) FEATURE:
        ( A ) NAME/KEY: Modified-site
        ( B ) LOCATION: 5
        ( D ) OTHER INFORMATION: /product="other"
            / label= D-Leu ( x i ) SEQUENCE DESCRIPTION: SEQ ID NO:18:

```
    Tyr  Ala  Gly  Phe  Leu
    1                   5
```

( 2 ) INFORMATION FOR SEQ ID NO:19:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 2
        ( D ) OTHER INFORMATION: /product="other"
            / label= D-Ser ( i x ) FEATURE:
        ( A ) NAME/KEY: Modified-site
        ( B ) LOCATION: 2
        ( D ) OTHER INFORMATION: /product="other"

/ label= OtBu ( i x ) FEATURE:
    ( A ) NAME/KEY: Modified-site
    ( B ) LOCATION: 6
    ( D ) OTHER INFORMATION: /product="other"
        / label= OtBu-OH ( x i ) SEQUENCE DESCRIPTION: SEQ ID NO:19:

Tyr Ser Gly Phe Leu Thr
1                   5

( 2 ) INFORMATION FOR SEQ ID NO:20:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 2
        ( D ) OTHER INFORMATION: /product="other"
          / label= D-Arg ( x i ) SEQUENCE DESCRIPTION: SEQ ID NO:20:

Tyr Arg Phe Gly
1

( 2 ) INFORMATION FOR SEQ ID NO:21:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 2
        ( D ) OTHER INFORMATION: /product="other"
          / label= D-Met ( x i ) SEQUENCE DESCRIPTION: SEQ ID NO:21:

Tyr Met Phe His Leu Met Asp
1                   5

( 2 ) INFORMATION FOR SEQ ID NO:22:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO -continued (ix) FEATURE:
                (A) NAME/KEY: Modified-site
                (B) LOCATION: 2
                (D) OTHER INFORMATION: /product="other"
                    / label= D-Ala (xi) SEQUENCE DESCRIPTION: SEQ ID NO:22:

Tyr  Ala  Phe  Asp  Val  Val  Gly
     1                   5

(2) INFORMATION FOR SEQ ID NO:23:

(i) SEQUENCE CHARACTERISTICS:
                (A) LENGTH: 7 amino acids
                (B) TYPE: amino acid
                (C) STRANDEDNESS: single
                (D) TOPOLOGY: linear (ii) MOLECULE TYPE: peptide (iii) HYPOTHETICAL: NO (iv) ANTI-SENSE: NO (ix) FEATURE:
                (A) NAME/KEY: Modified-site
                (B) LOCATION: 2
                (D) OTHER INFORMATION: /product="other"
                    / label= D-Ala (xi) SEQUENCE DESCRIPTION: SEQ ID NO:23:

Tyr  Ala  Phe  Glu  Val  Val  Gly
     1                   5

(2) INFORMATION FOR SEQ ID NO:24:

(i) SEQUENCE CHARACTERISTICS:
                (A) LENGTH: 5 amino acids
                (B) TYPE: amino acid
                (C) STRANDEDNESS: single
                (D) TOPOLOGY: linear (ii) MOLECULE TYPE: peptide (iii) HYPOTHETICAL: NO (iv) ANTI-SENSE: NO (ix) FEATURE:
                (A) NAME/KEY: Modified-site
                (B) LOCATION: 1
                (D) OTHER INFORMATION: /product="other"
                    / label= Fmoc (ix) FEATURE:
                (A) NAME/KEY: Modified-site
                (B) LOCATION: 1
                (D) OTHER INFORMATION: /product="other"
                    / label= OP (ix) FEATURE:
                (A) NAME/KEY: Modified-site
                (B) LOCATION: 2
                (D) OTHER INFORMATION: /product="other"
                    / label= D-Ser (ix) FEATURE:
                (A) NAME/KEY: Modified-site
                (B) LOCATION: 2
                (D) OTHER INFORMATION: /product="other"
                    / label= OtBu (ix) FEATURE:
                (A) NAME/KEY: Modified-site
                (B) LOCATION: 5
                (D) OTHER INFORMATION: /product="other"

/ label= OBzl ( x i ) SEQUENCE DESCRIPTION: SEQ ID NO:24:

Tyr Ser Gly Phe Leu
1                 5

( 2 ) INFORMATION FOR SEQ ID NO:25:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( i x ) FEATURE:
( A ) NAME/KEY: Modified-site
( B ) LOCATION: 1
( D ) OTHER INFORMATION: /product="other"
/ label= CBZ ( i x ) FEATURE:
( A ) NAME/KEY: Modified-site
( B ) LOCATION: 1
( D ) OTHER INFORMATION: /product="other"
/ label= OtBu ( i x ) FEATURE:
( A ) NAME/KEY: Modified-site
( B ) LOCATION: 1
( D ) OTHER INFORMATION: /product="other"
/ label= Prom ( i x ) FEATURE:
( A ) NAME/KEY: Modified-site
( B ) LOCATION: 2
( D ) OTHER INFORMATION: /product="other"
/ label= OP ( i x ) FEATURE:
( A ) NAME/KEY: Modified-site
( B ) LOCATION: 3
( D ) OTHER INFORMATION: /product="other"
/ label= D-Ser ( i x ) FEATURE:
( A ) NAME/KEY: Modified-site
( B ) LOCATION: 3
( D ) OTHER INFORMATION: /product="other"
/ label= OtBu ( i x ) FEATURE:
( A ) NAME/KEY: Modified-site
( B ) LOCATION: 6
( D ) OTHER INFORMATION: /product="other"
/ label= OBzl ( x i ) SEQUENCE DESCRIPTION: SEQ ID NO:25:

Thr Tyr Ser Gly Phe Leu
1                     5

( 2 ) INFORMATION FOR SEQ ID NO:26:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide (  i i i  ) HYPOTHETICAL: NO (  i v  ) ANTI-SENSE: NO (  i x  ) FEATURE:
    ( A ) NAME/KEY: Modified-site
    ( B ) LOCATION: 1
    ( D ) OTHER INFORMATION: /product="other"
        / label= OtBu (  i x  ) FEATURE:
    ( A ) NAME/KEY: Modified-site
    ( B ) LOCATION: 1
    ( D ) OTHER INFORMATION: /product="other"
        / label= Prom (  i x  ) FEATURE:
    ( A ) NAME/KEY: Modified-site
    ( B ) LOCATION: 2
    ( D ) OTHER INFORMATION: /product="other"
        / label= OP (  i x  ) FEATURE:
    ( A ) NAME/KEY: Modified-site
    ( B ) LOCATION: 3
    ( D ) OTHER INFORMATION: /product="other"
        / label= D-Ser (  i x  ) FEATURE:
    ( A ) NAME/KEY: Modified-site
    ( B ) LOCATION: 3
    ( D ) OTHER INFORMATION: /product="other"
        / label= OtBu (  x i  ) SEQUENCE DESCRIPTION: SEQ ID NO:26:

Thr  Tyr  Ser  Gly  Phe  Leu
1                        5

( 2 ) INFORMATION FOR SEQ ID NO:27:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 1
        ( D ) OTHER INFORMATION: /product="other"
            / label= OtBu ( i x ) FEATURE:
        ( A ) NAME/KEY: Modified-site
        ( B ) LOCATION: 1
        ( D ) OTHER INFORMATION: /product="other"
            / label= Prom ( i x ) FEATURE:
        ( A ) NAME/KEY: Modified-site
        ( B ) LOCATION: 3
        ( D ) OTHER INFORMATION: /product="other"
            / label= D-Ser ( i x ) FEATURE:
        ( A ) NAME/KEY: Modified-site
        ( B ) LOCATION: 3
        ( D ) OTHER INFORMATION: /product="other"
            / label= OtBu ( x i ) SEQUENCE DESCRIPTION: SEQ ID NO:27:

Thr Tyr Ser Gly Phe Leu
1               5

( 2 ) INFORMATION FOR SEQ ID NO:28:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 1
        ( D ) OTHER INFORMATION: /product="other"
            / label= CBZ ( i x ) FEATURE:
        ( A ) NAME/KEY: Modified-site
        ( B ) LOCATION: 1
        ( D ) OTHER INFORMATION: /product="other"
            / label= OtBu-Prom-O-

( i x ) FEATURE:
        ( A ) NAME/KEY: Modified-site
        ( B ) LOCATION: 2
        ( D ) OTHER INFORMATION: /product="other"
            / label= Fmoc ( i x ) FEATURE:
        ( A ) NAME/KEY: Modified-site
        ( B ) LOCATION: 3
        ( D ) OTHER INFORMATION: /product="other"
            / label= D-Ser ( i x ) FEATURE:
        ( A ) NAME/KEY: Modified-site
        ( B ) LOCATION: 3
        ( D ) OTHER INFORMATION: /product="other"
            / label= OtBu ( i x ) FEATURE:
        ( A ) NAME/KEY: Modified-site
        ( B ) LOCATION: 6
        ( D ) OTHER INFORMATION: /product="other"
            / label= OBzl ( x i ) SEQUENCE DESCRIPTION: SEQ ID NO:28:

Thr Tyr Ser Gly Phe Leu
1               5

( 2 ) INFORMATION FOR SEQ ID NO:29:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 1
        ( D ) OTHER INFORMATION: /product="other"
            / label= OtBu-Prom-O-

( i x ) FEATURE:
  ( A ) NAME/KEY: Modified-site
  ( B ) LOCATION: 2
  ( D ) OTHER INFORMATION: /product="other"
    / label= Fmoc ( i x ) FEATURE:
  ( A ) NAME/KEY: Modified-site
  ( B ) LOCATION: 3
  ( D ) OTHER INFORMATION: /product="other"
    / label= D-Ser ( i x ) FEATURE:
  ( A ) NAME/KEY: Modified-site
  ( B ) LOCATION: 3
  ( D ) OTHER INFORMATION: /product="other"
    / label= OtBu ( x i ) SEQUENCE DESCRIPTION: SEQ ID NO:29:

Thr Tyr Ser Gly Phe Leu
1               5

( 2 ) INFORMATION FOR SEQ ID NO:30:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( i x ) FEATURE:
    ( A ) NAME/KEY: Modified-site
    ( B ) LOCATION: 1
    ( D ) OTHER INFORMATION: /product="other"
      / label= OtBu-Prom-O-NH2

( i x ) FEATURE:
    ( A ) NAME/KEY: Modified-site
    ( B ) LOCATION: 3
    ( D ) OTHER INFORMATION: /product="other"
      / label= D-Ser ( i x ) FEATURE:
    ( A ) NAME/KEY: Modified-site
    ( B ) LOCATION: 3
    ( D ) OTHER INFORMATION: /product="other"
      / label= OtBu ( x i ) SEQUENCE DESCRIPTION: SEQ ID NO:30:

Thr Tyr Ser Gly Phe Leu
1               5

( 2 ) INFORMATION FOR SEQ ID NO:31:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( i x ) FEATURE:
    ( A ) NAME/KEY: Modified-site
    ( B ) LOCATION: 1
    ( D ) OTHER INFORMATION: /product="other"

/ label= Fmoc ( i x ) FEATURE:
    ( A ) NAME/KEY: Modified-site
    ( B ) LOCATION: 1
    ( D ) OTHER INFORMATION: /product="other"
        / label= OtBu ( i x ) FEATURE:
    ( A ) NAME/KEY: Modified-site
    ( B ) LOCATION: 2
    ( D ) OTHER INFORMATION: /product="other"
        / label= D-Met ( i x ) FEATURE:
    ( A ) NAME/KEY: Modified-site
    ( B ) LOCATION: 4
    ( D ) OTHER INFORMATION: /product="other"
        / label= Boc ( i x ) FEATURE:
    ( A ) NAME/KEY: Modified-site
    ( B ) LOCATION: 6
    ( D ) OTHER INFORMATION: /product="other"
        / label= OBzl ( x i ) SEQUENCE DESCRIPTION: SEQ ID NO:31:

Tyr  Met  Phe  His  Leu  Met
1                          5

( 2 ) INFORMATION FOR SEQ ID NO:32:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 1
        ( D ) OTHER INFORMATION: /product="other"
            / label= CBZ ( i x ) FEATURE:
        ( A ) NAME/KEY: Modified-site
        ( B ) LOCATION: 1
        ( D ) OTHER INFORMATION: /product="other"
            / label= Prom ( i x ) FEATURE:
        ( A ) NAME/KEY: Modified-site
        ( B ) LOCATION: 2
        ( D ) OTHER INFORMATION: /product="other"
            / label= OtBu ( i x ) FEATURE:
        ( A ) NAME/KEY: Modified-site
        ( B ) LOCATION: 3
        ( D ) OTHER INFORMATION: /product="other"
            / label= D-Met ( i x ) FEATURE:
        ( A ) NAME/KEY: Modified-site
        ( B ) LOCATION: 5
        ( D ) OTHER INFORMATION: /product="other"
            / label= Boc ( i x ) FEATURE:
        ( A ) NAME/KEY: Modified-site
        ( B ) LOCATION: 7
        ( D ) OTHER INFORMATION: /product="other"

/ label= OBzl ( x i ) SEQUENCE DESCRIPTION: SEQ ID NO:32:

Asp Tyr Met Phe His Leu Met
1                   5

( 2 ) INFORMATION FOR SEQ ID NO:33:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 1
        ( D ) OTHER INFORMATION: /product="other"
            / label= Prom ( i x ) FEATURE:
        ( A ) NAME/KEY: Modified-site
        ( B ) LOCATION: 2
        ( D ) OTHER INFORMATION: /product="other"
            / label= OtBu ( i x ) FEATURE:
        ( A ) NAME/KEY: Modified-site
        ( B ) LOCATION: 3
        ( D ) OTHER INFORMATION: /product="other"
            / label= D-Met ( i x ) FEATURE:
        ( A ) NAME/KEY: Modified-site
        ( B ) LOCATION: 5
        ( D ) OTHER INFORMATION: /product="other"
            / label= Boc ( x i ) SEQUENCE DESCRIPTION: SEQ ID NO:33:

Asp Tyr Met Phe His Leu Met
1                   5

( 2 ) INFORMATION FOR SEQ ID NO:34:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 1
        ( D ) OTHER INFORMATION: /product="other"
            / label= Prom ( i x ) FEATURE:
        ( A ) NAME/KEY: Modified-site
        ( B ) LOCATION: 3
        ( D ) OTHER INFORMATION: /product="other"
            / label= D-Met ( x i ) SEQUENCE DESCRIPTION: SEQ ID NO:34:

```
Asp  Tyr  Met  Phe  His  Leu  Met
 1                 5
```

( 2 ) INFORMATION FOR SEQ ID NO:35:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 1
        ( D ) OTHER INFORMATION: /product="other"
            / label= Fmoc ( i x ) FEATURE:
        ( A ) NAME/KEY: Modified-site
        ( B ) LOCATION: 2
        ( D ) OTHER INFORMATION: /product="other"
            / label= D-Met ( i x ) FEATURE:
        ( A ) NAME/KEY: Modified-site
        ( B ) LOCATION: 4
        ( D ) OTHER INFORMATION: /product="other"
            / label= Boc ( i x ) FEATURE:
        ( A ) NAME/KEY: Modified-site
        ( B ) LOCATION: 6
        ( D ) OTHER INFORMATION: /product="other"
            / label= OBzl ( x i ) SEQUENCE DESCRIPTION: SEQ ID NO:35:

```
Tyr  Met  Phe  His  Leu  Met
 1                 5
```

( 2 ) INFORMATION FOR SEQ ID NO:36:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 1
        ( D ) OTHER INFORMATION: /product="other"
            / label= CBZ ( i x ) FEATURE:
        ( A ) NAME/KEY: Modified-site
        ( B ) LOCATION: 1
        ( D ) OTHER INFORMATION: /product="other"
            / label= Prom-O-

( i x ) FEATURE:
        ( A ) NAME/KEY: Modified-site
        ( B ) LOCATION: 2
        ( D ) OTHER INFORMATION: /product="other"
            / label= Fmoc (ix) FEATURE:
    (A) NAME/KEY: Modified-site
    (B) LOCATION: 3
    (D) OTHER INFORMATION: /product="other"
        / label= D-Met (ix) FEATURE:
    (A) NAME/KEY: Modified-site
    (B) LOCATION: 5
    (D) OTHER INFORMATION: /product="other"
        / label= Boc (ix) FEATURE:
    (A) NAME/KEY: Modified-site
    (B) LOCATION: 7
    (D) OTHER INFORMATION: /product="other"
        / label= OBzl (xi) SEQUENCE DESCRIPTION: SEQ ID NO:36:

Asp Tyr Met Phe His Leu Met
1               5

(2) INFORMATION FOR SEQ ID NO:37:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 1
        (D) OTHER INFORMATION: /product="other"
            / label= Prom-O-

(ix) FEATURE:
        (A) NAME/KEY: Modified-site
        (B) LOCATION: 2
        (D) OTHER INFORMATION: /product="other"
            / label= Fmoc (ix) FEATURE:
        (A) NAME/KEY: Modified-site
        (B) LOCATION: 3
        (D) OTHER INFORMATION: /product="other"
            / label= D-Met (ix) FEATURE:
        (A) NAME/KEY: Modified-site
        (B) LOCATION: 5
        (D) OTHER INFORMATION: /product="other"
            / label= Boc (xi) SEQUENCE DESCRIPTION: SEQ ID NO:37:

Asp Tyr Met Phe His Leu Met
1               5

(2) INFORMATION FOR SEQ ID NO:38:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (ix) FEATURE:
   (A) NAME/KEY: Modified-site
   (B) LOCATION: 1
   (D) OTHER INFORMATION: /product="other"
       / label= Prom-O-

(ix) FEATURE:
   (A) NAME/KEY: Modified-site
   (B) LOCATION: 3
   (D) OTHER INFORMATION: /product="other"
       / label= D-Met (xi) SEQUENCE DESCRIPTION: SEQ ID NO:38:

Asp Tyr Met Phe His Leu Met
1               5

(2) INFORMATION FOR SEQ ID NO:39:

(i) SEQUENCE CHARACTERISTICS:
       (A) LENGTH: 4 amino acids
       (B) TYPE: amino acid
       (C) STRANDEDNESS: single
       (D) TOPOLOGY: linear (ii) MOLECULE TYPE: peptide (iii) HYPOTHETICAL: NO (iv) ANTI-SENSE: NO (ix) FEATURE:
       (A) NAME/KEY: Modified-site
       (B) LOCATION: 2
       (D) OTHER INFORMATION: /product="other"
           / label= Tic
           / note= "amino acid is Tic(psi)[CH2NH]"

(xi) SEQUENCE DESCRIPTION: SEQ ID NO:39:

Tyr Xaa Phe Phe
1

(2) INFORMATION FOR SEQ ID NO:40:

(i) SEQUENCE CHARACTERISTICS:
       (A) LENGTH: 6 amino acids
       (B) TYPE: amino acid
       (C) STRANDEDNESS: single
       (D) TOPOLOGY: linear (ii) MOLECULE TYPE: peptide (iii) HYPOTHETICAL: NO (iv) ANTI-SENSE: NO (ix) FEATURE:
       (A) NAME/KEY: Modified-site
       (B) LOCATION: 1
       (D) OTHER INFORMATION: /product="other"
           / label= Ac (xi) SEQUENCE DESCRIPTION: SEQ ID NO:40:

Trp Ala Gly Gly Asp Ala
1               5

CYCLIC PRODRUGS OF PEPTIDES AND PEPTIDE NUCLEIC ACIDS HAVING IMPROVED METABOLIC STABILITY AND CELL MEMBRANE PERMEABILITY

BACKGROUND OF THE INVENTION

1. Field of the Invention

The present invention relates to the use of various linkers to produce esterase-sensitive, cyclic prodrugs of peptides and peptide nucleic acids (pNAs) in order to improve the metabolic stability and cell membrane permeability thereof, the prodrugs per se, and pharmaceutical compositions containing the same.

This unique methodology is applicable to the production of cyclic prodrugs of peptides and pNAs, and provides a general method for enhancing the metabolic stability and the membrane permeability of these classes of molecules while retaining or enhancing the pharmaceutical activity of the parent peptides or peptide nucleic acids, thus facilitating their clinical use.

2. Description of Related Art

Through rational drug design, medicinal chemists have synthesized many peptides (Plattner et al., 1990; Morgan et al., 1989; Greenlee, 1990; Huff, 1991; and Doherty, 1992) and pNAs (Hanvey et al., 1992) with novel therapeutic potential. However, because of their metabolic lability (particularly peptides) and low permeability through biological barriers such as the intestinal mucosa, oral dosage forms of peptides and pNAs have been difficult to develop as therapeutic agents (Humphrey et al., 1986; Lee et al., 1990; and Lee, 1991). Even when peptides and pNAs are administered via parenteral route (e.g., intravenously), they tend not to gain access to important target areas (e.g., the brain) (Audus et al., 1992; Taubes, 1993).

The problem of metabolic lability has for all practical purposes been resolved by medicinal chemists through structural manipulation of the peptide or pNA to remove enzyme-sensitive bonds. However, medicinal chemists have had less success in manipulating the structures of peptides or pNAs so as to achieve high cell membrane permeability while still retaining pharmacological activity. Unfortunately, many of the structural features of peptides and pNAs (e.g., free N-terminal amino and C-terminal carboxyl groups for peptides and pNAs and side chain carboxyl (e.g., Asp, Glu), amino (e.g., Lys, Arg) and hydroxyl (e.g. Ser, Thr, Tyr) groups for peptides) that bestow upon the molecule affinity and specificity for its pharmacological receptor also bestow upon the molecule undesirable physicochemical properties (e.g., charge, hydrogen bonding potential) which limit their cell membrane permeability (Burton et al., 1991). Therefore, alternative strategies need to be considered if orally bioavailable and/or blood brain barrier (BBB) peptides and pNAs are to be discovered.

One possible strategy that has been extensively exploited for small organic molecules is that of prodrugs (Bundgaard, 1985). By transiently (i.e., bioreversibly) derivatizing carboxyl, hydroxyl, and amino groups in small organic molecules, the undesirable physicochemical characteristics (e.g., charge, hydrogen bonding potential, etc.) of these molecules have been "masked" without permanently altering the pharmacological properties of the molecule.

Bioreversible prodrug derivatives of drugs have been shown to improve the physicochemical (e.g., solubility, lipophilicity) properties of many drugs, particularly those that contain hydroxyl and carboxylic acid groups (Bundgaard, 1985). However, prodrugs of amine-containing compounds have been more difficult to prepare. One possible approach to making prodrugs of amine-containing drugs is through the acylation of the amino group. However, simple amides are generally too stable in vivo to be useful prodrugs of amines (Bundgaard, 1985).

Recently, Oliyai et al. (1993) reviewed the ways in which prodrug methodology has been employed to alter the metabolic lability and the physicochemical properties of peptides. Unfortunately, the use of prodrugs in the field of peptide research has been very limited. A possible reason for this limited use of prodrugs to modify the properties of peptides and pNAs may be their structural complexity and the lack of novel methodology.

The use of acyloxyalkoxycarbamate derivatives of amines as prodrugs has been discussed previously in the literature by Gogate et al. (1987) and Alexander et al. (1988).

3-(2'-hydroxy-4',6'-dimethylphenyl)-3,3-dimethylpropionic acid has been employed to prepare linear, esterase- (Amsberry et al., 1991), phosphatase-(Nicolaou and Borchardt, unpublished data), and dehydrogenase- (Amsberry et al., 1991; Wolfe et al., 1992) sensitive prodrugs of amines. These systems have been shown to degrade through a two step mechanism, with the first step being the slow, rate-determining enzyme-catalyzed (esterase, phosphatase, or dehydrogenase) step, and the second step being a rapid ($t_{1/2}$=100 sec., pH 7.4, 37° C.) chemical step (Amsberry et al., 1990). Interestingly, the phosphatase-sensitive system has recently been employed to prepare a very water-soluble (greater than 10 mg/ml) prodrug of TAXOL which shows significant antitumor activity in vivo.

As far as the present inventors are aware, there has been no discussion in the literature of the concept of employing the linkers described infra to convert linear peptides and pNAs to esterase-sensitive, cyclic prodrugs.

SUMMARY OF THE INVENTION

Accordingly, it is an object of the present invention to provide a cyclic prodrug of a biologically active peptide or PNA. In these cyclic prodrugs, the N-terminal amino group and the C-terminal carboxyl group of said biologically active peptide or PNA is linked via a linker, or the C-terminal carboxyl group of said peptide is linked to a side chain amino group or a side chain hydroxyl group via a linker, or the N-terminal amino group of said peptide is linked to a side chain carboxyl group via a linker, or a side chain carboxyl group of said peptide is linked to a side chain amino group or a side chain hydroxyl group via a linker. Useful linkers include 3-(2'-hydroxy-4',6'-dimethyl phenyl) -3,3-dimethyl propionic acid linkers and its derivatives (compound formulas I–IX) and acyloxyalkoxy derivatives (compound formulas X–XII) linkers (see Scheme 4).

It is another object of the present invention to provide pharmaceutical compositions containing an effective amount of cyclic prodrugs of peptides and PNA, and a pharmaceutically acceptable, carrier, diluent, or excipient.

BRIEF DESCRIPTION OF THE DRAWING

The above and other objects, features, and advantages of the present invention will be better understood from the following detailed descriptions taken in conjunction with the accompanying drawing, all of which are given by way of illustration only, and which are not limitative of the present invention, in which.

Figure 1:
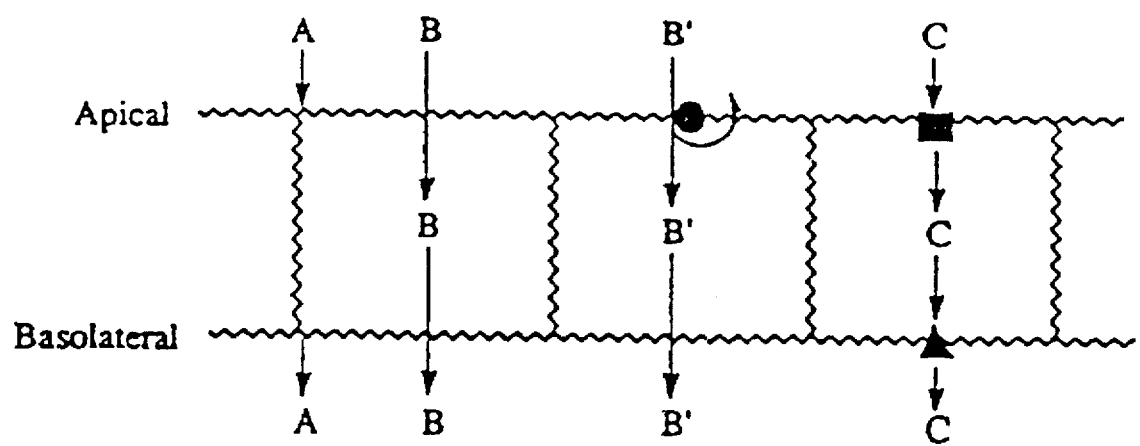
FIG. 1 is a schematic diagram showing possible pathways for flux of peptides across the intestinal mucosa or the BBB.

Pathway A, paracellular; pathway B, transcellular via passive diffusion; pathway B', transcellular via passive diffusion modified by an apically polarized efflux mechanism (●); pathway C, transcellular via peptide transporters (■, apical transporter; ▲, basolateral transporter).

DETAILED DESCRIPTION OF THE INVENTION

The following detailed description of the invention is provided to aid those skilled in the art in practicing the present invention. Even so, the following detailed description should not be construed to unduly limit the present invention, as modifications and variations in the embodiments herein discussed may be made by those of ordinary skill in the art without departing from the spirit or scope of the present inventive discovery.

General Overview

The objects of the present invention listed supra are achieved by providing esterase-sensitive, cyclic prodrugs of peptides and pNAs which, upon hydrolysis within the body, release the peptide or pNA as shown schematically below:

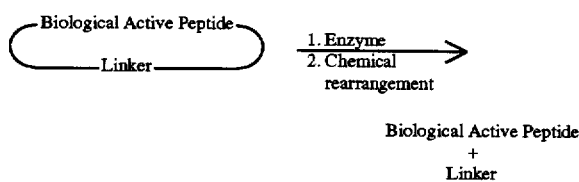

Using two broad formulas of possible linkers, this release of the peptide or pNA can be exemplified as follows:

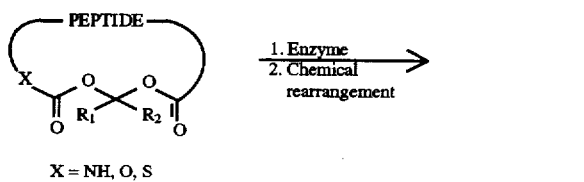

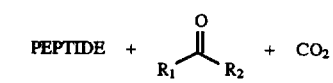

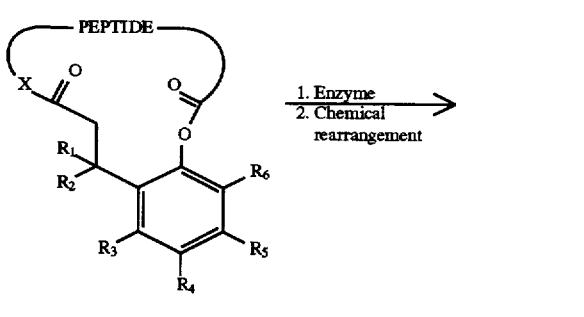

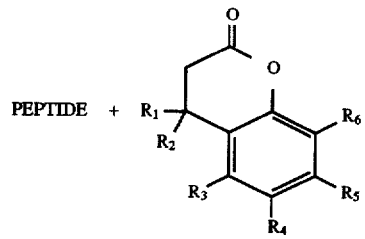

Numerous biologically active peptides can be cyclized according to the invention. The types of biologically active peptides useful in the present invention include peptide mimetics and peptides active in the central nervous system, such as peptides active for sedating, a peptide having cholecystokinin anti-anxiolytic activity, neurotensin, opioid receptor-specific peptides, and bradykinin antagonists; peptides useful for treating cardiovascular disease such as angiotensin converting enzyme inhibitors, renin modulators, renin inhibitors, and peptide mimetic renin inhibitors; vasoactive peptides, such as endothelin, tachykinins, atrial natriuretic peptide, zinc metalloproteinase inhibitors, calcitonin related peptides, neuropeptide Y, vasopressin and oxytocin; peptides useful in antithrombic therapy, such as RGD peptides and thrombin inhibitors; antimicrobial peptides, such as cecropins and magainin; peptides useful in antitumor therapy, such as mitogenic growth factors, and hormones such as growth hormone and enzyme inhibitors. Peptide nucleic acids useful in the present invention for the treatment of cancer and viral infections (Tidd, D. M., 1990; Flam, F., 1993).

The present invention, therefore, can be applied to all of the above-noted types of peptides by cyclizing the peptide of interest with a compound (i.e. a "linker") which is (a) capable of being reacted with the peptide in a cyclizing reaction scheme to produce a cyclic prodrug and (b) capable of being released from the cyclic prodrug by means of in vivo esterases to produce the peptide in its biologically active form. Preferred linker compounds according to the invention are compounds I–XII (Scheme 4).

Of the compounds I–IX, those of the following formulas are particularly important:

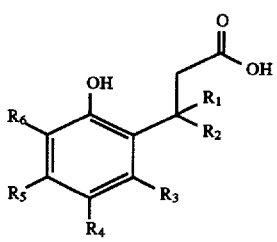

wherein $R_1$=CH$_3$, alkyl, phenyl, benzyl, halogen
$R_2$=CH$_3$, alkyl, phenyl, benzyl, halogen
$R_3$=CH$_3$, alkyl, alkenyl, phenyl, benzyl, halogen
$R_4$=OH, H, NO$_2$
$R_5$=H, CH$_3$, alkyl, alkenyl, phenyl, benzyl, halogen $R_6$=H, $CH_3$, alkyl, alkenyl, phenyl, benzyl, halogen,

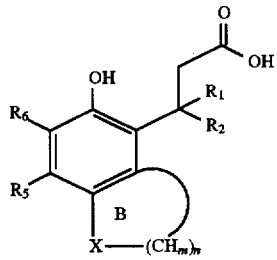
(II)

wherein
$R_1$=$CH_3$, alkyl, alkenyl, phenyl, benzyl, halogen
$R_2$=$CH_3$, alkyl, alkenyl, phenyl, benzyl, halogen
$R_5$=H, $CH_3$, alkyl, alkenyl, phenyl, benzyl, halogen
$R_6$=H, $CH_3$, alkyl, alkenyl, phenyl, benzyl, halogen,
Ring B can be aliphatic or aromatic
n=1, 2, 3, 4 ... 10
m=can be 1 or 2 depending if ring B is aliphatic, has double bond(s) or aromatic
X=O, S, NH, N-alkyl.

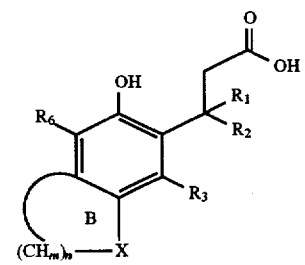
(III)

wherein
$R_1$=$CH_3$, alkyl, alkenyl, phenyl, benzyl, halogen
$R_2$=$CH_3$, alkyl, alkenyl, phenyl, benzyl, halogen
$R_3$=H, $CH_3$, alkyl, alkenyl, phenyl, benzyl, halogen
$R_6$=H, $CH_3$, alkyl, alkenyl, phenyl, benzyl, halogen,
Ring B can be aliphatic or aromatic
n=1, 2, 3, 4 ... 10
m=can be 1 or 2 depending if ring B is aliphatic or contains double bond(s) or aromatic
X=O, S, NH, N-alkyl.

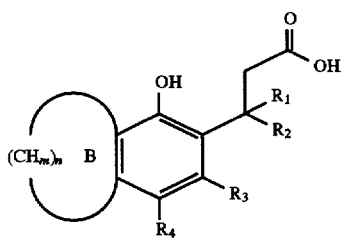
(IV)

wherein
$R_1$=$CH_3$, alkyl, alkenyl, phenyl, benzyl, halogen
$R_2$=$CH_3$, alkyl, alkenyl, phenyl, benzyl, halogen
$R_3$=$CH_3$, alkyl, alkenyl, benzyl, halogen
$R_4$=OH, H, $NO_2$
Ring B can be aliphatic or aromatic
n=1, 2, 3, 4 ... 10
m=can be 1 or 2 depending if ring B is aliphatic or contains double bond(s) or aromatic.

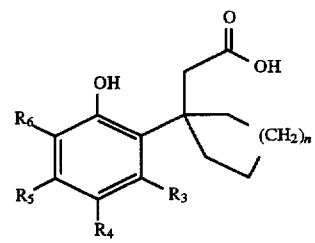
(V)

wherein
$R_3$=$CH_3$, alkyl, alkenyl, phenyl, benzyl, halogen
$R_4$=OH, H, $NO_2$
$R_5$=H, $CH_3$, alkyl, alkenyl, phenyl, benzyl, halogen
$R_6$=H, $CH_3$, alkyl, alkenyl, phenyl, benzyl, halogen
n=1, 2, 3, 4 ... 10,

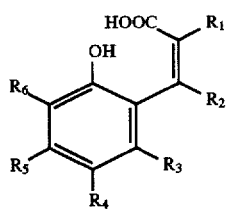
(VI)

wherein
$R_1$=$CH_3$, alkyl, alkenyl, phenyl, benzyl, halogen
$R_2$=$CH_3$, alkyl, alkenyl, phenyl, benzyl, halogen
$R_3$=$CH_3$, alkyl, alkenyl, phenyl, benzyl, halogen
$R_4$=OH, H, $NO_2$
$R_5$=$CH_3$, alkyl, alkenyl, phenyl, benzyl, halogen
$R_6$=H, $CH_3$, alkyl, alkenyl, phenyl, benzyl, halogen,

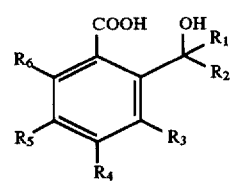
(VII)

wherein
$R_1$=$CH_3$, alkyl, alkenyl, phenyl, benzyl, halogen
$R_2$=$CH_3$, alkyl, alkenyl, phenyl, benzyl, halogen
$R_3$=$CH_3$, alkyl, alkenyl, phenyl, benzyl, halogen
$R_4$=OH, H, $NO_2$
$R_5$=H, $CH_3$, alkyl, alkenyl, phenyl, benzyl, halogen
$R_6$=H, $CH_3$, alkyl, alkenyl, phenyl, benzyl, halogen, (VIII)

wherein
$R_1$=$CH_3$, alkyl, alkenyl, phenyl, benzyl, halogen
$R_2$=$CH_3$, alkyl, alkenyl, phenyl, benzyl, halogen
$R_3$=$CH_3$, alkyl, alkenyl, phenyl, benzyl, halogen
$R_4$=OH, H, $NO_2$
$R_5$=H, $CH_3$, alkyl, phenyl, benzyl, halogen $R_6$=H, $CH_3$, alkyl, alkenyl, phenyl, benzyl, halogen, and

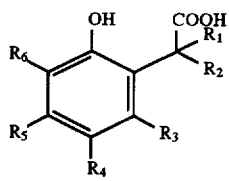
(IX)

wherein $R_1$=$CH_3$, alkyl, alkenyl, phenyl, benzyl, halogen $R_2$=$CH_3$, alkyl, alkenyl, phenyl, benzyl, halogen $R_3$=$CH_3$, alkyl, alkenyl, phenyl, benzyl, halogen $R_4$=OH, H, $NO_2$ $R_5$=H, $CH_3$, alkyl, alkenyl, phenyl, benzyl, halogen $R_6$=H, $CH_3$, alkyl, alkenyl, phenyl, benzyl, halogen.

Of the acyloxyalkoxy derivatives X-XII, those of the following formulas are particularly important:

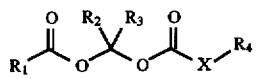
(X)

wherein $R_1$=carboxyl terminus of peptides and pNAs $R_2$=H, CH3, alkyl, alkenyl, phenyl, benzyl $R_3$=H, CH3, alkyl, alkenyl, phenyl, benzyl, $R_4$=amino, hydroxyl, sulfydryl, terminus of side chain or backbone of peptides and pNAs,

X=NH, O, S

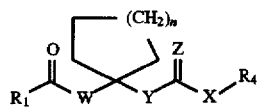
(XI)

wherein $R_1$=carboxyl terminus of peptide and pNAs $R_4$=amino, hyroxyl and sulfhydryl terminus of side chain or backbone of peptides and pNAs n=0, 1, . . . 15

W=S, O

Y=S, O

Z=S, O,

X=NH, O, S

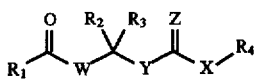
(XII)

wherein $R_1$=carboxyl terminus of peptide and pNAs $R_2$=H, CH3, alkyl, alkenyl, phenyl, benzyl $R_3$=H, CH3, alkyl, alkenyl, phenyl, benzyl,

W=S, O

X=NH, O, S

Y=S, O

Z=S, O $R_4$=amino, hydroxyl and sulfhydryl terminus of side chain or backbone of peptides and nucleic acids

Method of Preparation

Described below in Example 1 is a method specifically developed for making a cyclic prodrug of an analog of Delta Sleep Inducing Peptide (DSIP) analogs. Based on these studies with the DSIP analog, the inventors have developed a methodology generally useful for preparing cyclic prodrugs of linear peptides that would exhibit structural features (e.g., reduced relative size, intramolecular hydrogen bond, amphophilic characteristics) more favorable for enhanced cell membrane permeability and metabolic stability.

The general method of the invention will now be exemplified by means of several specific peptides: the Delta Sleep Inducing Peptide (DSIP) analog (Example 1); and selected opioid peptides-[$Leu^5$]-enkephalin (Example 2); a μ-selective opioid peptide (Example 3); δ-selective opioid receptor agonists including deltorphin, deltorphin analogs, and TIPP [ψ] (Example 4).

EXAMPLE 1

Synthesis of Cyclic Prodrugs of Delta Sleep Inducing Peptide (DSIP) Analog

Delta Sleep Inducing Peptide (DSIP) analog (Trp-Ala-Gly-Gly-Asp-Ala) (SEQ. ID NO. 1) is prepared as cyclic prodrugs 1a and 1b:

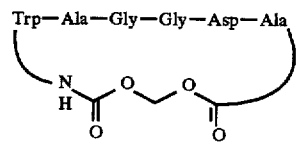
1a

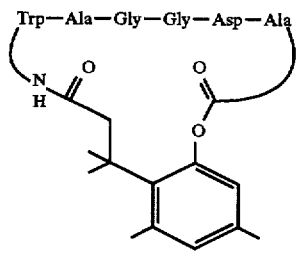
1b as follows.

Synthetic Procedure for Compound 1a

The synthetic procedure for preparing compound 1a is divided into schemes 5, 6 and 7, as follows.

SCHEME 5
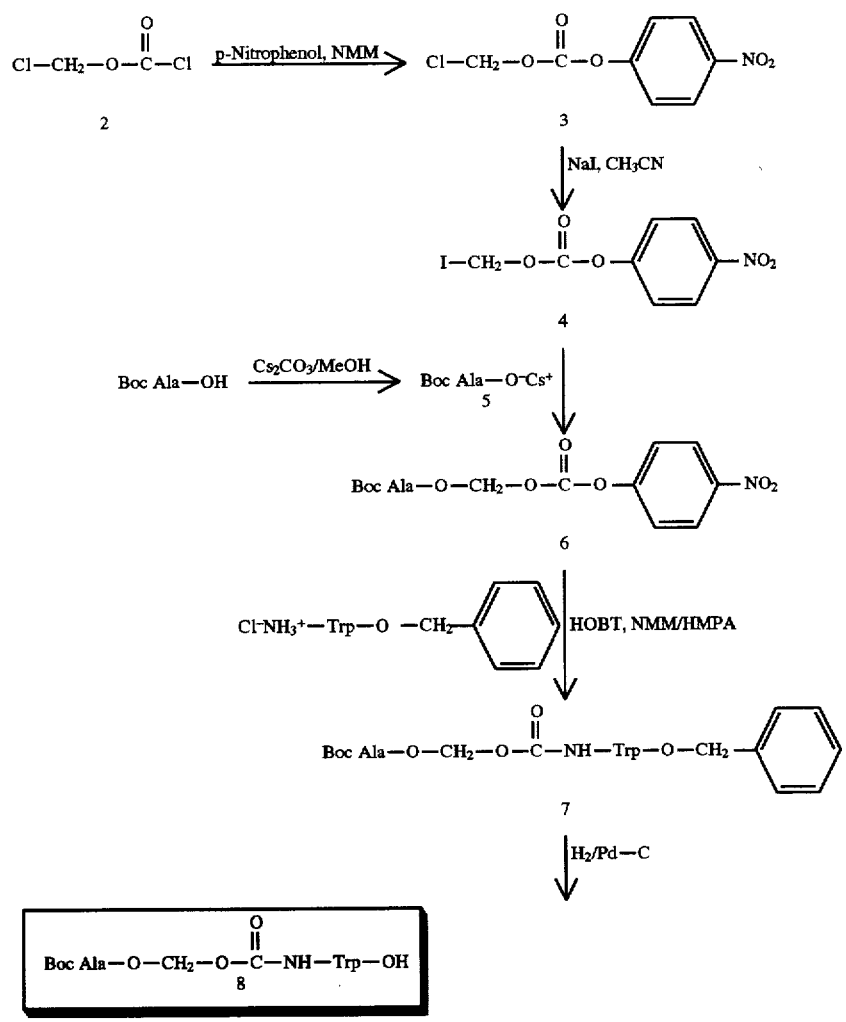
SCHEME 6
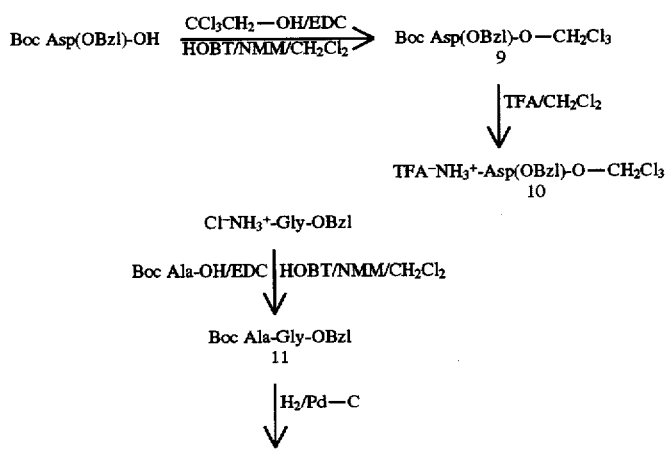

-continued
SCHEME 6
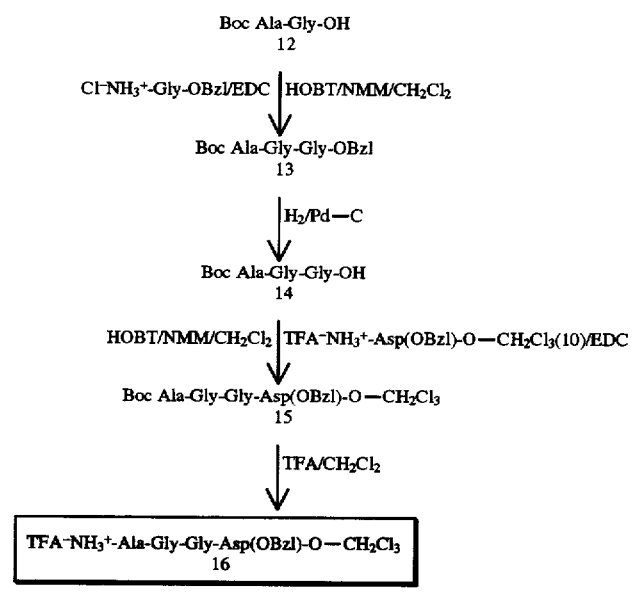
SCHEME 7
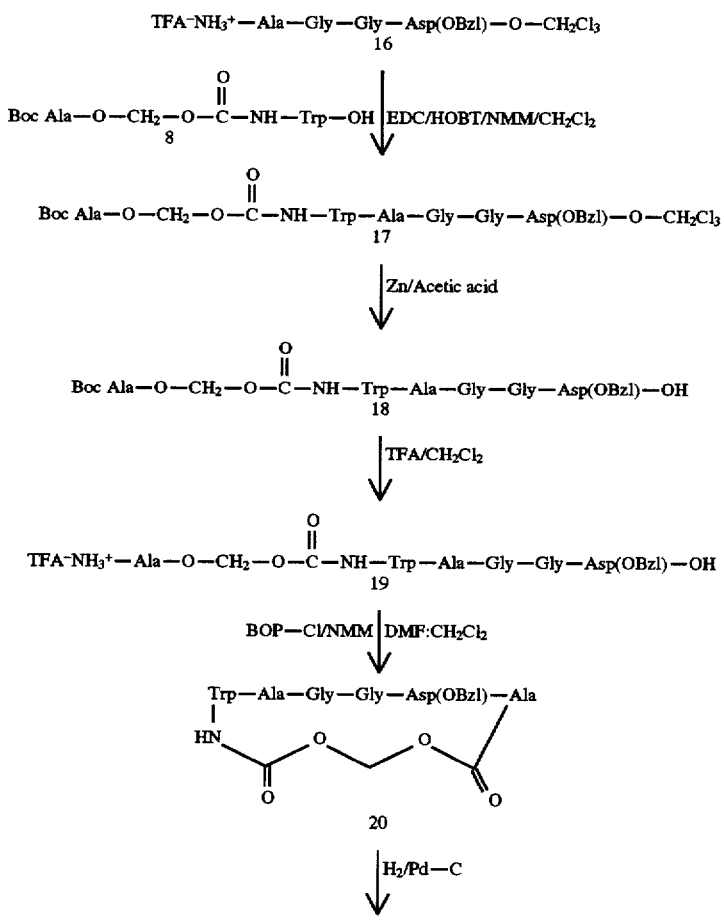

-continued
SCHEME 7

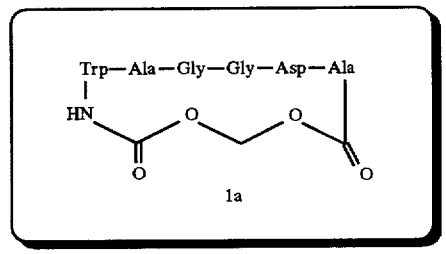

1a

Scheme 5 shows the synthesis of compound 8, in which the promoiety is inserted in between Boc-alanine and a trytophan residue. This is achieved by first reacting 1-chloromethyl- chloroformate 2 with p-nitrophenol in the presence of N-methyl morpholine to yield 3. Substitution of chloride in 1-chloromethyl p-nitrophenol carbonate 3 with iodide is accomplished by reacting 3 with sodium iodide to give 1-iodomethyl p-nitrophenol carbonate (4) in quantitative yield. This iodo compound 4 is reacted with the cesium salt of Boc-alanine to yield Boc-alanineoxymethyl-p-nitrophenol carbonate 6.

This reaction works better with the cesium salt of Boc-alanine than with the sodium or potassium salts. Treatment of compound 6 with tryptophanbenzyl ester hydrochloride in the presence of N-methyl morpholine, 1-hydroxy benzotriazole (HOBT), and hexamethyl phosphoramide (HMPA) gives Boc-alanineoxymethyl carbonyl-N- tryptophan benzyl ester 7. Compound 7 is then treated with 10% Pd-C in the presence of hydrogen gas to obtain Boc-alanineoxymethyl-carbonyl-N-tryptophan 8.

Scheme 6 illustrates the solution phase synthesis of the tetra-peptide 16 using standard Boc amino acid chemistry. The synthesis is started from the Asp residue; the two carboxyl groups in the amino acid are protected with selective protecting groups (OBzl and OTce) which can be removed under different conditions. This is achieved by protecting the α-carboxyl group of the Boc-Asp(OBzl)-OH as a trichloroethyl ester (Tce), which is quite stable to acidic conditions, and which can be easily removed by Zn/AcOH. Treatment of Boc-Asp(OBzl) with trichloroethanol in the presence of EDC/HOBT and N-methyl morpholine gives the Boc-Asp(OBzl)-OTce 9. Boc-Asp(OBzl)-OTce 9 is treated with 50% TFA to remove the Boc group, and gives Asp (OBzl)-OTce 10. The tripeptide Boc-Ala-Gly-Gly-OH 14 is synthesized using standard Boc strategy and the EDC/HOBT coupling method. Treatment of the tripeptide 14 with compound 10 in the presence of EDC/HOBT gives the tetrapeptide 15, which is treated with 50% TFA to yield tetrapeptide 16.

Scheme 7 shows how all the fragments are assembled in order to obtain the cyclic peptide prodrug 1a. This is accomplished by first treating the tetrapeptide 16 with Boc-alanineoxymethyl- carbonyl-N-tryptophan 8 in the presence of EDC/HOBT to give the linear hexapeptide prodrug 17. Both the protecting groups (Boc as well as trichloroethyl ester) from compound 17 are removed by treating first with Zinc in acetic acid and then with 50% TFA to give the deprotected linear hexapeptide 19. This linear hexapeptide 19 is used for the next step of the cyclization reaction. The cyclization of this linear hexapeptide 19 is accomplished by the standard high dilution technique using BOP-Cl (N,N-Bis(2-oxo-3-oxazolidinyl)-phosphinic Chloride) as an activating reagent in the presence of dimethylaminopyridine and N-methylmorpholine to yield cyclic peptide prodrug 20. The final deprotection of the benzyl group is accomplished using catalytic hydrogenation (Pd-C, $H_2$ method) to produce the cyclic peptide prodrug 1a.

Experimental Procedure for Compound 1a 1-chloromethyl p-nitrophenol carbonate (3): The synthesis is started by using a method developed by Alexander et al., 1988. 3.2 ml (0.036 mol) of 1-chloromethyl-chloroformate (Fluka chemicals) is added into an ice cold reaction mixture of 5 g (0.036 mol) of p-nitrophenol (Aldrich) and 3.6 ml (0.036 mol) of N-methylmorpholine (Aldrich) in 50 ml of chloroform (Aldrich). The cooling bath is removed after 1 h, and the reaction mixture is stirred at room temperature for 24 h. The reaction mixture is extracted successively with water, 10% aqueous sodium bicarbonate, and water. The chloroform layer is dried over anhydrous $Na_2SO_4$, decanted and evaporated to give pure 1-chloromethyl p-nitrophenol carbonate (3), which is a light yellow oil. $^1$H-NMR ($CDCl_3$): 5.85 (2H, s), 7.42 (2H, d, J=8 Hz), 8.30 (2H, d, J=9 Hz).

1-iodomethyl p-nitrophenol carbonate (4): 5 g of sodium iodide (Aldrich) is added to a solution of 1-chloromethyl carbonate (3) in 50 ml of acetone (Aldrich), and the reaction mixture is stirred at 50° C. for 24 h. After stirring overnight, the solvent is evaporated and the residue is redissolved in diethyl ether (Fisher). The ether layer is washed successively with 10% aqueous sodium sulfite and then water, and dried over anhydrous $Na_2SO_4$. The ether layer is separated and evaporated to give 1-iodomethyl p-nitrophenol carbonate (4) as a yellow oil which is confirmed by NMR. $^1$H-NMR ($CDCl_3$): 6.03 (2H, s), 7.39 (2H, d, J=9 Hz), 8.24 (2H, d, J=9 Hz).

Boc-alanineoxymethyl-p-nitrophenol carbonate (6): The cesium salt of Boc-alanine (5) is made by reacting 2 g (0.01 mol) of Boc-Alanine (Aldrich) with 1.7 g of cesium carbonate (Aldrich) in 30 ml of methanol. After stirring for 1 h, the solvent is evaporated to give the cesium salt of Boc-Ala as a white solid, which is confirmed by NMR. The cesium salt of Boc-Alanine (5; 0.96 g, 3 mmol) is added to an ice-cold and stirred solution of 1 g (3 mmol) of iodomethyl p-nitrophenol carbonate in 50 ml of dimethylformamide (DMF; Aldrich) followed by addition of 2 g of Boc-Alanine over a period of 2 h. Then, the reaction mixture is stirred at room temperature for 20 h. The solvent is evaporated and the residue is dissolved in 100 ml of ethyl acetate and washed with 10% NaOH and water. The organic layer is dried over anhydrous $Na_2SO_4$ and the solid is decanted out. The ethyl acetate layer is evaporated to give Boc-alanineoxymethyl-p-nitrophenol carbonate (6) as a yellow oil. $^1$H-NMR ($CDCl_3$): 1.28–1.30 (12H, br), 4.23 (1H, br), 5.43 (1H, d, J=7.4 Hz), 5.81 and 5.74 (2H, dd, J=5.5 Hz), 7.27 (2H, d, J=9 Hz), 8.08 (2H, d, J=7.3 Hz).

Boc-alanineoxymethyl carbonyl-N-tryptophan benzyl ester (7): A solution of 400 mg of Boc-alanineoxy-methyl-p-nitrophenol carbonate (6), 345 mg of tryptophan benzyl ester hydrochloride (Aldrich), 142 mg of HOBT (Aldrich), and 0.104 ml of NMM (Aldrich) in 40 ml of HMPA (Aldrich) is stirred at room temperature for 24 h. The reaction mixture is diluted with 300 ml of dichloromethane (DCM), followed by repeated washing with cold 1% NaOH. The DCM layer is dried over $Na_2SO_4$, decanted, and evaporated to yield Boc-alanineoxymethyl carbonyl-N-tryptophan benzyl ester (7) as an oil. $^1$H-NMR ($CDCl_3$): 1.35–1.43 (3H, br), 1.44 (9H, s), 3.30 (2H, d, J=5.4 Hz), 4.70 (1H, br), 4.89–4.98 (1H, br), 5.04 (2H, s), 5.69 (2H, br), 6.82 (2H, br), 7.07–7.31 (8H, br), 7.50 (1H, d, J=7.4 Hz). FABMS: 539 (M+1).

Boc-alanineoxymethylcarbonyl-N-tryptophan (8): In a 100 ml round bottom flask equipped with stirring bar, 200 mg of Boc-alanineoxymethyl carbonyl-N-tryptophan benzyl ester (7) is dissolved in 25 ml of absolute ethanol (Aldrich) followed by addition of 30 mg of 10% Pd-C (Aldrich). The reaction mixture is stirred under hydrogen gas atmosphere using a hydrogen balloon on the top of the round bottom flask. After 24 h, the reaction mixture is filtered and the filtrate is concentrated to furnish Boc-alanineoxymethylcarbonyl-N-tryptophan (8). Compound 8 is checked by MS and NMR. $^1$H-NMR (($CD_3$)$_2$CO): 1.30 (3H, d, J=6.9 Hz), 1.39 (9H, s), 3.19–3.43 (2H, m), 4.16 (1H, d, J=6.2 Hz), 4.53–4.54 (1H, br), 4.78 (1H, br), 5.62–5.74 (2H, br), 7.03 (1H, t, J=6.8 Hz), 7.10 (1H, t, J=6.8 Hz)), 7.38 (1H, d, J=7.5 Hz), 7.63 (1H, d, J=7.8 Hz). FABMS: 449 (M+1).

Boc-Asp(OBzl)-OTce (9): Synthesis of the peptide segment is started by making the trichloroethanol ester of Boc-Asp (OBzl)-OH (Shioiri et al., 1989). This is achieved by stirring 1 g (3 mmol) of Boc-Asp(OBzl)-OH (Sigma), 0.4 ml of (3 mmol) 2,2,2-trichloroethanol (Aldrich), 100 mg of DMAP (dimethylaminopyridine; Aldrich), and 576 mg (3 mmol) of EDC (Aldrich) in 50 ml of DCM for 3 h at 0° C. and for 20 h at room temperature. The precipitate is filtered out and the filtrate is diluted with 100 ml of ethyl acetate. The ethyl acetate solution is extracted with 10% aqueous citric acid, water, saturated $NaHCO_3$, water and saturated brine. Then, the ethyl acetate layer is dried over anhydrous $Na_2SO_4$, decanted, and concentrated to give an oil. The crude oily product is purified by washing with petroleum ether to give Boc-Asp(OBzl)-OTce (9). $^1$H-NMR ($CDCl_3$): 1.45 (9H, s), 2.93 and 3.15 (2H, dd, J=17 Hz and 4.5 Hz), 4.67 and 4.75 (2H, dd, J=12.3 Hz), 4.7–4.75 (1H, m), 5.13 (2H, s), 5.56 (1H, d, J=9 Hz), 7.34 –7.38 (5H, m). FABMS: 454 (M+1)

Asp(OBzl)-OTce (10): The t-Boc group of 1 g (2.2 mmol) of Boc-Asp(OBzl)-OTce is deprotected using 50 ml of 50% TFA in DCM, and the reaction mixture is stirred for 45 minutes. Volatile compounds in the reaction mixture are removed by rotary evaporator under vacuum.

The residue is triturated and washed with dry ether, and the solid is isolated by decantation. The solid of Asp(OBzl)-OTce (10) is dried under vacuum to remove the residual ether, and is used in the next step without further purification. FABMS: 354 (M+1).

Boc-Ala-Gly-OBzl (11): One equivalent of EDC [1-(3-dimethylaminopropyl)3-ethylcarbodiimide.hydrochloride] (1 g, 5.3 mmol, Aldrich) is added into a cold stirred solution of 1 g (5.3 mmol) Boc Alanine (Sigma), 1.07 g of (5.3 mmol) of Gly-OBzl (Sigma), 0.71 g of HOBT (Aldrich), and 0.5 ml of NMM in 50 ml DCM. The reaction mixture is stirred at 0° C. for 3 h and at ambient temperature for 22 h. The precipitate is filtered out and the filtrate is diluted with 100 ml of ethyl acetate. The organic layer is washed with 10% aqueous citric acid, water, saturated $NaHCO_3$, water, and saturated brine. The organic layer is dried over anhydrous $Na_2SO_4$ and the solid is decanted from the mixture. The organic solvent is evaporated and the residue is recrystallized using petroleum ether to give a colorless solid of Boc-Ala-Gly-OBzl (11). $^1$H-NMR ($CDCl_3$): 1.35 (3H,d, J=6 Hz), 1.42 (9H, s), 4.05 (2H, d, J=5 Hz), 4.25 (1H, m), 5.15 (2H, s), 5.28 (1H, d, J=5 Hz), 7.02 (1H, br), 7.33 (5H, s). FABMS: 337 (M+1).

Boc-Ala-Gly-OH (12): 1 g (3 mmol) of Boc-Ala-Gly-OBzl (11) is dissolved in 50 ml of absolute ethanol (Aldrich) followed by addition of 100 mg of 10% Pd-C (Aldrich) in a 100 ml round bottom flask equipped with a stirring bar. The reaction mixture is stirred under hydrogen gas atmosphere using a balloon on the top of the round bottom flask. After 24 h, the reaction mixture is filtered to remove the Pd-C; the filtrate is evaporated to give Boc-Ala-Gly-OH (12). $^1$H-NMR ($CDCl_3$): 1.33 (3H, d, J=7 Hz), 1.41 (9H, s), 3.97 (2H, d, J=5.6 Hz), 4.2 (1H, m), 6.18 (1H, br), 7.50 (1H, br). FABMS: 247 (M+1).

Boc-Ala-Gly-Gly-OBzl (13): One equivalent of 0.39 g (2 mmol) EDC (Aldrich) is added into a stirred solution of 0.5 g (2 mmol) of Boc Ala-Gly-OH (12), 0.4 g of (2 mmol) of Gly-OBzl (Sigma), 0.27 g of HOBT (Aldrich), and 0.2 ml of NMM in 100 ml of DCM at ice bath temperature. The reaction mixture is stirred for 3 h at 0° C. and 22 h at ambient temperature. The reaction mixture is concentrated using a rotary evaporator, and the residue is dissolved in 100 ml of ethyl acetate. The ethyl acetate solution is extracted with 10% $NaHCO_3$ and water. The organic layer is dried over anhydrous $Na_2SO_4$ and isolated by decantation. Then, the ethyl acetate is evaporated to furnish the Boc-Ala-Gly-Gly-OBzl (13) as a yellow oil which is confirmed by MS and NMR. $^1$H-NMR ($CDCl_3$): 1.28 (3H, d, J=7.2 Hz), 1.31 (9H, s), 3.85–4.15 (5H, m), 5.06 (2H, s), 5.45 (1H, br), 7.25 (5H, br), 7.41 (1H, br). FABMS: 394 (M+1).

Boc-Ala-Gly-Gly-OH (14): 0.5 g (1.3 mmol) of Boc-Ala-Gly-Gly-OBzl (13) is dissolved in 25 ml of absolute ethanol (Aldrich) in a 50 ml round bottom flask equipped with a stirring bar, followed by addition of 50 mg of 10% Pd-C (Aldrich). The reaction mixture is stirred under hydrogen gas atmosphere using a balloon. After 24 h, the Pd-C catalyst is filtered out from the reaction mixture, and the filtrate is concentrated to furnish Boc-Ala-Gly-Gly-OH (14). $^1$H-NMR ($CDCl_3$): 1.39 (3H, d, J=7.2 Hz), 1.43 (9H, s), 3.99–4.15 (5H, m), 5.03 (1H, br), 6.91–7.03 (2H, br). FABMS: 325 (M+Na).

Boc-Ala-Gly-Gly-Asp(OBzl)-OTce (SEQ. ID NO. 2) (15): One equivalent of 0.99 g (5.16 mmol) of EDC (Aldrich) is added into a stirred solution of 1.6 g (5.13 mmol) of Boc Ala-Gly-Gly-OH (11), 2.4 g (5.13 mmol) of Asp(OBzl)-OTce (10), 0.69 g of HOBT (Aldrich), and 0.5 ml of NMM in 100 ml of DCM at ice bath temperature. The reaction mixture is stirred at 0° C. for 3 h and at ambient temperature for 22 h. The reaction mixture is concentrated by rotary evaporator under vacuum and the residue is dissolved in 250 ml of DCM. This solution is extracted with 10% $NaHCO_3$ and water. The organic layer is dried over anhydrous $Na_2SO_4$, decanted from the drying agent, and evaporated under vacuum. The residue is an oil of Boc-Ala-Gly-Gly-Asp (OBzl)-OTce (SEQ. ID NO. 2) (15). $^1$H-NMR ($DMSOd_6$): 1.17 (3H, d, J=7.2 Hz), 1.37 (9H, s), 2.85 and 2.97 (2H, dd, J=17 Hz and 6.2 Hz), 3.71–3.79 (3H, br), 3.98 (2H, br), 4.86 (2H, d, J=4.3 Hz), 5.12 (2H, s), 7.01 (1H, d, J=6.5 Hz), 7.33–7.37 (5H, br), 8.07 (2H, d, J=6 Hz), 8.54 (1H, d, J=7.8 Hz). FABMS: 645 (M+Li), 661 (M+Na).

Ala-Gly-Gly-Asp(OBzl)-OTce (SEQ. ID NO. 3) (16): The deprotection of the t-Boc group of 0.29 g (0.44 mmol) of Boc-Ala-Gly-Gly-Asp(OBzl)-OTce (SEQ. ID NO. 2) (15) is performed by stirring this compound in 50 ml of 50% TFA/DCM for 45 minutes. The volatile reagents are removed by rotary evaporator under vacuum. The residue is triturated into dry ether to give a solid. The solid product is washed with dry ether and isolated by decantation. The solid of Ala-Gly-Gly-Asp(OBzl)-OTce (SEQ. ID NO. 3) (16) is dried under vacuum and is used in the next step without further purification. $^1$H-NMR (DMSOd$_6$): 1.36 (3H, d, J=7.2 Hz), 2.85 and 2.98 (2H, dd, J=17 Hz and 6.0 Hz), 3.70–4.01 (6H, m), 4.86 (2H, d, J=4.1 Hz), 5.12 (2H, s), 7.36–7.37 (5H, br), 8.09 (2H, br), 8.24 (1H, br), 8.64 (1H, d, J=7.2 Hz). FABMS: 538 (M+1).

Boc-Ala-(OCH$_2$OCO)-Trp-Ala-Gly-Gly-Asp(OBzl)-OTce (SEQ. ID NO. 4) (17): One equivalent of 0.09 g (0.44 mmol) of EDC (Aldrich) is added into a stirred solution of 0.2 g (0.44 mmol) of Boc-alanineoxymethyl carbonyl-N-tryptophan (8), 0.29 g (0.44 mmol) of Ala-Gly-Gly-Asp(OBzl)-OTce (SEQ. ID NO. 3) (16), 0.60 g of HOBT (Aldrich), and 0.04 ml of NMM in 50 ml of DCM at 0° C. The mixture was stirred for 3 h at 0° C. and for 22 h at ambient temperature. The reaction mixture is concentrated by rotary evaporator under vacuum, and the crude product is dissolved in 250 ml of DCM and washed with 10% NaHCO$_3$ and water. The DCM layer is dried over anhydrous Na$_2$SO$_4$ and decanted from the solid, and the solution is concentrated to give an oil of Boc-Ala-(OCH$_2$OCO)-Trp-Ala-Gly-Gly-Asp(OBzl)-OTce (SEQ. ID NO. 4) (17). FABMS: 972 (M+1), 994 (M+Na).

Boc-Ala-(OCH$_2$OCO)-Trp-Ala-Gly-Gly-Asp(OBzl)-OH (SEQ. ID NO. 5) (18): Boc-Ala-(OCH$_2$OCO)-Trp-Ala-Gly-Gly-Asp(OBzl)-OTce (SEQ. ID NO. 4) (17; 0.2 g, 0.2 mmol) is dissolved in 25 ml of glacial acetic acid (Aldrich) followed by addition of 1 g of Zn dust (Aldrich) in a 50 ml round bottom flask equipped with a stirring bar. The reaction mixture is stirred for 24 h, followed by dilution with acetic acid; the insoluble material is filtered out. The filtrate is concentrated to give Boc-Ala- (OCH$_2$OCO)-Trp- Ala-Gly-Gly-Asp(OBzl)-OH (SEQ. ID NO. 5) (18), which is used in the next step without further purification.

Ala-(OCH$_2$OCO)-Trp-Ala-Gly-Gly-Asp(OBzl)-OH (SEQ. ID NO. 6) (19): The t-Boc group of 18 is deprotected by addition of Boc-Ala-(OCH$_2$OCO)-Trp-Ala-Gly-Gly-Asp(OBzl)-OH (SEQ. ID NO. 5) (18; 0.17 g, 0.2 mmol) into 10 ml of 50% TFA in DCM in the presence of scavengers (2 g of phenol and 0.2 ml of ethanedithiol (Aldrich)), and the mixture is stirred for 45 minutes. The DCM is evaporated under the hood and the residue is triturated with dry ether to give a solid. The solid is washed with dry ether and isolated by decantation. The solid of Ala- (OCH$_2$OCO)-Trp-Ala-Gly-Gly-Asp(OBzl)-OH (SEQ. ID NO. 6) (19) is dried under reduced pressure. The product is purified further by preparative reverse phase HPLC using a C-18 column and a gradient of solvent A: H$_2$O/Acetonitrile/0.1% TFA and solvent B: Acetonitrile. $^1$H-NMR (DMSOd$_6$): 1.24 (3H, d, J=7.2 Hz), 1.29 (3H, d, J=7.2 Hz), 2.70–2.95 (2H, m), 3.15–3.19 (2H, m), 3.71–3.82 (4H, m), 4.35 (1H, m), 4.62 (1H, m), 5.10 (2H, s), 5.68 (2H, m), 6.95–7.20 (3H, br), 7.36 (5H, br), 7.68 (1H, br), 7.85 (1H, br), 8.12 (2H, br), 8.31 (4H, br). FABMS: 740 (M+1).

Cyclic Hexapeptide Prodrug 1a: Cyclization of 19 is accomplished by the formation of a peptide bond from the C-terminal aspartic acid to the N-terminal alanine. A solution of 236 mg (0.93 mmol) BOP-Cl and 1.85 ml of triethyl amine in 50 ml of dichloromethane at 0° C. is stirred in an oven dried round bottom flask (250 ml) under dry argon. Then, 138 mg (0.16 mmol) linear peptide 19 and 0.2 ml (1.85 mmol) of NMM in 50 ml of DCM are added dropwise over 2 h into the previous mixture. After 3 days at room temperature, the solvent is evaporated and the residue is dissolved in DCM (100 ml), followed by successive extraction with water, a saturated solution of citric acid, water, 10% aqueous sodium bicarbonate, and water. The DCM layer is dried over anhydrous Na$_2$SO$_4$ and isolated by decantation. The DCM is evaporated to give cyclic peptide 20. The cyclic peptide 20 is analyzed by an analytical reverse phase HPLC (C-18 column, 25 cm×4.6 mm, 1 mL/min) using a gradient of solvent A: H$_2$O/Acetonitrile/ 0.1% TFA and solvent B: Acetonitrile. The retention time of cyclic peptide 20 is at 14.3 minutes. FABMS: 722 (M+1).

Cyclic hexapeptide 20 (100 mg) is dissolved in 25 ml of absolute ethanol in a 50 ml round bottom flask equipped with a stirring bar (Aldrich), followed by addition of 20 mg of 10% Pd-C (Aldrich). The reaction mixture is stirred under hydrogen gas atmosphere using a balloon filled with H$_2$. After 24 h, the reaction mixture Pd-C catalyst is filtered, and the filtrate is concentrated to give a cyclic hexapeptide 1a. The crude product is purified using a preparative reverse phase Rainin HPX HPLC system using a C-18 Dynamax-300A column and a gradient of solvent A: H$_2$O/2 mM NH$_4$OAc and solvent B: ACN; 10%–50% in 48 min. The cyclic peptide 1a is analyzed by an analytical reverse phase HPLC (C-18 column, 25 cm×4.6 mm, 1 mL/min) using a gradient of solvent A: H$_2$O/Acetonitrile/0.1% TFA and solvent B: Acetonitrile. The retention time of cyclic peptide 1a is at 11.2 minutes. FABMS: 632 (M+1), High Resolution FABMS: Cal'd (M+1) 632.2316, Found 632.2319.

Synthetic Procedure for Compound 1b

Two approaches to the synthesis of cyclic peptide 1b are possible. The first method involves the synthesis of the linear peptide using the Fmoc approach on a solid support (Wang's Resin), and subsequent cyclization in solution phase, as illustrated in Scheme 8.

SCHEME 8

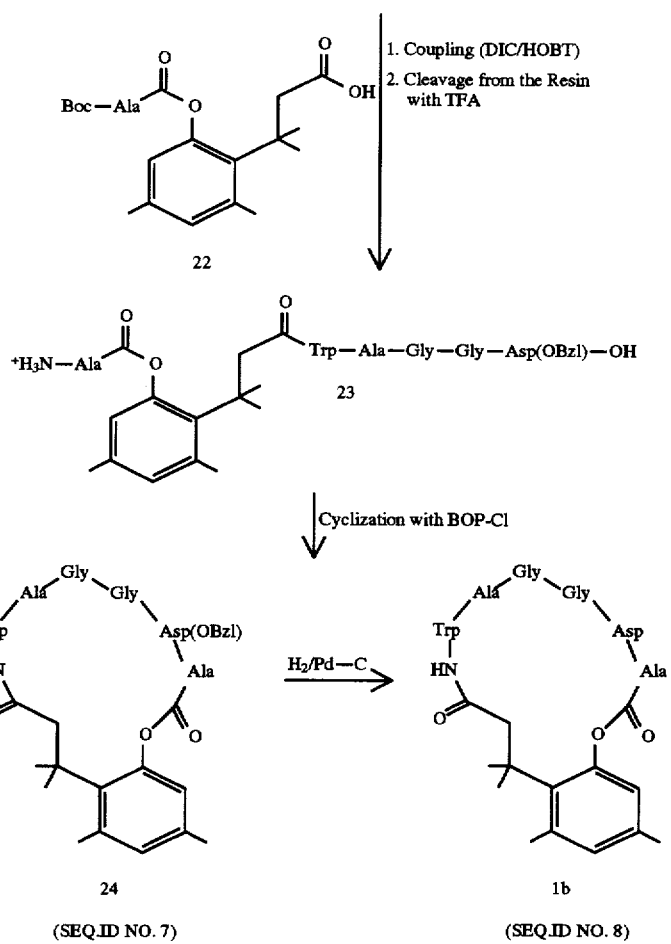

The second approach to the synthesis of cyclic peptide 1b involves complete solution phase synthesis of the cyclic peptide, as illustrated in Schemes 10 and 11.

Solid Phase Method (Scheme 8)

The incorporation of the pro-moiety 22 into the cyclic system requires the protection of the phenol hydroxyl group. Therefore, a key intermediate for the successful synthesis of the cyclic prodrug 1b is compound 22 (Scheme 9), where Boc-Ala is attached at the phenolic hydroxyl group through an ester bond.

SCHEME 9

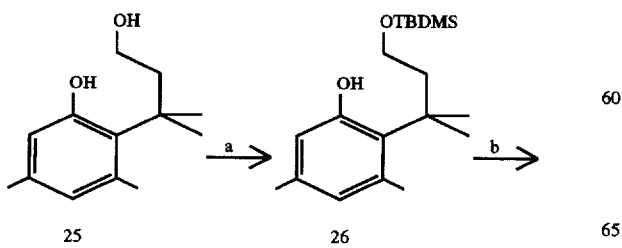

-continued
SCHEME 9

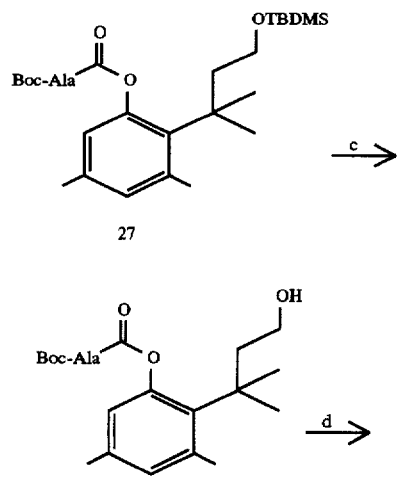

-continued
SCHEME 9

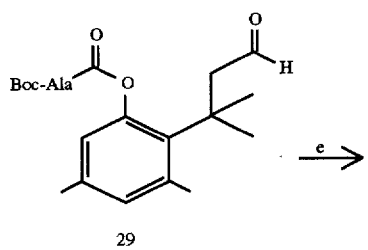

a) TBDMSCl/Triethylamine; b) Boc-Ala-OpNp, DMAP/DCM, reflux; c) HOAc/THF/H$_2$O; d) PCC; e) KMnO$_4$ The synthesis of 22 starts with commercially available 3,5-dimethylphenol, and the diol 25 is prepared in two steps with over 90% yield for each step by following literature procedures (Amsberry et al., 1991). The protection of the aliphatic hydroxyl group with t-butyldimethyl silyl (TBDMS) in the presence of triethylamine (TEA) in dichloromethane (DCM) gives the protected diol 26 in nearly quantitative yield. Reaction of the activated p-nitrophenol (pNP) ester of the Boc alanine with 26 in the presence of dimethyl aminopyridine (DMAP) in refluxing dichloromethane (DCM) gives 27 in 80% yield. Treatment of the TBDMS ether 27 with acetic acid in the presence of water and THF yields the primary alcohol 28, which is converted in a two step oxidation with pyridinium chlorochromate (PCC) and KMnO$_4$ to the key intermediate 22.

The solid phase synthesis (scheme 8) involves the attachment of β-benzyl-protected aspartic acid as the first amino acid to Wang's resin through activation of the carboxyl group directly with diisopropylcarbodiimide (DIC) (Atherton, E. and Sheppard, C.). The linear peptide 23 is synthesized by standard peptide synthesis using Fmoc chemistry. The last step of this procedure is the coupling of 22 onto the resin. Cleavage of the peptide from the solid support with 50% trifluoroacetic acid (TFA) gives the linear peptide 23 in 50% yield.

This linear peptide is used directly for the next step cyclization reaction without purification. The cyclization can be accomplished with BOP-Cl as the activating reagent to give cyclic peptide 24. The final deprotection of the benzyl group is accomplished through catalytic hydrogenation to give the desired product 1b.

Experimental Procedures of the Solid Phase Method

TBDMS-diol (26):

To a mixture of 11.63 g of the diol (25) and 9.3 g of the TBDMS chloride in 70 ml of DCM cooled with an ice-bath is added dropwise a solution of 30 ml of DCM and 31 ml of triethylamine during a period of 1 h with stirring. Then the reaction is warmed up to room temperature and kept stirring for 1 day; completion of the reaction is followed by TLC. The solvent is then evaporated, and the residue is dissolved in 250 ml of DCM, which is then washed with water (20 ml×4). After drying over MgSO$_4$ for 1 h, solvent evaporation gives 18.09 g of a white solid product (100%). The NMR spectrum of 26 is identical with the that reported in the literature.

Boc-Ala-TBDMS-diol (27): To a mixture of 5.18 g of the TBDMS-diol (26), 5 g of Boc-Ala-OpNP, and 2 g of DMAP is added 20 ml of anhydrous DCM. After refluxing for 7 h, 0.4 g of additional DMAP is added, and the reaction is kept refluxing for an additional 7 h. After solvent evaporation, the residual is dissolved into 200 ml of DCM, which is washed with saturated NaHCO$_3$ (20 ml×4), 1% HCl (20 ml×2), brine (20 ml×2). After drying over Na$_2$SO$_4$ and solvent evaporation, the residue is purified by column chromatography (silica gel) using a gradient of 5 to 10% ethyl acetate in hexane to give a colorless oil which later solidifies to give a white solid product (6.87 g, 84%). The product is characterized with $^1$H, $^{13}$C-NMR, MS, and elemental analysis. $^1$H-NMR (CDCl$_3$): 6.80 (1H, s, aromatic H), 6.50 (1H, s, aromatic H), 5.18 (1H, m, NH), 4.51 (1H, m, NHC$\underline{H}$), 3.47 (2H, t, J=7.6 Hz, OCH$_2$), 2.51 (3H, s, PhCH$_3$), 2.21 (3H, s, PhCH$_3$), 2.01 (2H, m, OCH$_2$C$\underline{H}_2$), 1.54 (3H, d, J=7.3 Hz, CHC$\underline{H}_3$), 1.45 (15H, s, OC(CH$_3$)$_3$, C(CH$_3$)$_2$), 0.83 (6H, s, SiC(CH$_3$)$_3$, −0.04 (6H, s, Si(C$\underline{H}_3$)$_2$); CIMS (NH$_3$) (relative intensity): 494 (M+1, 1), 438 (4), 394 (9); HRMS: Cal'd for C$_{27}$H$_{48}$NO$_5$Si: 494.3302; Found: 494.3316; Elemental analysis; Cal'd for C$_{27}$H$_{47}$NO$_5$Si: C, 65.68; H, 9.59; N, 2.84; Found: C, 65.90; H, 9.91; N, 2.76.

Boc-Ala-alcohol (28): To 5.0 g of the Boc-Ala-TBDMS-diol (27) is added 19 ml of THF, 19 ml of H$_2$O, and 58 ml of AcOH. The reaction is kept stirring at room temperature for 1 h. TLC shows the disappearance of the starting material. Then the solvent is evaporated to give a colorless oil residue (4.8 g) which shows only one spot on TLC. However, this product is used directly for the oxidation without purification because of the potential of rearrangement during column chromatography. $^1$H-NMR (CDCl$_3$):6.79 (1H, s, aromatic), 6.51 (1H, s, aromatic), 5.35 (1H, m, NH), 4.47 (1H, m, NHC$\underline{H}$), 3.49 (2H, m, HOC$\underline{H}_2$), 2.49 (3H, s, PhCH$_3$), 2.20 (3H, s, PhCH$_3$), 2.04 (2H, m, HOCH$_2$C$\underline{H}_2$), 1.54 (3H, d, J=7.4 Hz, CHC$\underline{H}_3$), 1.46 (6H, s, C(CH$_3$)$_2$), 1.42 (9H, s, C(CH$_3$)$_3$).

Boc-Ala-TBDMS-acid (22): To a solution of 4.38 g of PCC in 200 ml of DCM is added dropwise a solution of the alcohol 28 (3.90 g) in 200 ml of DCM. Reaction color changes from orange to black during addition. After stirring the reaction at room temperature for 1 h, TLC shows the total disappearance of the starting material and the appearance of a new product. After filtration through Celite and solvent evaporation, and subsequent purification with a short silica gel column, 3.08 g of an oil product is obtained (79%). The oily product is then dissolved in 40 ml of acetone, which is added dropwise to a solution of 1.42 g of KMnO$_4$ in 40 ml of acetone-H$_2$O (1:1). After the reaction is kept stirring at room temperature for 17 h, TLC shows the disappearance of the aldehyde. Then acetone is evaporated from the reaction mixture and the residue is filtered through Celite. After filtration, the pH of the solution is about 8, and is adjusted to pH 3 with dilute HCl. The mixture is then extracted with ethyl acetate (100 ml×3), and the combined organic extracts are dried over MgSO$_4$ overnight. Solvent evaporation gives a white solid product (2.9 g, 88%). $^1$H-NMR (CDCl$_3$): 6.72 (1H, s, aromatic), 6.44 (1H, s, aromatic), 5.09 (1H, m, NH), 4.30 (1H, m, NHC$\underline{H}$), 2.74 (2H, b, CH$_2$COO), 2.44 (3H, s, PhCH$_3$), 2.13 (3H, s, PhCH$_3$), 1.46 (9H, m, CHC$\underline{H}_3$, C(CH$_3$)$_2$), 1.35 (9H, s, C(CH$_3$)$_3$). FABMS: 394 (M+1), 338, 294; HRMS: Cal'd (M+1), 394.2230; Found: 394.2231. Elemental analysis:

Cal'd for $C_{21}H_{31}NO_6$: C, 64.10, H, 7.94, N, 3.56; Found: C, 63.92, H, 8.10, N, 3.30.

Synthesis of the Linear Peptide (23): A typical synthesis uses Wang's alkoxy resin (Bachem Bioscience). Fmoc-protected amino acids are used for the solid phase peptide synthesis unless otherwise indicated. The coupling of the first amino acid (β-benzyl-aspartic acid) requires direct activation of the carboxyl groups with diisopropylcarbodiimide (DIC) for optimal yields. The coupling of the subsequent amino acids uses the DIC/HOBT method, and the reaction is monitored with the ninhydrin test, as well as by the weight of the resin. The final cleavage of the peptide from the resin is accomplished by treatment with 50% TFA/DCM. $^1$H-NMR ($CD_3OD$): 7.54 (1H, d, aromatic), 7.31 (6H, m aromatic), 7.10 (1H, m, aromatic), 7.02 (1H, m aromatic), 6.98 (1H, b, aromatic), 6.81 (1H, b, aromatic), 6.58 (1H, b, aromatic), 5.10 (2H, s, $PhCH_2$), 4.83 (1H, t, α-H), 4.54 (1H, t, α-H), 4.37 (1H, m, α-H), 4.15 (1H, m, α-H), 3.88 (2H, b, Gly-α-H), 3.61 (2H, b, 1H, Gly-α-H), 3.17–2.89 (4H, m, Asp-$CH_2$, Trp-$CH_2$), 2.63 (2H, s, $(CH_3)_2CC\underline{H}_2CO$), 2.43 (3H, s, $PhCH_3$), 2.19 (3H, s, $PhCH_3$), 1.71 (3H, d, Ala-$CH_3$), 1.46 (6H, s, $C(CH_3)_2$), 1.21 (3H, d, Ala-$CH_3$); FABMS: 870.5 (M+1).

Cyclic Peptide with Aspartic Acid Protection (24): To 94 mg of the linear peptide (23) is added 10 ml of anhydrous DMF, 240 ml of anhydrous DCM, and 0.1 ml of NMM and BOP-Cl. The reaction solution is kept stirring for 34 h. TLC shows the disappearance of the starting material. Then the reaction mixture is washed with water (20 ml×2) and dried over $MgSO_4$ for 2 h. The crude product is purified by reverse phase HPLC using a C-18 column and 70% methanol in water as solvent to give 7 mg of a pure cyclic peptide 24. $^1$H-NMR ($CDCl_3$): 6.5–7.6 (19H, NH, aromatic), 5.14 (2H, m, $PhCH_2$), 4.82 (1H, m, α-H), 4.52 (1H, m, α-H), 4.38 (1H, m, α-H), 3.66–4.03 (5H, m, α-H), 2.88–3.11 (4H, Asp-$CH_2$, Trp-$CH_2$), 2.71 (1H, d, $(CH_3)_2CC\underline{H}_2$), 2.51 (3H, s, $CH_3$), 2.40 (1H, d, $(CH_3)_2CC\underline{H}_2$), 2.17 (3H, s, $CH_3$), 1.5–1.7 (9 H, m, $CH_3$), 1.13 (3H, d, $CH_3$); FABMS: 852.7 (M+1); HRMS: Cal'd (M+1): 852.3932, Found: 852.3953.

Cyclic peptide (1b): To 7 mg of the cyclic peptide with benzyl protection of the β-carboxyl group of aspartic acid is added 20 ml of absolute ethanol and 3 mg of Pd-C 10%. Then the reaction is kept stirring at room temperature under 1 atm of hydrogen for 22 h. Filtration of the reaction mixture and washing of the Pd-C with methanol (10 ml×4), followed by solvent evaporation, gives a colorless residue which is washed with chloroform. After drying under vacuum, 3.5 mg of product is obtained. $^1$H-NMR ($CD_3OD$): 6.59–7.51 (7H, aromatic), 4.84 (1H, m, α-H), 4.40–4.62 (2H, m, α-H), 3.60–4.23 (5H, m, α-H), 2.78–3.20 (4H, m, Asp-$CH_2$, Trp-$CH_2$), 2.44 (1H, d, $(CH_3)CC\underline{H}_2$), 2.36 (3H, s, $CH_3$), 2.18 (3H, s, $CH_3$), 2.04 (1H, d, $(CH_3)CC\underline{H}_2$), 1.10–1.70 (12H, m, $CH_3$). FABMS: 784 (M+Na), 762 (M+1); HRMS: Cal'd (M+1), 762.3463, Found, 762.3481.

Solution Phase Method

The synthesis can also be accomplished with the solution phase approach (Scheme 10–11). For the solution phase approach, Boc strategy is employed (instead of the Fmoc strategy) for practical reasons, which include the fact that all side products during deprotection can be evaporated and the desired product can be easily purified through recrystallization. However, in using the solution phase approach, there is the need to temporarily protect the terminal carboxyl group during the synthesis of the linear peptide. The key to this solution phase approach is the protecting group on the α-carboxyl group of aspartic acid (see Scheme 6). The selective deprotection of the α-carboxyl group of Asp must be carried out under conditions which will not affect the ester bond of the pro-moiety. The protection of α-carboxy group of Asp with trichloroethanol ester (Tce) can easily be cleaved with Zn in acetic acid. The protection of α-carboxyl group to give compound 10 with trichloroethanol is accomplished according to Scheme 6. The synthesis of the tetrapeptide 16 is accomplished by using standard Boc amino acid chemistry as shown in Schemes 6 and 10. Tetrapeptide 16 (Scheme 10) is coupled with Boc-Trp-OH to give pentapeptide 32. The Boc-protecting group in 32 is removed with TFA/$CH_2Cl_2$ to give pentapeptide 33. Pentapeptide 33 is coupled with the promoiety Boc Ala-(Prom)-OH (22) in the presence of EDC/HOBT to give the linear hexapeptide prodrug 34 (Scheme 11). Hexapeptide is treated with Zn in acetic acid followed by treatment with TFA in dichloromethane to remove trichloroethanol ester group (Tce) and t-Boc protecting group, respectively. These two reactions give the unprotected hexapeptide 36. This hexapeptide is first purified by preparative HPLC before it is subjected to the macrolactamization. The hexapeptide 36 is cyclized as in the case of the solid phase approach using Bop-Cl/DMAP and NMM to give the cyclic peptide 24 which on treatment with $H_2$/Pd-C generates the desired cyclic peptide 1b.

Cyclic peptide 1b is purified by preparative HPLC using $C_{18}$ column with a solvent gradient of 2 mmol ammonium acetate and acetonitrile. The pure cyclic product 1b is characterized by $^1$H-NMR and MS.

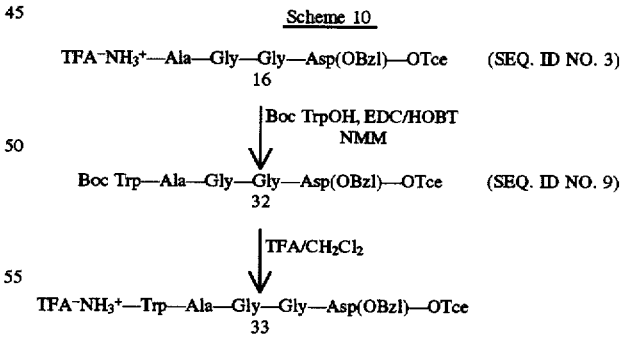

Scheme 10

TFA$^-$NH$_3^+$—Ala—Gly—Gly—Asp(OBzl)—OTce (SEQ. ID NO. 3)
16

↓ Boc TrpOH, EDC/HOBT
  NMM

Boc Trp—Ala—Gly—Gly—Asp(OBzl)—OTce (SEQ. ID NO. 9)
32

↓ TFA/$CH_2Cl_2$

TFA$^-$NH$_3^+$—Trp—Ala—Gly—Gly—Asp(OBzl)—OTce
33

Scheme 11

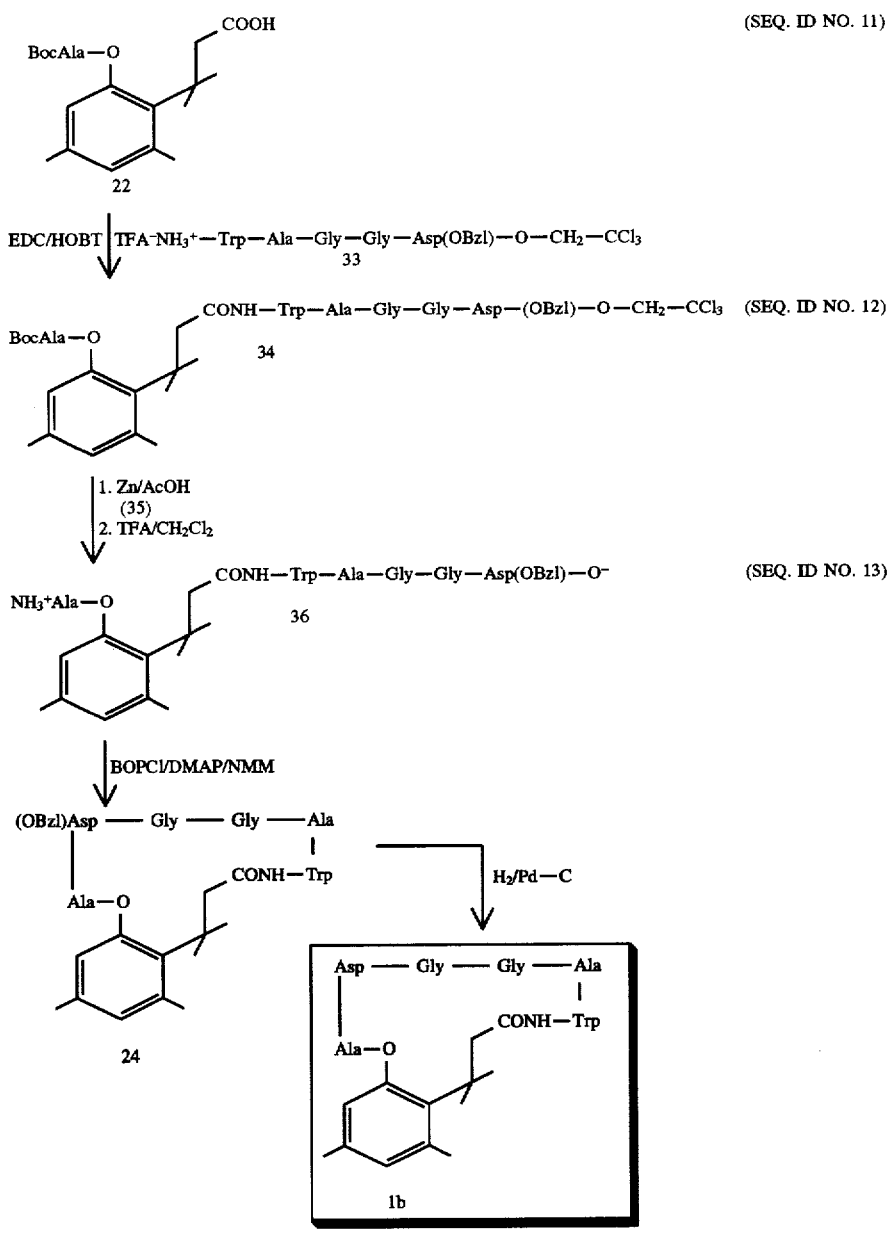

Experimental Procedures of Solution Phase Method

Boc-Trp-Ala-Gly-Gly-Asp(OBzl)-OTce (SEQ. ID NO. 9) (32):

1.12 g (1.76 mmol) of Ala-Gly-Gly-Asp(OBzl)-OTce (SEQ. ID NO. 3) (16) is added into a stirred solution 0.55 g of (1.76 mmol) of Boc Trp-OH, 0.35 g (1.8 mmol) of EDC (Aldrich), 0.243 g of HOBT (Aldrich) and 0.2 ml of NMM in 50 ml of DCM at ice bath temperature. The reaction mixture is stirred at 0° C. for 3 h and at ambient temperature for 22 h. The reaction mixture is concentrated by rotary evaporator under vacuum and the residue dissolved in 250 ml of DCM. This solution is extracted with 10% NaHCO₃ and water. The organic layer is dried over anhydrous Na₂SO₄, decanted from the drying agent and evaporated under vacuum. The residue is an oil of Boc-Trp-Ala-Gly-Gly-Asp(OBzl)-OTce (SEQ. ID NO. 9) (32). ¹H-NMR (CDCl₃): 1.21 (3H, d, J=7.2 Hz), 1.43 (9H, s), 3.03 and 3.14 (2H, dd, J=16.8 Hz and 5.1 Hz), 3.23 (2H, d, J=6.8 Hz), 3.4–3.6 (1H, br), 3.74–3.85 (1H, br), 3.96 (2H, d, J=5.9 Hz), 4.23–4.30 (1H, br), 4.45–4.48 (1H, br), 4.7 (2H, d, J=11.8 Hz), 5.04–5.09 (1H, br), 5.14 (2H, s), 6.25–6.27 (1H, br), 7.05–7.40 (9H, br), 7.64 (2H, d, J=7.4 Hz), 8.67 (1H, br). FABMS: 825 (M+1), 847 (M+Na).

Trp-Ala-Gly-Gly-Asp (OBzl)-OTce (SEQ. ID NO. 10) (33):

The deprotection of t-Boc group of 0.29 g (0.44 mmol) of Boc-Trp-Ala-Gly-Gly-Asp(OBzl)-OTce (SEQ. ID NO. 9) (32) is done stirring this compound in 50 ml of 50% TFA/DCM in the presence of scavengers (1 g of phenol and 0.2 ml of ethanedithiol (Aldrich)) and the mixture is stirred for 45 minutes. The volatile reagents are removed by rotary evaporator under vacuum. Trp-Ala-Gly-Gly-Asp (OBzl)-OTce (SEQ. ID NO. 10) (33) is dried under vacuum and used in the next step without further purification.

Boc-Ala-(Prom)-Trp-Ala-Gly-Gly-Asp(OBzl)-OTce (SEQ. ID NO. 14) (34):

0.25 g (0.30 mmol) of Trp-Ala-Gly-Gly-Asp(OBzl)-OTce (SEQ. ID NO. 10) (33) is added into a stirred solution of 0.12 g of (0.30 mmol) of Boc Ala-Prom Trp-OH, 0.07 g (0.3 mmol) of EDC (Aldrich), 0.04 g of HOBT (Aldrich) and 0.03 ml of NMM in 50 ml of DCM at ice bath temperature. The reaction mixture is stirred at 0° C. for 3 h and at ambient temperature for 22 h. The reaction mixture is concentrated by rotary evaporator under vacuum and the residue dissolved in 250 ml of DCM. This solution is extracted with 10% NaHCO$_3$ and water. The organic layer is dried over anhydrous Na$_2$SO$_4$, decanted from the drying agent and evaporated under vacuum. The residue is an oil of Boc-Ala-(Prom)-Trp-Ala-Gly-Gly-Asp(OBzl)-OTce (SEQ. ID NO. 14) (34). $^1$H-NMR (CDCl$_3$): 1.37 (9H, s), 1.66 (6H, s), 2.12 (3H, s), 2.56 (3H, s), 2.41–2.75 (2H, br), 3.02–3.18 (4H, m), 3.3–4.4 (5H, m), 4.62 (2H, d, J=11.8 Hz), 5.13 (2H, s), 6.39 (1H, s), 6.72 (1H, s), 7.34 (5H, s), 7.07–7.53 (5H, br), 8.29 (1H, s). FABMS: 1100 (M+1), 1123 (M+Na).

Boc-Ala-(Prom)-Trp-Ala-Gly-Gly-Asp(OBzl)-OH (SEQ. ID NO. 15) (35):

Boc-Ala-(Prom)-Trp-Ala-Gly-Gly-Asp(OBzl)-OTce (SEQ. ID NO. 14) (34) (0.4 g, 3.6 mmol) is dissolved in 25 ml of glacial acetic acid (Aldrich) followed by addition of 4 g of Zn dust (Aldrich) in a 50 ml round bottom flask which is equipped with stirring bar. The reaction mixture is stirred for 24 h followed by dilution with acetic acid; the soluble material is filtered out. The filtrate is concentrated to give Boc-Ala-(Prom)-Trp-Ala-Gly-Gly-Asp(OBzl)-OH (SEQ. ID NO. 12) (35) and it is used in the next step without further purification.

Ala-(Prom)-Trp-Ala-Gly-Gly-Asp(OBzl)-OH (SEQ. ID NO. 16) (36):

The t-Boc group of 35 is deprotected by addition of Boc-Ala-(Prom)-Trp-Ala-Gly-Gly-Asp(OBzl)-OH (SEQ. ID NO. 15) (35) (0.34 g, 3.5 mmol) into 10 ml of 50% TFA in DCM in the presence of scavengers (2 g of phenol and 0.2 ml of ethanedithiol (Aldrich)) and the mixture stirred for 45 minutes. The DCM is evaporated under the hood and the residue is triturated with dry ether to give a solid. The solid is washed with dry ether and isolated by decantation. The solid of Ala-(Prom)-Trp-Ala-Gly-Gly-Asp(OBzl)-OH (SEQ. ID NO. 16) (36) is dried under reduced pressure. The product is purified further by a preparative reverse phase HPLC system using C-18 column using a gradient of solvent A: H$_2$O/Acetonitrile/0.1% TFA) and solvent B: Acetonitrile. $^1$H-NMR (CD$_3$OD): 7.54 (1H, d), 7.31 (6H, m), 7.10 (1H, m), 7.02 (1H, m), 6.98 (1H, b), 6.81 (1H, b), 6.58 (1H, b), 5.10 (2H, s), 4.83 (1H, t), 4.54 (1H, t), 4.37 (1H, m), 4.15 (1H, m), 3.88 (2H, b), 3.61 (2H, b, 1H), 3.17–2.89 (4H, m), 2.63 (2H, s), 2.43 (3H, s), 2.19 (3H, s), 1.71 (3H, d), 1.46 (6H, s), 1.21 (3H, d); FABMS: 870. (M+1).

Cyclic Hexapeptide Prodrug 1b:

A solution of 230 mg (0.90 mmol) BOP-Cl and 0.1 ml of triethyl amine in 50 ml of dichloromethane at 0° C. is stirred in an oven dried round bottom flask (250 ml) under dry argon. Then, 80 mg (0.09 mmol) linear peptide (36) and 0.18 ml (1.8 mmol) of NMM in 50 ml of DCM is added dropwise over 2 h into the previous mixture. After 3 days at room temperature, the solvent is evaporated and the residue dissolved in DCM (100 ml) followed by successive extraction with water, saturated solution of citric acid, water, 10% aqueous sodium bicarbonate, and water. The DCM layer is dried over anhydrous Na$_2$SO$_4$ and isolated by decantation. The DCM is evaporated to give cyclic peptide 24. The cyclic peptide 24 is analyzed by an analytical reverse phase HPLC (C-18 column, 25 cm×4.6 mm, 1 mL/min) using a gradient of solvent A: H$_2$O/5% acetonitrile/0.1% TFA and solvent B: Acetonitrile. The retention time of cyclic peptide 24 is at 13.5 minutes. 1H-NMR (CDCl$_3$): 6.5–7.76 (19H, m), 5.14 (2H, m), 4.82 (1H, m), 4.52 (1H, m), 4.38 (1H, m), 3.66–4.03 (5H, m), 2.88–3.11 (4H, m), 2.71 (1H, d), 2.51 (3H, s), 2.40 (1H, d), 2.17 (3H, s), 1.5–1.7 (9H, m), 1.13 (3H, d). FABMS: 852 (M+1). HRMS: Cal'd (M+1): 852.3932. Found: 852.3953.

Cyclic hexapeptide 24 is dissolved in 25 ml of absolute ethanol in a 50 ml round bottom flask equipped with stirring bar (Aldrich) followed by addition of 20 mg of 10% Pd-C (Aldrich). The reaction mixture is stirred under hydrogen gas atmosphere using a balloon filled with H$_2$. After 24 h, the reaction mixture is Pd-C catalyst was filtered and the filtrate concentrated to give a cyclic hexapeptide 1b. The crude product is purified by preparative reverse phase Rainin HPXL HPLC system using C-18 Dynamax-300A column, and a gradient (solvent A: H$_2$O/2.0 mM NH$_4$OAc and solvent B: acetonitrile; 10%–50% in 48 min). The cyclic peptide 1b is analyzed by an analytical reverse phase HPLC (C-18 column, 25 cm×3.6 mm, 1 mL/min) using a gradient of solvent A: H$_2$O/5% acetonitrile/0.1% TFA and solvent B: acetonitrile. The retention time of cyclic peptide 1b is at 10.9 minutes. $^1$H-NMR (CD$_3$OD): 6.59–7.51 (7H, m), 4.84 (1H, m), 4.40–4.62 (2H, m), 3.60–4.23 (5H, m), 2.78–3.20 (4H, m), 2.44 (1H, d), 2.36 (3H, s), 2.18 (3H, s), 2.04 (1H, d), 1.10–1.70 (12H, m). FABMS: 762 (M+1) and 784 (M+Na). HRMS: Cal'd (M+1), 762.3463, Found, 762.3481.

EXAMPLES 2–4

Synthesis of Cyclic Prodrugs of Opioid Peptides

In recent years, tremendous progress has been made in the design and synthesis of peptides with high selectivities for the different types ($\mu$, $\delta$, $\kappa$) of opioid receptors (Hruby et al., 1989; Schiller, 1991, 1993). However, a major obstacle to the development of these synthetic opioid peptides as clinically useful therapeutic agents has been their low permeability through biological barriers (e.g., intestinal mucosa, blood brain barrier) (Hruby et al., 1989; Schiller, 1991, 1993). Unfortunately, some of the structural features of opioid peptides (e.g., free N-terminal amino and C-terminal carboxyl groups and side chain carboxyl (e.g., Asp, Glu) and amino (e.g., Lys, Arg) groups) that bestow affinity and specificity of the molecule for the different receptor types also bestow on the molecules undesirable metabolic and physicochemical properties, which limit their membrane permeability (Hruby et al., 1989; Schiller, 1991, 1993).

The methodology described supra can be used to synthesize cyclic prodrugs of opioid peptides in order to transiently mask these undesirable metabolic and physicochemical properties, thereby enhancing their membrane permeability.

Permeability of opioid peptides across the intestinal mucosa can potentially occur via a paracellular route (pathway A, FIG. 1) or transcellular routes (pathways B, B' and C, FIG. 1).

Permeability of opioid peptides across the BBB can also potentially occur via a paracellular route (pathway A, FIG. 1) or transcellular routes (pathways B, B' and C, FIG. 1).

The methodology described herein can be used to prepare cyclic prodrugs of opioid peptides in order to alter their metabolic potential (e.g., substrate activity for aminopeptidase) and their physicochemical (e.g., charge, hydrogen bonding potential) properties, and thus their membrane permeability. Cyclic prodrugs of [Leu$^5$]-enkephalin (H-Tyr-Gly-Gly-Phe-Leu-OH) (SEQ. ID NO. 17) (100), a δ-selective opioid peptide which is readily metabolized in vivo (Hughes et al., 1975; Ehrenpreis et al., 1983; Schiller et al., 1985), can be prepared. The metabolic stability of these prodrugs of [Leu$^5$]-enkephalin can be assessed using purified enzymes and cell culture and perfused organ models of the intestinal mucosa and the BBB.

To evaluate the effects of this prodrug methodology on permeability, the present inventors have selected a number of synthetic opioid peptides that are metabolically stable, and that exhibit high affinity and high selectivity for opioid receptors. These opioid peptides include: (a) metabolically stable analogs of [Leu$^5$]-enkephalin (DADLE, H-Tyr-D-Ala-Gly-Phe-D-Leu-OH (SEQ. ID NO. 18) (101) (Bedded et al., 1977); H-Tyr-D-Ser(OtBu)-Gly-Phe-Leu-Thr (OtBu)-OH (SEQ. ID NO. 19) (102) (Gacel et al., 1988)); (b) a dermorphin analog (H-Tyr-D-Arg-Phe-Gly-OH) (SEQ. ID NO. 20) (103), that exhibits high affinity and high selectivity for μ receptors (Sasaki et al., 1985; Schiller, 1991); (c) δ-selective opioid receptor agonists (deltorphin, H-Tyr-D-Met-Phe-His-Leu-Met-Asp-NH$_2$ (SEQ. ID NO. 21) (108); deltorphin I, H-Tyr-D-Ala-Phe-Asp-Val-Val-Gly-NH$_2$ (SEQ. ID NO. 22) (109); deltorphin II, H-Tyr-D-Ala-Phe-Glu-Val-Val-Gly-NH$_2$) (SEQ. ID NO. 23) (110) (Kreil et al., 1989; Erspamer et al., 1989); and (d) a δ-selective opioid receptor antagonist (TIPP [ψ], H-Tyr-Ticψ [CH$_2$-NH]-Phe-Phe-OH) (111) (Schiller et al., 1993). The various cyclic prodrugs of these opioid peptides are illustrated in Schemes 12–17.

Scheme 12
Synthesis of cyclic prodrugs of [Leu]$^5$enkephalin 100 and DADLE 101

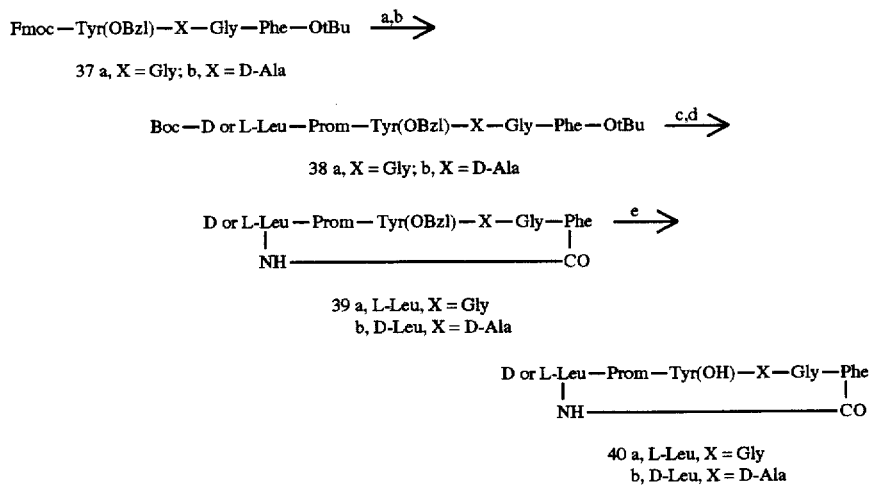

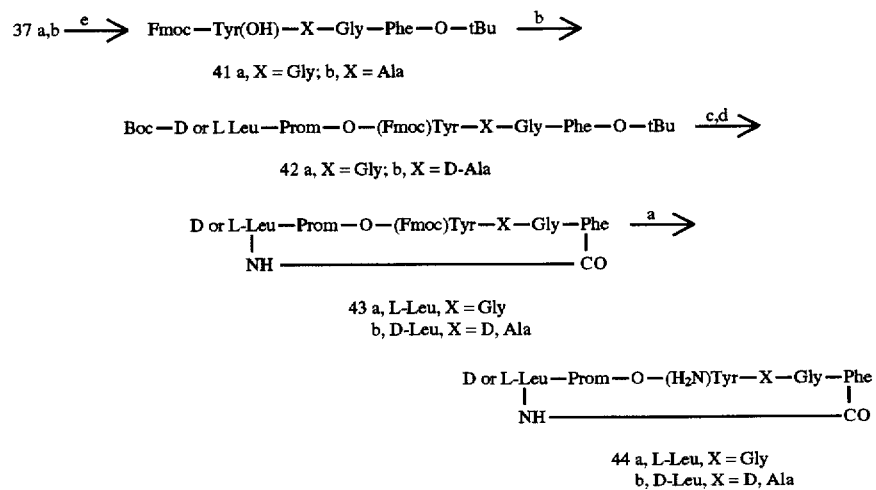

a) 50% DEA/DCM; b) 98a or b, DCC, HOBt; c) 50% TFA; d) BOP-Cl/TEA, DMF-DCM; e) H$_2$, Pd—C

-continued
Scheme 13
Synthesis of cyclic prodrugs of a metabolically stable enkephalin analog 102 a) C-terminal carboxyl to N-terminal amino linked cyclic prodrug of 102

Fmoc—Tyr(OP)—D-Ser(OtBu)—Gly—Phe—Leu—OBzl  $\xrightarrow{a,b}$ 45 (SEQ. ID NO. 24)

CBZ—Thr—(OtBu)—Prom—Tyr(OP)—D-Ser(OtBu)—Gly—Phe—Leu—OBzl  $\xrightarrow{c,d}$ 46 (SEQ. ID NO. 25)

Thr—(OtBu)—Prom—Tyr(OP)—D-Ser(OtBu)—Gly—Phe—Leu  $\xrightarrow{c}$
|                                                            |
NH ———————————————————————————— CO 47 (SEQ. ID NO. 26)

Thr—(OtBu)—Prom—Tyr(OH)—D-Ser(OtBu)—Gly—Phe—Leu
|                                                         |
NH ———————————————————————————— CO 48 (SEQ. ID NO. 27)

b) C-terminal carboxyl to Tyr hydroxyl linked cyclic prodrug of 102

Fmoc—Tyr(OH)—D-Ser(OtBu)—Gly—Phe—Leu—OBzl  $\xrightarrow{b}$ 49 (SEQ. ID NO. 24)

CBZ—Thr(OtBu)—Prom—O—(Fmoc)Tyr—D-Ser(OtBu)—Gly—Phe—Leu—OBzl  $\xrightarrow{c,d}$ 50 (SEQ. ID NO. 28)

Thr(OtBu)—Prom—O—(Fmoc)Tyr—D-Ser(OtBu)—Gly—Phe—Leu  $\xrightarrow{a}$
|                                                                 |
NH ———————————————————————————— CO 51 (SEQ. ID NO. 29)

Thr(OtBu)—Prom—O—(H$_2$N)—Tyr—D-Ser(OtBu)—Gly—Phe—Leu
|                                                                     |
NH ———————————————————————————— CO 52 (SEQ. ID NO. 30)

P = TBDMS
a) 50% DEA/DCM; b) 98c, DCC, HOBt; c) H$_2$, Pd—C; d) Bop-Cl/TEA,
DMF-DCM; e) Bu$_4$N$^+$F$^-$

Scheme 14
Synthesis of cyclic prodrugs of a μ selective dermorphin analog a) C-terminal carboxyl to N-terminal amino linked cyclic prodrug of 103

Fmoc—Tyr—(OBzl)—D-Arg(quinone)—Phe—OtBu  $\xrightarrow{a,b}$

53

Boc—Gly—Prom—Tyr—(OBzl)—D-Arg(quinone)—Phe—OtBu  $\xrightarrow{c,d}$

54

Gly—Prom—Tyr—(OBzl)—D-Arg(quinone)—Phe  $\xrightarrow{e}$
|                                                       |
NH ——————————————————————— CO

55

Gly—Prom—Tyr—D-Arg—Phe
|                                   |
NH ——————————— CO

56 b) C-terminal carboxyl to Tyr hydroxyl linked cyclic prodrug of 103

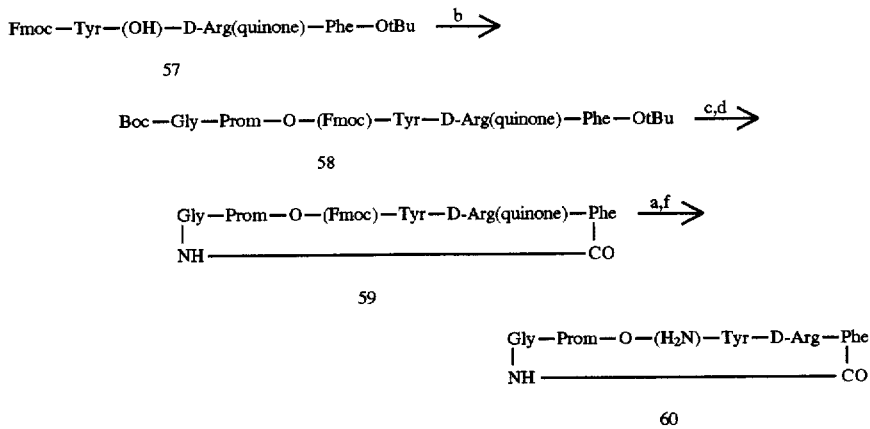

c) C-terminal carboxyl to Arg side chain amino linked cyclic prodrug of 103

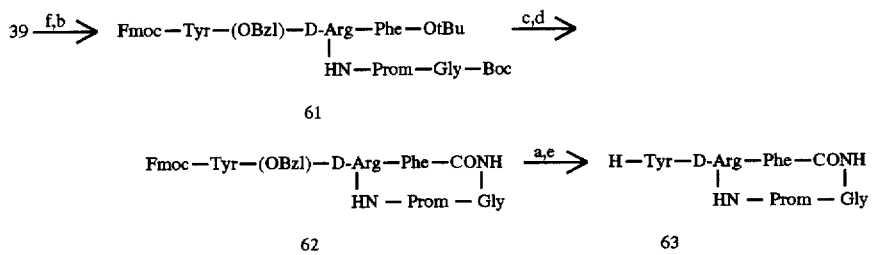

a) 50% DEA/DCM; b) 98d, DCC, HOBt; c) 50% TFA; d) BOP-Cl/TEA, DMF-DCM; e) $H_2$, Pd—C; f) $Na_2S_2O_4$.

Scheme 15
Synthesis of cyclic prodrugs of deltorphine 108 a) Asp β-carboxyl to N-terminal aminolinked cyclic prodrugs of 108

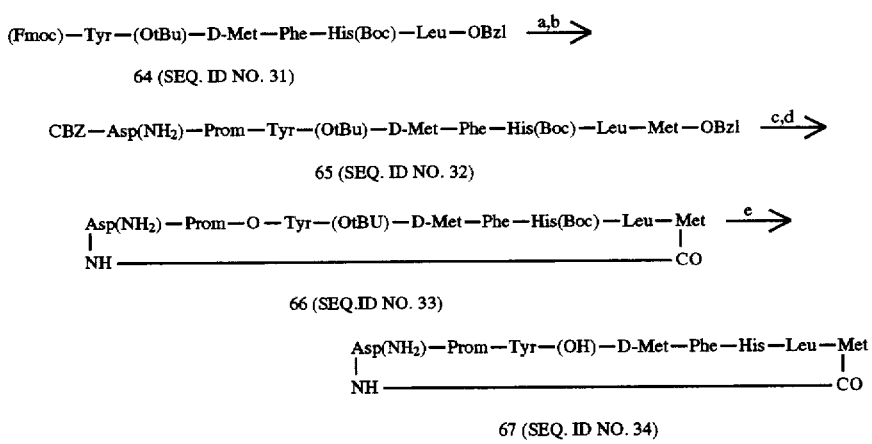

b) Asp β-carboxyl to Tyr hydroxyl linked cyclic prodrugs of 108

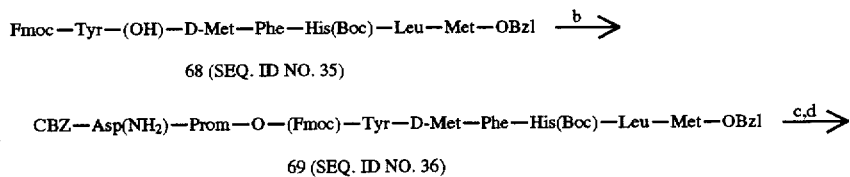

-continued

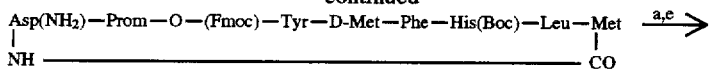
```
         |                                                          |
         NH ─────────────────────────────────────────────────────── CO
```
70 (SEQ. ID NO. 37)

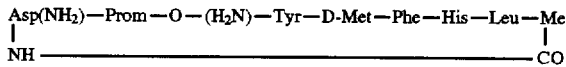
```
         |                                                      |
         NH ─────────────────────────────────────────────────── CO
```
71 (SEQ. ID NO. 38)

a) 50% DEA/DCM; b) 98e, DCC, HOBt; c) $H_2$, Pd—C; d) Bop-Cl/TEA, DMF-DCM; e) 50% TFA.

Scheme 16
Synthesis of cyclic prodrugs of deltorphine I (76) and II (80)

a) Asp β- or Glu γ-carboxyl to N-terminal amino linked cyclic prodrugs of 109 and 110

Fmoc—Tyr—(OBzl)—D-Ala—Phe—OtBu $\xrightarrow{a,b}$

72a X = Asp; b X = Glu

Boc—X—(OBzl)—Prom—Tyr—(OBzl)—D-Ala—Phe—OtBu $\xrightarrow{c,d}$

73a X = Asp; b X = Glu

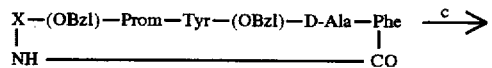
```
     |                                                   |
     NH ─────────────────────────────────────────────── CO
```
74a X = Asp; b X = Glu

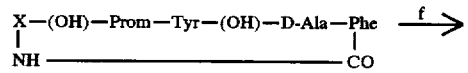
```
     |                                        |
     NH ──────────────────────────────────── CO
```
75a X = Asp; b X = Glu

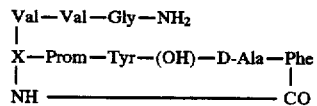
```
              Val—Val—Gly—NH_2
              |
              X—Prom—Tyr—(OH)—D-Ala—Phe
              |                        |
              NH ───────────────────── CO
```
76a X = Asp; b X = Glu b) Asp β- or Glu γ-carboxyl to Tyr hydroxyl linked cyclic prodrugs of 109 and 110

72 $\xrightarrow{e,b}$ Boc—X—(OBzl)—Prom—O—(Fmoc)—Tyr—D-Ala—Phe—OtBu $\xrightarrow{c,d}$ 77a X = Asp; b X = Glu

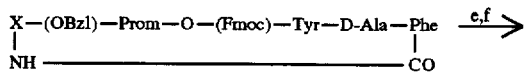
```
     |                                                      |
     NH ─────────────────────────────────────────────────── CO
```
78 a X = Asp; b X = Glu

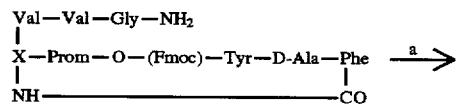
```
              Val—Val—Gly—NH_2
              |
              X—Prom—O—(Fmoc)—Tyr—D-Ala—Phe
              |                              |
              NH ─────────────────────────── CO
```
79a X = Asp; b X = Glu

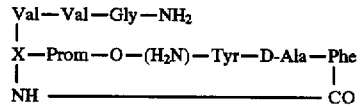
```
              Val—Val—Gly—NH_2
              |
              X—Prom—O—(H_2N)—Tyr—D-Ala—Phe
              |                              |
              NH ─────────────────────────── CO
```
80a X = Asp; b X = Glu a) 50% DEA/DCM; b) 98 for g. DCC, HOBt; c) 50% TFA; d) Bop-Cl/TEA, DMF-DCM; e) $H_2$, Pd—C; f) H—Val—Val—Gly—$NH_2$ (81), BOP, TEA.

-continued
Scheme 17 a) C-terminal carboxyl to N-terminal amino linked cyclic prodrug of 111

Boc—Tic—CHO $\xrightarrow{a,b}$ Fmoc—Tic—CHO $\xrightarrow{c}$
82                                83

Fmoc—TicΨ[CH$_2$NH]Phe—OtBu $\xrightarrow{d}$
84

Fmoc—TicΨ[CH$_2$NX]Phe—OtBu $\xrightarrow{e,f}$
85

Fmoc—Tyr(OBzl)—Tic(Ψ)[CH$_2$NX]—Phe—OtBu $\xrightarrow{e,g}$
86

Boc—Phe—Prom—Tyr(OBzl)—Tic(Ψ)[CH$_2$NX]—Phe—OtBu $\xrightarrow{h,i}$
87

Phe—Prom—Tyr(OBzl)—Tic(Ψ)[CH$_2$NX]—Phe
|                                                    |
NH ———————————————— CO $\xrightarrow{j}$
88

Phe—Prom—Tyr(OH)—Tic(Ψ)[CH$_2$NH]—Phe
|                                                  |
NH ———————————————— CO
89 b) C-terminal carboxyl to Tyr hydroxyl linked cyclic prodrug of 111

85 $\xrightarrow{e,k}$ Fmoc—Tyr(OP)—Tic(Ψ)[CH$_2$NX]—Phe—OtBu $\xrightarrow{l,g}$
90

Boc—Phe—Prom—O—(Fmoc)—Tyr—Tic(Ψ)[CH$_2$NX]—Phe—OtBu $\xrightarrow{h,i}$
91

Phe—Prom—O—(Fmoc)—Tyr—Tic(Ψ)[CH$_2$NX]—Phe
|                                                             |
NH ——————————————————— CO $\xrightarrow{e,j}$
92

Phe—Prom—O—(H$_2$N)—Tyr—Tic(Ψ)[CH$_2$NH]—Phe
|                                                             |
NH ——————————————————— CO
93 c) C-terminal carboxyl to the backbone amino linked cyclic prodrug of 111

81 $\xrightarrow{m,g}$ Fmoc—Tyr(OBzl)—Tic(Ψ)[CH$_2$N]—Phe—OtBu $\xrightarrow{h,i}$
                                                    |
                                                Prom—Phe—Boc
94

Fmoc—Tyr(OBzl)—Tic(Ψ)[CH$_2$N]—Ph———CO $\xrightarrow{e,j}$
                                              |              |
                                        Prom—Phe—NH
95

-continued

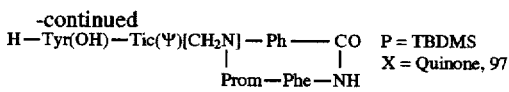

96 a) 50% TFA; b) Fmoc—Cl/TEA; c) H—Phe—OtBu, 1% HOAc, NaCNBH3;
d) 50, DCC/HOBt; e) 50% DEA/DCM; f) Fmoc—Tyr(OBzl)—OH,
DCC, HOBt; g) 98h, DCC HOBt; h) 50% TFA; i) BOP-Cl/TEA

Synthesis of Cyclic Prodrugs of Opioid Peptides

The synthetic approaches for the preparation of cyclic prodrugs of opioid peptides follows the strategy described above. First, the pro-moieties (Prom) with the appropriate amino acid attached (AA-Prom, 98a–h:

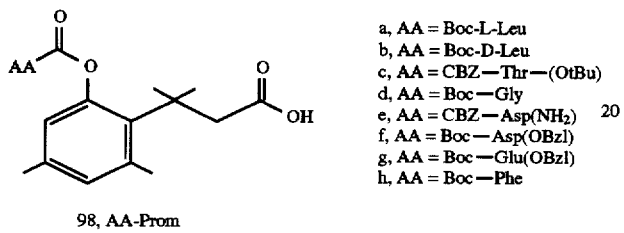

a, AA = Boc-L-Leu
b, AA = Boc-D-Leu
c, AA = CBZ—Thr—(OtBu)
d, AA = Boc—Gly
e, AA = CBZ—Asp(NH$_2$)
f, AA = Boc—Asp(OBzl)
g, AA = Boc—Glu(OBzl)
h, AA = Boc—Phe

98, AA-Prom are synthesized following the steps shown in Scheme 18.

Scheme 18
Synthesis of promoiety 98 with protected amino acid attached.

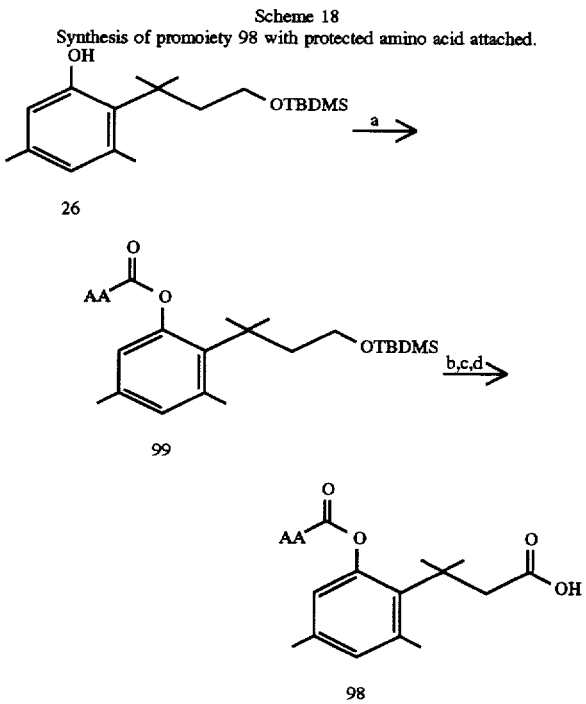

a. Boc-AA-pNP/DCM, DMAP, reflux, 80%; b. HOAc/THF/H$_2$O, 70%;
c. PCC, 70%; d. KMnO$_4$, 80%.

Second, linear peptides with the C-terminal carboxyl groups protected as esters are synthesized using standard solution phase methods employing Fmoc-protected amino acids (Stewart et al., 1984; Atherton et al., 1989). The appropriate AA-Prom conjugates (98a–h), which resemble N-protected amino acids, are then incorporated into the appropriate precursor peptide using solution phase approaches. The linear peptides containing the AA-Prom are then cyclized by conventional methods. Use of a solution phase approach allows for the most efficient use of the AA-Proms. If necessary, solid phase approaches using Wang's resin (Wang, 1973) or more acid-sensitive resins such as methoxy-alkoxybenzyl alcohol resin (Mergler et al., 1988) can be employed.

EXAMPLE 2

Synthesis of a Series of Cyclic Prodrugs of Metabolically Labile [Leu$^5$]-enkephalin (H-Tyr-Gly-Gly-Phe-Leu-OH, (SEQ. ID NO. 17) 100) and Metabolically Stable Analogs (DADLE, H-Tyr-D-Ala-Gly-Phe-D-Leu-OH, (SEQ. ID NO. 18) 101; H-Tyr-D-Ser(OtBu)-Gly-Phe-Leu-Thr(OtBu)-OH, (SEQ. ID NO. 19) 102) of [Leu$^5$]-enkephalin For all three of these peptides, cyclic prodrugs linked through the C-terminal carboxyl group to the N-terminal amino group (40a,b; 48) or to the Tyr hydroxyl group (44a,b; 52) (Schemes 12 and 13) are prepared.

The synthesis of the cyclic prodrugs 40a,b and 44a,b of [Leu$^5$]-enkephalin (100) and DADLE (101) follows similar strategies (Scheme 12). The synthesis of C-terminal carboxyl to N-terminal amino-linked cyclic prodrugs 40a and 40b is initiated by selective deprotection of the Fmoc-protected N-terminal amino groups of 37a and 37b using DEA followed by coupling with the appropriate AA-Prom 98a and 98b using DCC-HOBt to yield the linear peptides 38a and 38b, respectively (Scheme 12a). Deprotection of the Boc and t-butyl-protected amino and carboxyl groups of 38a and 38b followed by cyclization using BOP-Cl (Diago-Meseguer et al., 1980; Tung and Rich, 1985) yields the protected cyclic peptides 39a and 39b, respectively (Scheme 12a). Deprotection of 39a and 39b by catalytic hydrogenation affords the desired cyclic prodrugs 40a and 40b, respectively (Scheme 12a).

The synthesis of the C-terminal carboxyl to Tyr hydroxyl-linked prodrugs 44a and 44b is initiated from the Fmoc-protected peptides 37a,b (Scheme 12b). The first step is the deprotection of the benzyl group on Tyr by catalytic hydrogenation to yield 41a and 41b, respectively, followed by addition of the appropriate AA-Prom 98a and 98b to afford 42a and 42b, respectively (Scheme 12b). Deprotection of the Boc-amino group and t-butyl-carboxyl group of 42a and 42b followed by cyclization and deprotection yields the desired cyclic prodrugs 44a and 44b, respectively (Scheme 12b). Although the Fmoc protecting group is known to be unstable under certain hydrogenation conditions (Atherton et al., 1979), no stability problems with the Fmoc protecting group are encountered when hydrogenation reactions are carried out in methanol or ethanol.

Good results are obtained with the DCC/HOBt method for coupling AA-Prom to peptides. If problems are encountered with the DCC/HOBt method, other coupling approaches, including asymmetric (Jouin et al., 1987) or symmetric anhydrides, activated esters (Stewart et al., 1984; Atherton et al., 1989), BOP (Castro et al., 1975), BOP-Cl (Diago-Meseguer et al., 1980; Tung et al., 1985), and carbonyl diimidazole (Kamijo et al., 1984; Saha et al., 1989) can be employed.

The strategy for the synthesis of prodrugs 48 and 52 of the [leu⁵]enkephalin analog 102 (Scheme 13a,b) is very similar to the strategies for the preparation of the cyclic prodrugs 40a,b and 44a,b (Scheme 12a,b). However, due to the presence of a t-butyl group in the cyclic prodrugs 48 and 52, which is sensitive to TFA, hydrogenation-sensitive protecting groups are used for both the C-terminal carboxyl group of the starting peptides 45 and 49 and the N-terminal amino group of AA-Prom conjugate 98c. Another difference is that the Tyr hydroxyl group is protected with a silyl group, which can be prepared starting with Fmoc-Tyr-OBzl by reaction with TBDMSCl in the presence of imidazole at room temperature (Kendall et al., 1979; Ronald et al., 1982) followed by catalytic hydrogenation.

As an alternative to the use of the TBDMS protecting group, other protecting methods can be used to facilitate selective manipulation of the phenolic group. For example, the cyanomethyl group can be deprotected selectively using catalytic hydrogenation with PtO₂ as the catalyst without affecting benzyl protecting groups (Benarab et al., 1993). Furthermore, the levulinyl phenol protecting group can be selectively deprotected using sulfite ion-induced cleavage of the levulinyl group under neutral conditions, which does not cause any problems with respect to other protecting groups (Ono et al., 1988).

EXAMPLE 3

Synthesis of a Series of Cyclic Prodrugs of μ-selective Opioid Peptide H-Tyr-D-Arg-Phe-Gly-OH, 103 (SEQ. ID NO. 20)

For the μ-selective opioid peptide 103, cyclic prodrugs linked through the C-terminal carboxyl group to the N-terminal amino group (56), or to the Tyr hydroxyl group (60), or to the Arg side chain amino group (63) (Scheme 14) can be prepared. The overall strategies for the syntheses of these prodrugs of 103 are very similar to those outlined in Schemes 12 and 13 to prepare cyclic prodrugs of 100, 101, and 102.

One of the major problems associated with the synthesis of cyclic prodrugs of 103 is the types of groups commonly used to protect the Arg side chain. The currently available protecting groups for Arg (e.g., nitro and toluenesulfonyl) are too stable, and the conditions needed to remove them likely cause the degradation of the pro-moiety. A novel redox-sensitive group for protecting amines and alcohols has been developed (Wang et al., 1993; Wang et al., 1995). This protecting strategy, which is illustrated in Scheme 19, employs a facile lactonization system involving a quinone derivative which can be cleaved under mild reductive conditions (Na₂S₂O₄ solution or stronger reducing conditions).

Scheme 19
Development of a redox-sensitive amine protecting group.

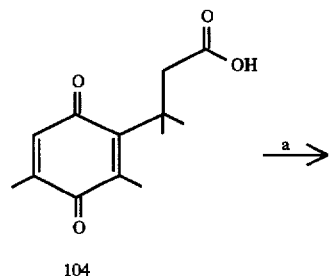

104

-continued
Scheme 19
Development of a redox-sensitive amine protecting group.

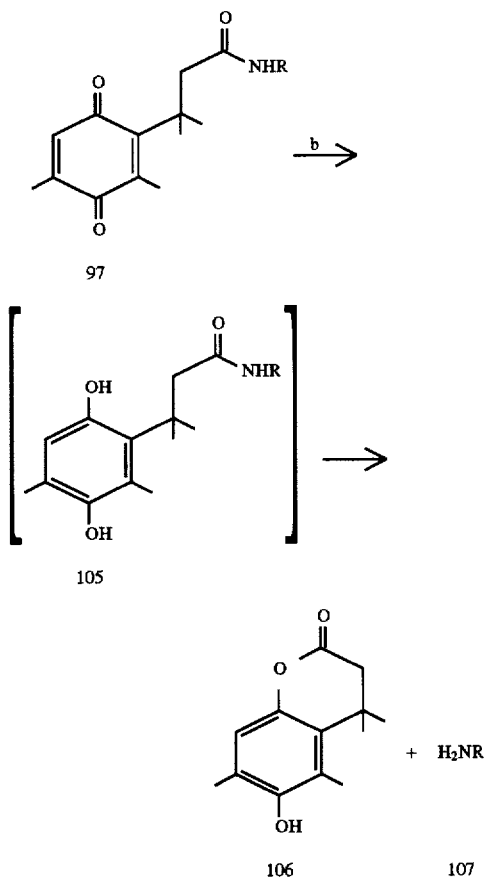

a) DCC/HOBt, NH₂R; b) Na₂S₂O₄

Use of this unique protecting group on Arg side chain groups, which allows manipulation of various functional groups on 103 and the AA-Prom conjugate 98d, facilitates the synthesis of the cyclic prodrugs 56, 60 and 63 by the strategies outlined in Scheme 14. For the preparation of 63, which involves the reaction of the Arg side chain for the formation of the cyclic structure, the second reactive amino group of the. Arg side chain can be protected using CBZ, which can be cleaved at the end using catalytic hydrogenation. Such selective protection poses no problem in view of the significant reactivity differences between the two amino groups of the Arg side chain.

EXAMPLE 4

Synthesis of a Series of Cyclic Prodrugs of the δ-selective Opioid Receptor Agonists deltorphin, H-Tyr-D-Met-Phe-His-Leu-Asp-NH₂, (SEQ. ID NO. 21) 108; deltorphin I, Tyr-D-Ala-Phe-Asp-Val-Val-Gly-NH₂, (SEQ. ID NO. 22) 109; deltorphin II, H-Tyr-D-Ala-Phe-Glu-Val-Val-Gly-NH₂, (SEQ. ID NO. 23) 110; and the δ-Selective Opioid Receptor Antagonist TIPP(ψ), H-Tyr-Ticψ[CH₂NH]-Phe-Phe-OH, (SEQ. ID NO. 39) 111

The δ-selective opioid receptor agonists deltorphin (108), deltorphin I (109,) and deltorphin II (110) are prepared as cyclic prodrugs linked through the side chain carboxyl groups of Asp or Glu to the N-terminal amino groups (67, 76a,b), or to the Tyr hydroxyl group (71, 80a,b) (Schemes 15 and 16).

The strategies for synthesis of the cyclic prodrugs 67, 71, 76a,b and 80a,b of deltorphin (108), deltorphin I (109), and deltorphin II (110) are very similar to the strategies shown in Schemes 12 and 13 to prepare cyclic prodrugs of 100, 101, and 102. The only significant differences are that the AA-Prom conjugates employed in these synthetic schemes are 98e, 98f, and 98 g. In addition, for the synthesis of the deltorphin cyclic prodrugs 67 and 71, the C-terminal carboxyl group is temporarily protected as a benzyl ester because the His side chain is Boc protected (Scheme 15).

The δ-selective opioid receptor antagonist TIPP(ψ) (111) is prepared as cyclic prodrugs linked through the C-terminal carboxyl group to the N-terminal amino group (89), or the Tyr hydroxyl group (93), or the backbone secondary amino group (96).

Again, the synthetic strategies for the cyclic prodrugs 89, 93, and 96 of TIPP(ψ) (111) are very similar to the strategies shown in Schemes 12 and 13 for the preparation of cyclic prodrugs of 100, 101 and 102. The only significant differences are the need to synthesize Fmoc-Tic aldehyde (83), which can be accomplished using literature procedures (Schiller et al., 1993, Feherentz et al., 1983), and the utilization of AA-Prom conjugates 98 h. In addition, the N-protection of the Tic aldehyde is changed to Fmoc to ensure selective protection/deprotection of the functional groups during the synthesis. The reductive amination of Fmoc-Tic aldehyde (Tic=1,2,3,4-tetrahydroisoquinoline-3-carboxylic acid) can be carried out by literature procedures (Sasaki et al., 1987) to give 84, and the free secondary amino group can be protected by the redox sensitive quinone protecting group as illustrated in Scheme 19.

BIOLOGICAL EVALUATION

The novel cyclic prodrugs synthesized as described above can be evaluated both in vitro and in vivo using standard techniques. Because of the nature of the chemical modifications involved in the present prodrug methodology (e.g., derivatization of the N-terminal end of the peptides), these cyclic prodrugs will probably be devoid of receptor binding activity. However, these cyclic prodrugs should be hydrolyzable by esterases, thereby regenerating the pharmacologically active peptides. The bioreversibility of these cyclic prodrugs and their receptor binding potential can be evaluated using purified enzymes and through pharmacological testing. In order to accurately measure the permeability properties of these cyclic prodrugs, sensitive and selective analytical methods for the peptides and for the cyclic prodrugs can be employed. To study the permeability of these cyclic prodrugs of peptides across membranes (such as the intestinal mucosa and the blood brain barrier (BBB), both in vitro cell culture models and in situ perfused organ models can be employed.

The following types of studies are preferred to evaluate the characteristics of the cyclic prodrugs.

1. Receptor Binding Assays

These assays evaluate the ability of the prodrugs, and the linear peptides, to bind to the respective receptors. Radio labelled ligand binding assays provide an in vitro evaluation and response tests provide an in vivo evaluation.

2. Chemical and Enzymatic Stability Tests

These tests are utilized to evaluate the stability of the cyclic prodrugs, as well as their bioreversibility to produce the corresponding biologically active linear peptide. Thus, both proteolytic degradation studies and esterase tests are utilized.

3. Membrane Permeability Studies

These tests evaluate the ability of the cyclic prodrugs to permeate the relevant biological membranes. As examples, described further herein are tests utilizing Caco-2 cells, BBMEC monolayers, blood brain barrier (BBB) using a rat brain model, and a rat ileum transport study.

1. Receptor Binding Assays

Radioligand binding assays, using mouse brain membranes, are employed to evaluate the affinity of these molecules at opioid μ, δ, and κ receptors. Such studies allow comparison of affinity at these sites with a large database of pharmacological standards. As prodrugs, these compounds should not have significant affinity at these receptor sites. Evaluations are made using routine competitive binding assays (Wild et al., 1993).

1.1 Radiolabeled Ligands

For opioid μ receptors, the antagonist [$^3$H]-CTOP (New England Nuclear, S.A.=84.2 Ci/mmol) is employed. The affinity ($K_d$=160 pM) of [$^3$H]-CTOP for the μ opioid receptor is 32,500 times greater than at the δ receptor. [$^3$H]-CTOP is used at a concentration of 0.5 nM to label μ opioid receptors, and requires an incubation period of 120 min at 25° C. to reach equilibrium. For opioid δ receptors, the antagonist [$^3$H]-naltrindo ([$^3$H]-NTI, New England Nuclear, S.A.= 20–40 Ci/mmol) is employed. [$^3$H]-NTI is the most selective antagonist radioligand currently available for labeling the δ receptor. Inhibition studies against this radioligand are performed at a concentration of 0.15 nM, which requires an incubation time of 3 hr to reach equilibrium at 25° C. Like [$^3$H]-CTOP, [$^3$H]-NTI is particularly useful because it is an antagonist. Thus, concerns about receptor affinity states are eliminated. For opioid κ receptors, [$^3$H]-U69,593 is employed (New England Nuclear, S.A.=30–60 Ci/mmol). [$^3$H]-U69,593 is highly selective for the κ receptor ($K_d$=1 nM) with κ:μ and κ:δ affinity ratios of 236:1 and 607:1, respectively. Inhibition studies with [$^3$H]-U69,593 can employ a concentration of 2 nM and an incubation period of 1 hr at 25° C. to achieve equilibrium binding.

1.2 Assay Conditions

Mouse brain membranes are prepared as previously described (Wild et al., 1993), and are suspended to a final concentration of 10% (w/v) in 50 mM Tris buffer at pH 7.4. All other components (e.g., radioligand, test compound, etc.) of the incubates are prepared in an assay buffer consisting of 1.0 mg/ml bovine serum albumin in 50 mM Tris at pH 7.4 and containing the following protease inhibitors: 100 mM bestatin, 1.0 mM thiorphan, 1.0 mM captopril, and 100 mM Leu-Arg. At the concentrations listed, these inhibitors do not affect the binding of the radioligands used. Hydrolysis of the cyclic prodrugs of the opioid peptides by esterases in the mouse membrane preparations are checked prior to conducting binding studies by monitoring the stability of the cyclic prodrugs in this tissue preparation by RPLC methodology. If stability of the cyclic prodrugs is problematic, the membrane preparations are treated with an esterase inhibitor (e.g., diisopropylfluorophosphate, DFP). Whether this treatment has any adverse effects on the binding of the μ, δ, and κ radioligands can also be determined. Each of the novel compounds are assayed 2–3 times against μ, δ, and κ radioligands. Each analog is tested at 10 concentrations in duplicate with duplicate total binding (no inhibitor) and nonspecific binding (10 mM naloxone) samples included. The analogs are be tested initially over a broad concentration range of 0.1 to 3,000 nM to assess affinity. Subsequent assay(s) is/are performed over a narrower (100-fold) concentration range centered on the estimated $IC_{50}$ value for each of the radioligands, unless multiple site interactions are observed. All assays for each of the test compounds are performed on different days using fresh dilutions. Incubations are terminated by rapid filtration through Whatman GF/B filter strips previously soaked in 0.1% polyethylenimine for at least 0.5 hr. The filtered membranes are washed three times with 4 ml of ice-cold 0.9% saline, and radioactivity is measured using a liquid scintillation counter with >42% efficiency.

1.3 Data Analysis

Radioligand binding inhibition data are analyzed using a microcomputer and MINSQ, a non-linear curve-fitting package that utilizes nonlinear regression analysis based on 1 or 2 independent site models. Improvement in fit from multiple-site analysis is determined by the F-ratio test. Pseudo-Hill slope values for one site models are obtained by nonlinear regression analysis based on the logistic equation. Saturation binding data are processed by an analogous approach.

$IC_{50}$ values of ligands can be related to their inhibition constants ($K_i$) through the Cheng-Prusoff relationship: $K_i = [IC_{50}]/(1+[L]/K_d)$, where $K_d$ and $[L]$ are the dissociation constant and free concentration of the radioligand used, respectively. This relationship is only valid when the $K_d$ used for the radioligand represents its value under the experimental conditions of the assay.

1.4 Tests of Antinociception

For in vivo evaluation, antinociceptive responses are determined in separate groups of mice in the warm-water tail-flick test using water at 50°, 52° or 55° C. as the noxious stimulus, or in the hot-plate test with the temperature of the surface set at 50°, 52° or 55° C. as the noxious stimulus (Horan et al., 1993; Vanderah et al., 1992). In the tail-flick test, the latency to the first sign of a rapid tail-flick can be taken as the endpoint. Prior to agonist administration, the tail of each mouse is immersed in the water and the latency to a rapid flick recorded (control latency). Animals having a control latency of greater than 5 sec are eliminated from the study. In the hot-plate test, the latency to the first sign of hind-paw lick or escape attempt is taken as the endpoint. Prior to agonist administration, a control latency is determined for each mouse. Animals having a control latency of greater than 10 sec are eliminated from the study.

The procedure to determine response latency is repeated at various times after systemic (i.e., ip or iv) administration of the test compound to determine a time of peak effect; this time of peak effect is used for the construction of the dose-effect relationship for that analog. Following administration of the test compounds, animals that do not flick their tails within 15 sec (cut-off time), or demonstrate a hind-paw lick/escape attempt within 60 sec (cut-off time), are removed from the nociceptive stimulus to avoid tissue damage, and assigned a maximal antinociceptive score of 100%. Antinociception is expressed as: % antinociception=100×(test latency−control latency)/(cut-off time−control latency). All testing is conducted in unanesthetized mice.

2. Chemical and Enzymatic Stability Tests

The prodrugs described herein are designed to be hydrolyzed by esterases, ultimately releasing the linear peptide. The ability of the cyclic prodrugs to release the corresponding linear peptide can, therefore, be evaluated in vitro. For example, the esterase-catalyzed release of the DSIP analog (Trp-Ala-Gly-Gly-Asp-Ala) (SEQ. ID NO. 1) from the cyclic prodrugs 1a and 1b and the opioid peptides (100–102, 103, 108–111) from the various cyclic prodrugs (40a,b, 44a,b, 48, 52, 56, 60, 63, 67, 71, 76a,b, 80a,b, 89, 90, 96) is studied using commercially available (Sigma Chemical Co.) porcine liver esterase and rat and human blood. These stability studies are carried out in 0.05M phosphate buffer, pH 7.4, at 37° C. via published protocols (Amsberry et al., 1991). The chemical stability of these cyclic prodrugs can also be studied using identical conditions, except in the absence of esterase or blood. The disappearance of the cyclic prodrugs and the appearance of the linear peptides is monitored by RPLC employing UV or fluorescence detection methods.

When the stability of the cyclic prodrugs 1a and 1b were determined in rat and human blood and compared to the chemical stability of these prodrugs, evidence for esterase catalyzed degradation of 1a and 1b to the DSIP analog, Trp-Ala-Gly-Gly-Asp-Ala, (SEQ. ID NO. 1) was obtained. The half-lifes of chemical stability ($T_{1/2}$) of 1a and 1b in HBSS (pH 7.4) were determined to be 208 min. and 764 min., respectively. Both of these prodrugs degraded completely to the DSIP analog, Trp-Ala-Gly-Gly-Asp-Ala (SEQ. ID NO. 1). However, when these prodrugs were incubated in human blood, the $T_{1/2}$ were determined to be substantially shorter ($T_{1/2}$=99 min., 1a; $T_{1/2}$=173 min., 1b). Similar results were observed when rat blood was used ($T_{1/2}$=111 min., 1a; $T_{1/2}$=173 min., 1b). These results show that in the presences of rat or human blood, which are known to contain esterases, these cyclic prodrugs degrade at rates 2–4 times faster than their chemical degradation rates which were determined under identical experimental conditions.

3. Membrane Permeability Studies

For a peptide to permeate a biological barrier (e.g., intestinal mucosa, BBB) by passive diffusion (FIG. 1, pathway B), it must exhibit certain optimal physicochemical characteristics with respect to its charge, size, lipophilicity, hydrogen bonding potential, and solution conformation (Burton et al., 1991; Gray et al., 1994). Since the primary effects of converting these linear peptides into cyclic prodrugs is to "mask" charged residues (e.g., N-terminal amino and C-terminal carboxyl groups), and to "mask" potential hydrogen bonding sites (e.g., Ser hydroxyl group), these changes can be quantified by measuring partition coefficients of the linear and cyclic prodrugs. In addition, the cyclic prodrugs of the linear peptides have restricted conformational freedom, which may generate unique solution structures different from those observed in the linear peptide. The solution conformations of the linear peptides and their cyclic prodrugs can be determined by 2-D NMR and molecular modeling.

3.1 Caco-2 Cell Studies

One intestinal model which is employed herein, which was pioneered in the inventors' laboratory in the late 1980s, consists of human colon carcinoma cells (Caco-2) grown onto microporous membranes (Hidalgo et al., 1989). This cell line, which readily forms highly polarized cell monolayers, has been shown by many academic and industrial laboratories worldwide to be an accurate in vitro model of the intestinal mucosa and very useful for conducting drug transport and drug metabolism studies (Artursson, 1990; Hilgers et al., 1990; Wilson et al., 1990; Borchardt et al., 1991; Rubas et al., 1993). This model can be effectively used to study passive diffusion of peptides (FIG. 1, pathway B) (Burton et al., 1991, 1992, 1993; Conradi et al., 1991, 1992; Kim et al., 1993a) and passive diffusion of peptides modified by the apically polarized efflux mechanism (FIG. 1, pathway B') (Burton et al., 1993).

The Caco-2 cells are grown under conditions similar to those reported previously (Hidalgo et al., 1989). Briefly, the Caco-2 cells are plated at a density of 6–7×10³cells/cm² on Transwell™ polycarbonate membranes which have been coated with rat tail collagen. The Caco-2 cells are maintained at 37° C. in DMEM medium (Hidalgo et al., 1989) in an atmosphere of 5% $CO_2$ and 90% relative humidity. The media (1.5 ml in the insert and 2.5 ml in the well) are changed daily. Caco-2 cells approximately 15–18 days old with TEER values of 300–400 Wcm² can be used for transport studies. The integrity of the monolayers is also monitored in random samples of Caco-2 cell monolayers by assessing the AP-to-BL flux of [³H]-PEG (Kim et al., 1993a,b). Cells 15–18 days old are used for these transport studies because a) confluence monolayers have formed (Hidalgo et al., 1989) and b) the cells express the apically polarized efflux mechanism (Burton et al., 1993).

Before transport studies are initiated, the Caco-2 cell monolayers are washed twice with transport medium (HBSS) prewarmed at 37° C. (Hidalgo et al., 1989). Cell monolayers are then be equilibrated at 37° C. for 30 min before undertaking transport studies. In AP-to-BL transport studies, 1.5 ml of transport medium containing the test compound (approx. 100 mM, depending on solubility) are be added to the AP side and 2.5 ml of a transport medium without test compound are added to the BL side. In BL-to-AP transport studies, 2.5 ml of a transport medium continuing the test compound are added to the BL side and 1.5 ml of a transport medium without the test compound are added to the AP side. Aliquots (50 ml) are removed from the AP and BL sides at selected times (0, 10, 20, 30, 60 min). Since the total sampling volume is negligible (<3% of the total volume), the $P_{app}$ values are not corrected for the dilution effect. At the end of the transport experiments, the Caco-2 cell monolayers are washed once with ice-cold transport medium, the cell monolayers are removed by treatment with tissue dissolving agent, and the total amount of protein is determined by using the method of Lowry et al., (1951).

From the experiments described above, a monolayer permeability coefficient ($P_{monolayer}$) is calculated for each linear peptide and each cyclic prodrug. Experiments can then be conducted to determine if the flux of the peptide and the cyclic prodrug is via passive diffusion, passive diffusion modified by the apically polarized efflux mechanism or passive diffusion modified by metabolism.

The passive diffusion pathway (FIG. 1, pathway B) and the passive diffusion pathway modified by the apically polarized efflux mechanism (FIG. 1, pathway B') can be differentiated based on the studies of Burton et al.

Calculation of Permeability Coefficients

The apparent permeability coefficients ($P_{app:cell}$) for the peptides and their cyclic prodrugs across Caco-2 cell monolayers grown on Transwell™ collagen-coated polycarbonate membranes are calculated according to the following equation: $P_{app:cell}$=flux$_{monolayer}$×1/A×1/C, where C is the initial peptide concentration in the AP side (pmol/mL), A is the surface area of the Transwell™ (cm²), and flux$_{monolayer}$ is the steady-state rate of appearance of apically applied peptide in the BL side of the monolayers (pmol/sec) after the initial lag time. $P_{app:cell}$ reflects the permeability of the peptide through the aqueous boundary layer adjacent to the surface of the cell monolayer ($P_{ABL:cell}$), across the cell monolayer ($P_{monolayer}$), through the collagen-coated polycarbonate membrane ($P_{filter}$), and through the aqueous boundary layer adjacent to the bottom surface of the polycarbonate membrane ($P_{ABL:membrane}$). The effect of $P_{ABL:cell}$, $P_{ABL:filter}$ and $P_{filter}$ on the $P_{app:cell}$ can be estimated by conducting transport experiments through blank (no cell monolayer) Transwell™ polycarbonate membranes (Ho et al., 1994). Thus, "true" $P_{monolayer}$ values can be determined for each peptide and each cyclic prodrug (Chikhale et al., 1994).

Comparison of the Permeability of Linear and Cyclic Peptides

To evaluate the cellular permeability characteristics of the cyclic prodrugs 1a and 1b as compared to the DSIP analog, Trp-Ala-Gly-Gly-Asp-Ala, (SEQ. ID NO. 1) the following experiments were conducted in the Caco-2 cell culture system.

When the hexapeptide, Trp-Ala-Gly-Gly-Asp-Ala, (SEQ. ID NO. 1) was added to the AP side of a Caco-2 monolayer, it was rapidly metabolized resulting in only 0.8±0.1% remaining after a 120 min. incubation. In the absence or in the presences of protease inhibitors (bestatin, diprotin, captopril), which stabilize the peptide to proteolytic degradation, no detectable quantities of the Trp-Ala-Gly-Gly-Asp-Ala (SEQ. ID NO. 1) were observed on the BL side of the monolayer. These results illustrate that even when the peptide is stabilized to enzyme degradation, it does not have the optimal physicochemical properties to allow it to permeate the cell monolayer. If this hexapeptide is N-terminally acetylated and C-terminally amidated (Ac-Trp-Ala-Gly-Gly-Asp-Ala-$NH_2$(SEQ. ID NO. 40)), it was substantially more stable (75.8±4.0% remaining after 180 min. incubation) when applied to the AP side of Caco-2 cells. This type of chemical modification, which neutralized the charges on the N-terminal ($-NH_3^+$) and C-terminal ($-CO_2^-$) ends of the peptide, did sufficiently change its physicochemical properties; thus, flux of the peptide to the BL side of the monolayer was detected ($P_{app}$=2.1±0.5×10⁻⁸ cm/sec.). However, it should be noted that this type of chemical modification will not be bioreversible and, thus, will not generate the parent peptide, Trp-Ala-Gly-Gly-Asp-Ala (SEQ. ID NO. 1).

When the prodrugs 1a and 1b, which are bioreversible prodrugs of this hexapeptide, were applied to the AP side of the Caco-2 monolayer, substantially higher permeability values were observed (1a, $P_{app}$=1.17±0.11×10⁻⁷ cm/sec.; 1b, $P_{app}$=1.21±0.36×10⁻⁷ cm/sec.). If these permeability values for the prodrug 1a and 1b are compared to the permeability value of the capped hexapeptide (Ac-Trp-Ala-Gly-Gly-Asp-Ala-$NH_2$(SEQ. ID NO. 40), this represents a 5–6 fold increase in permeability. Similar comparisons cannot be made with the native peptide, because it was totally impermeable to the Caco-2 cell monolayer.

3.2 Rat Ileum Transport Studies—Perfused Rat Ileum Model

An in situ model of the intestinal mucosa which consists of a perfused segment of a rat ileum with the mesenteric vein being cannulated (Buttleworth et al., 1973; Kim et al., 1993a,b) can also be employed herein. This in situ model allows one to measure simultaneously the disappearance of a peptide from the intestinal lumen and its appearance in the blood.

Cannulation of the jugular vein, the ileum, and the mesenteric vein of male Sprague-Dawley rats (300-350 g) can be accomplished sequentially using a modification (Kim et al., 1993a,b) of a published method (Buttleworth et al., 1973). Briefly, the rats are anesthetized with sodium pentobarbital. A cannula is inserted into the jugular vein for the blood supply from a donor rat. A longitudinal midline incision is made in the abdomen of the rat and the distal site of the small intestine (ileum) at 20 cm above the beginning of the colon is cannulated with an L-shaped glass cannula. Prewarmed (37° C.) buffer (HBSS, pH 7.4, containing 25 mM glucose and 10 mM HEPES) is perfused through the cannulated ileum using a positive displacement minipump.

The mesenteric vein coming from the ligated intestinal loop is isolated by careful blunt dissection. A specially designed mesenteric vein cannula attached to polyethylene tubing (filled with heparinized saline solution) is inserted into the mesenteric vein. The animal is heparinized by i.v. administration of a heparin solution into the femoral vein. Within 1 min after the cannulation of mesenteric vein, freshly drawn heparinized rat blood is infused into the jugular vein of the rat using a constant infusion pump to replenish the blood lost through the mesenteric vein (Kim et al., 1993a).

In a typical transport experiment (Kim et al., 1993a,b), the rat ileum is perfused in a recirculation mode by using a minipump. Solutions of the peptide or the cyclic prodrug (approx. 200 mM, depending on solubility) are injected into the recirculating perfusate through an in-line tee containing an injection port with a teflon-faced septum. Samples of the intestinal perfusate are collected from the tubing located in front of the perfused ileum at 2, 4, 7, 10, 15, 20 and 30 min, while simultaneously collecting blood from the mesenteric vein cannula in separate containers. The perfusate flow rate is maintained at 2.5 ml/min. At the end of the collection period, the blood samples are centrifuged for 3 min at 3000 rpm to provide the plasma fraction. The peptide and/or cyclic prodrug concentrations are determined using the analytical methodology described above.

Similar to the studies in the Caco-2 cell culture system, the pathway of flux (passive, passive modified by an apically polarized efflux mechanism) can be elucidated by determining the effects of the solute concentration and verapamil (a known inhibitor of p-glycoprotein) on the flux of the peptide.

Calculation of Permeability Coefficients

To calculate the permeability of the peptides or the cyclic prodrugs in the perfused rat ileum model, a compartment model can be employed (Kim et al., 1993a). This model is used to calculate $CL_{app}$, which is the apparent clearance of the model peptide across the perfused ileum. To compare the membrane permeability of the model peptides between the perfused rat ileum and Caco-2 systems, an apparent permeability coefficient ($P_{app}$) is calculated from the $CL_{app}$ by knowing the effective surface area of the perfused rat ileum (Kim et al., 1993a).

3.3 Blood Brain Barrier (BBB) Studies

Similar to the approach used to study the permeability of solutes across the intestinal mucosa, the permeability of the linear peptides and their cyclic prodrugs across the BBB can be studied employing both an in vitro cell culture system and an in situ brain perfusion model. This cell culture model of the BBB consists of primary cultures of brain microvessel endothelial cells (BMECs) grown onto microporous membranes (e.g., polycarbonate) (Audus et al., 1986a; Miller et al., 1992; Ng et al., 1994). This cell culture system, which readily forms highly polarized cell monolayers, has been shown by many academic and industrial laboratories worldwide to be an accurate model of the BBB and very useful for conducting in vitro drug transport and drug metabolism studies (Audus et al., 1990; Takakura et al., 1992). This model was selected because it can be effectively used to study passive diffusion of peptides (Chikhale et al., 1994) and passive diffusion of peptide mimetics modified by the apically polarized efflux mechanism. An in situ rat brain perfusion model can be employed to confirm the in vitro cell culture data.

The general strategy for determining the BBB permeability properties of the linear peptides and their cyclic prodrugs is as follows. The permeability properties of all of the linear peptides and their cyclic prodrugs is evaluated using the BMEC culture model of the BBB (Miller et al., 1992; Ng et al., 1994). Since this is an in vitro cell culture model which employs simple transport buffers, less sophisticated analytical methodology can be employed to measure the disappearance of the peptide or the cyclic prodrug from the AP chamber and the appearance of the peptide or the cyclic prodrug in the BL chamber. In addition, this cell culture model of the BBB has been employed to evaluate the permeability of peptides, and the permeability data correlate well with permeability data generated using a perfused rat brain model (Chikhale et al., 1994). This same BMEC model has been used by Tsuji et al. (1992) to identify the p-glycoprotein responsible for the apically polarized efflux mechanism in the BBB.

Following is a description of the procedures employed to carry out the in vitro cell culture experiments and the in situ perfused brain experiments.

BMEC Cell Culture Model Isolation and Culturing of BMECs

The BMECs are isolated from cerebral gray matter of fresh bovine brains following the procedure described by Audus et al. (1986a) with a slight modification which substantially increases the tightness of the cell monolayers (Ng et al., 1994). Approximately $2.5 \times 10^5$ BMECs are seeded on Transwell™ polycarbonate membranes, which are precoated with type I collagen and bovine fibronectin. The cells are grown at 37° C. with 95% humidity and 5% $CO_2$ in culture medium which consists of modified Eagle medium (MEM):F12 (1:1) supplemented with heat-inactivated horse serum and heparin. After 10 days of culturing, the BMECs are treated with culture medium containing 8-(4-chlorophenylthio) cAMP and RO20-1724, a phosphodiesterase inhibitor, for 1-2 days, and then used for transendothelial cell transport experiments. Monolayer integrity is assessed by measuring the permeability of a paracellular marker (e.g., [$^3$H]-sucrose) and/or by measuring TEER values (Chikhale et al., 1994; Ng et al., 1994).

BMEC Transport Studies

Before transport studies are initiated, BMECs are preincubated with the transport medium (HEPES buffer, pH 7.4, containing NaCl, $NaHCO_3$, glucose, KCl, $MgSO_4$, $K_2HPO_4$, $CaCl_2$, 3-(4-chlorophenylthio) cAMP and RO20-1724) at 37° C. for 30 min. The medium is removed by aspiration and replaced with fresh transport medium on the BL side (2.5 ml) To start the transport experiment, 1.5 ml of transport medium containing the test compound are added to the AP chamber. Aliquots (50 ml) are removed from the BL and/or AP sides of the monolayer at selected times (e.g., 0, 10, 20, 30, 60 min). Since the total sampling volume is negligible (<3% of the total volume), the $P_{app}$ values are not corrected for the dilution effect.

From the experiments described above, a monolayer permeability coefficient ($P_{monolayer}$) is calculated for each peptide and each cyclic prodrug. Experiments are then conducted to determine if the flux of the peptide is via passive diffusion or passive diffusion modified by the apically polarized efflux pathway. The approaches used to differentiate the passive diffusion pathway (FIG. 1, pathway B) and the passive diffusion pathway modified by the apically polarized efflux mechanism (FIG. 1, pathway B') are similar to those employed in the Caco-2 cell culture experiments described above.

Calculation of Permeability Coefficients

The approach used to calculate the $P_{monolayer}$ values from the experimental data generated in the BMEC culture model is identical to the approach used to calculate the $P_{monolayer}$ values in Caco-2 cell culture experiments above.

In Situ Rat Brain Perfusion Studies Perfused Rat Brain Model

The in situ rat brain perfusion technique employed is identical to that described by Takasato et al. (1984). The right pterygopalatine, occipital, and superior thyroid arteries of male Sprague-Dawley rats (300–400 g) are cauterized and cut, and the right common carotid artery is prepared for ligation by loosely encircling the artery with surgical silk just proximal to the bifurcation of the external carotid artery. A catheter filled with heparinized saline is then placed in the right external carotid artery for retrograde perfusion. The rectal temperature of the animal is maintained at 36.5±0.5° C. throughout the experiment by a heat lamp connected to a feedback device (see Chikhale et al., 1994).

Perfused Rat Brain Transport Studies

In a typical transport experiment (Chikhale et al., 1994), the right hemisphere of the rat brain is perfused at a flow rate of 4.5 ml/min via a syringe connected to a catheter in the right external carotid artery and an infusion pump. The perfusate consists of pH 7.4 bicarbonate-buffered physiologic saline (NaCl, NaHCO$_3$, KCl, NaH$_2$PO$_4$, CaCl$_2$, MgCl$_2$ and glucose) containing [$^3$H]-labeled methoxy inulin as a vascular marker and the peptide or the cyclic prodrug in a ratio between 3:1 and 10:1. After 60 to 240 sec, the perfusion is terminated by decapitation of the animal. The rat brain is removed from the skull and dissected on ice following the procedure of Ohno et al. (1978). Brain tissue samples from the right cerebral hemisphere are weighed and digested overnight at 50° C. in 1 ml of water containing 10% piperidine. After overnight digestion, one aliquot is counted for radioactivity to determine the levels of [$^3$H]-labeled methoxy inulin. A second aliquot is analyzed for the peptide and/or the cyclic prodrug as described above.

Similar to the studies for the BMEC cell culture system, the pathway of flux (passive vs. passive modified by an apically polarized efflux mechanism) can be elucidated by determining the effect of the solute concentration and the effects of verapamil, a known inhibitor of p-glycoprotein, on the flux of the peptide mimetic.

Calculation of Permeability Coefficients

The transport of the peptide or the cyclic prodrug across the BBB is expressed in terms of three parameters: the unidirectional blood-to-brain transfer constants ($K_{in}$), the cerebrovascular permeability-surface area products (PA), and the cerebrovascular permeability coefficients (P) of the peptides (Smith, 1989; Takasato et al., 1984; Fukio et al., 1991). For details concerning how these parameters are calculated, see Chikhale et al. (1994).

Pharmaceutical Compositions

The cyclic peptides and PNAs of the invention are administered in pharmaceutical preparations and in dosages which are naturally dependent upon the known activity of the linear peptide or PNA. Thus, the cyclic peptides and PNAs are formulated per se in preparations or in the form of a pharmaceutically acceptable salt, particularly as a nontoxic pharmaceutically acceptable acid addition salt or acceptable basic salt. These salts can be prepared from the compounds of the invention according to per se conventional chemical methods.

These compounds or compositions can thus be administered orally, sublingually, topically (e.g., on the skin or in the eyes), by inhalation or by suppository, parenterally (e.g., intramuscularly, intravenously, subcutaneously or intradermally), or by inhalation, and in the form of either solid or liquid dosage including tablets, suspensions, and aerosols, as is discussed in more detail below. The administration can be conducted in single unit dosage form with continuous therapy or in single dose therapy ad libitum. A unit dose is defined as 1 to 3000 mg for a human patient.

Useful pharmaceutical carriers for the preparation of the pharmaceutical compositions hereof can be solids, liquids or mixtures thereof; thus, the compositions can take the form of tablets, pills, capsules, powders, enterically coated or other protected formulations (such as binding on ion exchange resins or other carriers, or packaging in lipid or lipoprotein vesicles or adding additional terminal amino acids), sustained release formulations, erodable formulations, implantable devices or components thereof, microsphere formulations, solutions (e.g., ophthalmic drops), suspensions, elixirs, aerosols, and the like.

Water, saline, aqueous dextrose, and glycols are preferred liquid carriers, particularly (when isotonic) for injectable solutions. The carrier can be selected from various oils including those of petroleum, animal, vegetable or synthetic origin, for example, peanut oil, soybean oil, mineral oil, sesame oil, and the like. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. The compositions may be subjected to conventional pharmaceutical expedients such as sterilization and may contain conventional pharmaceutical additives such as preservatives, stabilizing agents, wetting or emulsifying agents, salts for adjusting osmotic pressure, buffers, and the like. Suitable pharmaceutical carriers and their formulations are described in Martin, "Remington's Pharmaceutical Sciences", 15th Ed.; Mack Publishing Co., Easton (1975); see, e.g., pp. 1405–1412 and pp. 1461–1487. Such compositions will, in general, contain an effective amount of the active compound together with a suitable amount of carrier so as to prepare the proper dosage form for proper administration to the host.

In the practice of the therapeutic methods of the invention, the particular dosage of pharmaceutical composition to be administered to the subject will depend on a variety of considerations including the nature of the disease, the severity thereof, the schedule of administration, the age and physical characteristics of the subject, and so forth. Proper dosages may be established using clinical approaches familiar to the medicinal arts. It is presently believed that dosages in the range of 0.1 to 100 mg of compound per kilogram of subject body weight will be useful, and a range of 1 to 100 mg per kg generally preferred, where administration is by injection or ingestion. Topical dosages may utilize formulations containing generally as low as 0.1 mg of compound per ml of liquid carrier or excipient, with multiple daily applications being appropriate.

The invention being thus described, it will be obvious that the same can be varied in many ways. Such variations are not to be regarded as a departure from the spirit and scope of the invention, and all such modifications as would be obvious to one skilled in the art are intended to be included within the scope of the following claims.

Literature Cited

The following literature references have been cited hereinabove, and are hereby incorporated by reference in their entirety.

Alexander, J., Cargill, R., Michelson, S. R., Schwam, H. (1988) "(Acyloxy)alkyl carbamates as novel bioreversible prodrugs for amines: Increased permeation through biological membranes," J. Med. Chem., 31, 318–322.

Amsberry, K. L. and Borchardt, R. T. (1990) "The lactonization of 2'-hydroxyhydrocinnamic acid amides. A potential prodrug for amines," J. Org. Chem., 55, 5867–5877.

Amsberry, K. L. and Borchardt, R. T. (1991) "Amine prodrugs which utilize hydroxy amide lactonization. I. A potential redox-sensitive amide prodrug," Pharm. Res., 8, 323–330.

Amsberry, K. L., Gerstenberger, A. E. and Borchardt, R. T. (1991) "Amine prodrugs which utilize hydroxy amide lactonization. II. A potential esterase-sensitive amide prodrug," Pharm. Res., 8, 455–461.

Atherton, E. and Sheppard, R. C. (1989) Solid Phase Peptide Synthesis: A Practical Approach, IRL Press, New York.

Atherton, E., Bury, C., Sheppard, R. C. and Williams, B. J. (1979), "Stability of fluorenylmethoxycarbonylamino groups in peptide synthesis. Cleavage by hydrogenation and by dipolar aprotic solvents", Tetrahedron Lett., 3041–3042.

Artursson, P. (1990) "Epithelial transport of drugs in cell culture I: A model for studying the passive diffusion of drugs over intestinal absorptive (Caco-2) cells," J. Pharm. Sci., 79, 476–482.

Audus, K. and Borchardt, R. T. (1986a) "Characterization of an in vitro blood brain barrier model system for studying drug transport and metabolism," Pharm. Res., 3, 81–87.

Audus, K. L. and Borchardt, R. T. (1986b) "Characteristics of the large neutral amino acid transport system of bovine brain microvessel endothelial cell monolayers," J. Neurochem., 47, 484–488.

Audus, K. L., Barrel, R. L., Hidalgo, I. J. and Borchardt, R. T. (1990) "The use of cultured epithelial and endothelial cells for drug transport and metabolism studies," Pharm. Res., 7, 435–451 and references contained therein.

Audus, K. L., Chikhale, P. J., Miller, D. W., Thompson, S. E. and Borchardt, R. T. (1992), "Brain uptake: influence of chemical and biological factors," Adv. Drug Res., 23, 1–64 and references contained therein.

Bai, J. P. F. and Amidon, G. L. (1992) "Structural specificity of mucosal-cell transport and metabolism of peptide drugs: Implications for oral peptide drug delivery," Pharm. Res., 9, 969–978 and references contained therein.

Baranczyk-Kuzma, A., Audus, K. L. and Borchardt, R. T. (1986) "Catecholamine-metabolizing enzymes of bovine brain microvessel endothelial cell monolayers," J. Neurochem., 46, 1956–1960.

Baranczyk-Kuzma, A., Audus, K. L. and Borchardt, R. T. (1989) "Substrate specificity of phenol sulfotransferase from primary cultures of bovine brain microvessel endothelium," Neurochem. Res., 14, 689–691.

Baranczyk-Kuzma, A., Garren, J. A., Hidalgo, I. J. and Borchardt, R. T. (1991) "Substrate specificity and some properties of phenol sulfotransferase from human intestinal Caco-2 cells," Life Sci., 49, 1197–1206.

Bedded, C. R., Clark, R. B., Hardy, G. W., Lowe, L. A., Ubatuba, F. B., Vane, J. R., Wilkinson, S., Chang, K. J., Cuatrecasas, P. and Miller, R. J. (1977) "Structural requirements for opioid activity of analogs of the enkephalins," Proc. R. Soc. London Ser. B, 198, 49–265.

Benarab, A., Boye, S., Savelon, L., Guillaumet, G. (1993) "Cyanomethyl group—A versatile protecting group for phenols, primary and secondary amines, and carbamates," Tetrahedron Lett., 34, 7567–7568.

Borchardt, R. T., Hidalgo, I. J., Hillgren, K. M. and Hu, M. (1991) "Pharmaceutical applications of cell culture—an overview," in Pharmaceutical Applications of Cell and Tissue Culture to Drug Transport (G. Wilson, S. S. Davis and L. Illum, Eds.), Plenum, New York, pp. 1–14.

Bundgaard, H. (1985) Design of Prodrugs, Elsevier, Amsterdam.

Burton, P. S., Conradi, R. A. and Hilgers, R. A. (1991) "Mechanism of peptide and protein absorption. 2. Transcellular mechanism of peptide and protein absorption: passive aspects," Adv. Drug Deliv. Res., 4, 171–207 and references contained therein.

Burton, P. S., Conradi, R. A., Hilgers, R. A., Ho, N. F. H. and Maggiora, L. L. (1992) "The relationship between peptide structure and transport across epithelial cell monolayers," J. Control. Release, 9, 87–98.

Burton, P. S., Conradi, R. A., Hilgers, R. A. and Ho, N. F. H. (1993) "Evidence for a polarized efflux system for peptides in the apical membrane of Caco-2 cells," Biochem. Biophys. Res. Commun., 190, 760–766.

Buttleworth, K. R. and Pelley, O. (1973) "Mesenteric venous blood sampling in vivo in the rat," J. Physiol., 232, 60P–61P.

Castro, B., Domoy, J. R., Evin, G. and Selve, C. (1975) "Peptide coupling reagents. IV. N-[oxytris (dimethylamino)phosphonium]benzotriazole hexafluorophosphate," Tetrahedron Lett., 14, 1219–1222.

Chastain, J. E. and Borchardt, R. T. (1989) "L-α-methyldopa transport across bovine brain microvessel endothelial cell monolayers, a model of the blood brain barrier," Neurosci. Res. Commun., 4, 147–152.

Chastain, J. E. and Borchardt, R. T. (1990) "Acivicin transport across bovine brain microvessel endothelial cell monolayers, a model of the blood brain barrier," Neurosci. Res. Commun., 6, 51–55.

Chikhale, E. G., Ng, K. Y., Burton, P. S. and Borchardt, R. T. (1994) "Hydrogen bonding potential as a determinant of the in vitro and in situ blood brain barrier permeability of peptides," Pharm. Res., in press.

Chikhale, P. J. and Borchardt, R. T. (1994) "Metabolism of a-methyldopa in cultured intestinal epithelial (Caco-2) cells: Correlation with metabolism in vivo," Drug Metab. Dispos., submitted.

Collington, G. K., Hunter, J., Allen, C. N., Simmons, N. L. and Hirst, B. H. (1992) "Polarized efflux of 2',7'-bis(2-carboxyethyl)-5(6)-carboxy fluorescein from cultured epithelial cell monolayers," Biochem. Pharmacol., 44, 417–424.

Conradi, R. A., Hilgers, A. R., Ho, N. F. H. and Burton, P. S. (1991) "The influence of peptide structure on transport across Caco-2 cells." *Pharm. Res.*, 8, 1453–1460.

Conradi, R. A., Hilgers, R. A., Ho, N. F. H. and Burton, P. S. (1992) "The influence of peptide structure on transport across Caco-2 cells. II. Peptide bond modification which results in improved permeability." *Pharm. Res.*, 9, 435–439.

Cordon-Cardo, C., O'Brien, J. P., Casals, D., Rittman-Grauer, L., Bielder, J. L., Melamed, M. R. and Bertino, J. R., (1989) "Multidrug-resistance gene (P-glycoprotein) is expressed by endothelial cells at blood-brain barrier sites." *Proc. Natl. Acad. Sci.*, 86, 695–698.

Crine, P., Le Grimellec, C., Lemieux, E., Labont__, L., Fortin, S., Blachier, A. and Aubry, M. (1985) "The production and characterization of a monoclonal antibody specific for the 94,000 dalton enkephalin-degrading peptidase from rabbit kidney brush border." *Biochem. Biophys. Res. Commun.*, 131, 255–261.

Dave, K. J., Stobaugh, J. F. and Riley, C. M. (1992a), "Reversed phase liquid chromatography of the opioid peptides. 2. Quantitative structure retention relationships and isocratic retention prediction." *J. Pharm. Biomed. Anal.*, 10, 49–60.

Dave, K. J., Stobaugh, J. F., Rossi, T. M. and Riley, C. M. (1992b), "Reversed phase liquid chromatography of the opioid peptides. 3. Development of a microanalytical system for opioid peptides involving microbore liquid chromatography, postcolumn derivatization and laser-induced fluorescence detection." *J. Pharm. Biomed. Anal.*, 10, 965–977.

de Montigny, P., Stobaugh, J. F., Givens, R. S., Carlson, R. G., Srinivasachar, K., Sternson, L. A. and Higuchi, T. (1987) "Naphthalene-2,3-dicarboxaldehyde/cyanide ion: a rationally designed fluorogenic reagent for primary amines." *Anal. Chem.*, 59, 1096–1101.

de Montigny, P., Riley, C. M., Sternson, L. A. and Stobaugh, J. F. (1990) "Fluorogenic derivatization of peptides with naphthalene-2,3-dicarboxaldehyde/cyanide: Optimization of yield and application in the determination of leucine-enkephalin-spiked human plasma samples." *J. Pharm. Biomed. Anal.*, 8, 419–429.

Diago-Meseguer, J., Palomo-Coll, A. L., Fernandez-Lizarbe, J. R. and Zugaza-Bilbao-A. (1980) "A new reagent for activating carboxyl groups: Preparation and reactions of N,N-bis[2-oxo-3-oxazolidinyl] phosphorodiamidic chloride." *Synthesis*, 547–551.

Dion, N., Moual, H. L., Crine, P. and Boileau, G. (1993) "Kinetic evidence that His 711 of neutral endopeptidase 24.11 is involved in stabilization of the transition state." *FEBS*, 318, 301–304.

Doherty, A. M. (1992) *J. Med. Chem.*, 35, 1493.

Ehrenpreis, S. and Sicuteri, F. (1983) *Degradation of endogenous opioids*, Raven Press, New York.

Erspamer, V., Melchiorri, P., Falconieri-Erspamer, G., Negri, L., Corsi, R., Severini, C., Barra, D., Simmaco, M. and Kreil, G. (1989) "Deltorphins: A family of naturally occurring peptides with high affinity and selectivity of d opioid binding sites." *Proc. Natl. Acad. Sci. USA*, 86, 5188–5192.

Feherentz, J. A. and Castro, B. (1983) "An efficient synthesis of optically active A-(t-butoxycarbonylamino)-aldehyde from A-amino acids." *Synthesis*, 676–678.

Flam, F. (1993) "Can DNA Mimics Improve on the Real Thing." *Science*, 261, 1647–1649.

Fukiu, S., Schwares, R., Rapoport, S. I., Takada, Y. and Smith, G. R. (1991) "Blood brain barrier transport of kynurenines: Implications for brain synthesis and metabolism." *J. Neurochem.*, 56, 2007–2017.

Gacel, G., Dauge, V., Breuz__, P., Delay-Goyet, P. and Roques, B. P. (1988) "Development of conformationally constrained linear peptides exhibiting a high affinity and pronounced selectivity for d opioid receptors." *J. Med. Chem.*, 31, 1891–1897.

Gogate, U., Repta, A. J., Alexander, J. (1987) "N-(Acyloxyalkoxy carbonyl) derivatives as potential prodrugs of amines. I. Kinetics and mechanism of degradation in aqueous solutions." *Int. J. Pharmaceutics*, 40, 235–248.

Gray, R., Vander Velde, D., Burke, C. J., Manning, M., Middaugh, C. R. and Borchardt, R. T. (1994) "Delta sleep-inducing peptide: Solution conformational studies of a membrane-permeable peptide" *Biochemistry*, 33, 1323–1331.

Greenlee, W. J., (1990) *Med. Res. Rev.*, 10, 173.

Griffiths, N. M., Hirst, B. H. and Simmons, N. L. (1993) "Active secretion of the fluoroquinoline ciprofloxacin by human intestinal epithelial Caco-2 cell layers." *Br. J. Pharmacol.*, 108, 575–576.

Harney, J., Peffer, N. J. K., Bisi, J. E., Thompson, S. A., Josey, J. A., Ricca, D. J., Hassman, C. F., Bonham, M. A., Au, K. G., Carter, S. G., Bruckenstein, D. A., Boyd, A. L., Nobel, S., and Babiss, L. E., (1992) "Antisense and Antigene Properties of Peptide Nucleic Acids," *Science*, 258, 1481.

Hegmann, E. J., Bauer, H. C. and Kerbel, R. S. (1992) "Expression and functional activity of P-glycoprotein in cultured cerebral capillary endothelial cells." *Cancer Res.*, 52, 6969–6975.

Hidalgo, I. J., Raub, T. J. and Borchardt, R. T. (1989) "Biochemical, histological and physicochemical characterization of human adenocarcinoma cells (Caco-2) as a model system for studying mucosal transport and metabolism of drugs." *Gastroenterology*, 96, 736–749.

Hidalgo, I. J. and Borchardt, R. T. (1990a), "Transport of a large neutral amino acid (phenylalanine) in a human intestinal epithelial cell line: Caco-2." *Biochim. Biophys. Acta*, 1028, 25–30.

Hidalgo, I. J. and Borchardt, R. T. (1990b) "Transport of a bile acid in a human intestinal epithelial cell line: Caco-2." *Biochim. Biophys. Acta*, 1035, 97–103.

Hilgers, A. R., Conradi, R. A. and Burton, P. S. (1990) "Caco-2 cell monolayers as a model for drug transport across the intestinal mucosa." *Pharm. Res.*, 7, 902–910.

Ho, N. F., Raub, T. R., Burton, P. S., Barsuhn, C. L., Adson, A., Audus, K. L. and Borchardt, R. T. (1993) "Quantitative approaches to delineate transport mechanisms in cell culture monolayers." in *Transport Processes in Pharmacuetical Systems* (K. J. Himmelstein, G. L. Amidon and P. I. Lee, Eds.), Marcel Dekker, New York, in press.

Horan, P., Wild, K. D., Kazmierski, W. M., Ferguson, R., Hruby, V. J., Weber, S. J., Davis, T. P., Fang, L., Knapp, R. J., Yamamura, H. I., Kramer, T. H., Burks, T. F., Bowen, W. D., Takemori, A. E. and Porreca, F. (1993) "Unexpected antinociceptive potency of cyclic [D-Tca$^1$] CTAP: Potential for a novel mechanism of action, *Eur. J. Pharmacol.* 233: 53–62, 1993.

Howell, S., Kenny, A. J. and Turner, A. J. (1992) "A survey of membrane peptidases in two human colonic cell lines, Caco-2 and HT-29." *Biochem J.*, 284, 595–601.

Hruby, V. J. and Gehrig, C. A. (1989) "Recent developments in the design of receptor specific opioid peptides." *Med. Res. Rev.*, 9, 343–401. Hsing, S., Gatmaitan, Z. and Arias, I. M. (1992) "The function of Gp-170, the multidrug-resistance gene product, in the brush border of rat intestinal mucosa," *Gastroenterology.*, 102, 8789–885.

Huff, J. R. (1991) "HIV Protease: A Novel Chemotherapeutic Target for AIDS" *J. Med. Chem.*, 34, 2305.

Hughes, J., Smith, T. W., Kosterlitz, H. W., Fothergill, L. A., Morgan, B. A. and Morris, H. R. (1975) "Identification of two related pentapeptides from the brain with potent opiate agonist activity," *Nature*, 258, 577–579.

Hu, M. and Borchardt, R. T. (1990) "Mechanism of L-α-methyldopa transport through a monolayer of polarized human intestinal epithelial cells (Caco-2)," *Pharm. Res.*, 1313–1319.

Hu, M. and Borchardt, R. T. (1992) "Transport of a large neutral amino acid in a human intestinal epithelial cell line (Caco-2)," *Biochim. Biophys. Acta.*, 1135, 233–244.

Humphrey, M. J. and Ringrose, P. S., (1986) *Drug Metab. Rev.*, 17, 383.

Hunter, J., Hirst, B. H. and Simmons, N. L. (1993) "Drug absorption limited by P-glycoprotein-mediated secretory drug transport in human intestinal epithelial Caco-2 cell layers," *Pharm. Res.*, 10, 743–749.

Islam, I., Ng, K. Y., Chang, K. T., McQuade, T. J., Hui, J. O., Wilkinson, K. F., Rush, B. D., Ruwart, M. J., Borchardt, R. T. and Fisher, J. F. (1994) "Evaluation of a vitamin clocking strategy for improving the availability of oligopeptide therapeutics: biotinylated HIV protease inhibitors," *J. Med. Chem.*, in press.

Jouin, P., Castro, B., Zeggaf, C., Pantaloni, A., Senet, J. P., Lecolier, S. and Sennyey, G. (1987). "Convenient one-pot esterification of N-protected amino acids via isopropenyl chloroformate activation" *Tetrahedron Lett.*, 28, 1661–1664.

Kai, M., Ishida, J. and Ohkura, Y. (1988) "High performance liquid chromatographic determination of leucine-enkephaline-like peptide in rat brain by precolumn fluorescence derivatization involving formylation followed by reaction with 1,2-diamino-4,5-dimethoxybenzene," *J. Chromarogr.*, 430, 271–278.

Kato, A., Hidalgo, I. J. and Borchardt, R. T. (1989) "Epidermal growth factor (EGF) binding in a human colon carcinoma cell line (Caco-2)," *Biochem. Biophys. Res. Commun.*, 158, 317–324.

Kamijo, T., Harada, H. and Iizuka, K. (1984) "An improved and convenient synthesis of esters using 1,1'-carbonyldiimidazole and a reactive halide," *Chem. Pharm. Bull.*, 32, 5044–5047.

Kendall, P. M., Johnson, J. V. and Cook, C. E. (1979) "Synthetic route to an aromatic analog of strigol," *J. Org. Chem.*, 44, 1421–1424.

Kenny, J. (1983) "Cell surface peptidases are neither peptide- nor organ-specific," *Trends Biochem. Sci.*, 11, 40–42.

Kim, D. C., Burton, P. S. and Borchardt, R. T. (1993a) "A correlation between the permeability characteristics of a series of peptides using an in vitro cell culture model (Caco-2) and an in situ perfused rat ileum model of the intestinal mucosa," *Pharm. Res.*, 10, 1710–1714.

Kim, D. C., Harrison, A. W., Ruwart, M. J., Wilkinson, K. F., Fisher, J. F., Hidalgo, I. J. and Borchardt, R. T. (1993b) "Evaluation of the bile acid transporter for the enhancement of renin-inhibitory peptide intestinal permeability," *J. Drug Targeting*, 1, 347–359.

Kramer, W., Girbig, F., Gutjahr, U., Kleemann, H. -W., Leipe, I., Urbach, H. and Wagner, A. (1990) "Interactions of renin inhibitors with intestinal uptake system for oligopeptides and β-lactam antibiotics," *Biochim. Biophys. Acta*, 1027, 25–30.

Kreil, G., Barra, D., Simmaco, M., Erspamer, V., Falconieri-Erspamer, G., Negri, L., Severini, C., Corsi, R., and Melchiorri, P. (1989) "Deltorphins, a novel amphibian skin peptide with high selectivity and affinity for d opioid receptors," *Eur. J. Pharmacol.*, 162, 123–128.

Kristjansson, F., Thakur, A. and Stobaugh, J. F. (1992) "Selective fluorogenic derivatization of pro$^2$-lys-peptides with naphthalene-2,3-dicarboxaldehyde/cyanide, "*Anal. Chim. Acta.*, 262, 209–215.

Lee, V. H. L. and Yamamoto, A., (1990) *Adv. Drug. Deliv. Res.*, 4, 171.

Lee, V. H. L., (1991) *Peptide and Protein Delivery*, Marcel Dekker, New York.

Lowry, O. H., Rosebrough, N. J., Farr, A. L. and Randall, R. J. (1951) "Protein measurement with the folin phenol reagent," *J. Biol. Chem.*, 193, 265–275.

Madara, J. L. and Trier, J. S. (1987) "Functional morphology of the mucosa of the small intestine," in *Physiology of the Gastrointestinal Tract*, Vol. 2 (L. R. Johnson, Ed.) Raven Press, New York, 2nd ed., pp. 1209–1249.

Matsunaga, T. O., Collins, N., Ramaswami, V., Yamamura, S. H., O'Brien, D. F. and Hruby, V. J. (1993) "Comparison of the membrane-bound states of two structurally similar d-selective opioid peptides by transferred nuclear overhauser effect spectroscopy and molecular modeling," *Biochemistry*, 32, 13180–13189.

Matthews, D. M. (1975) "Intestinal absorption of peptides," *Physiol. Rev.*, 55, 537–608.

Mergler, M, Tanner, R., Gosteli, J. and Grogg, P. (1988) "Peptide synthesis by a combination of solid-phase and solution methods. 1 A new very acid-labile anchor group for the solid phase synthesis of fully protected fragments," *Tetrahedron Lett.*, 29, 4005–4009.

Metzer, M., Heuber-Metzer, S., Steinacher, A. and Struber, J. (1980) "Staining $PO_2$ measurements in the rat brain and quantitative morphometry of the surrounding capillaries," *Pflugers Arch.*, 388, 21–27.

Mifune, M., Krehbiel, D. K., Stobaugh, J. F. and Riley, C. M. (1989) "Multidimensional high performance liquid chromatography of opioid peptides following precolumn derivatization with naphthalene-2,3-dicarboxaldehyde in the presence of cyanide ion: Preliminary results on the determination of leucine- and methionine-enkephalin-like fluorescence in the striatum region of the rat brain," *J. Chromatogr.*, 496, 55–70.

Miller, D. W., Audus, K. L. and Borchardt, R. T. (1992) "Cultured bovine brain microvessel endothelial cells: A model of the blood brain barrier," *J. Tiss. Cult. Meth.*, 14, 217–224.

Miller, D. W., Kato, A., Ng, L., Chikhale, E. and Borchardt, R. T. (1994a) "Cell culture models for examining peptide absorption," in *Peptide-based Drug Design: Controlling Transport and Metabolism* (M. D. Taylor and G. Amidon, Eds.), American Chemical Society, Washington D.C., in press, and references contained therein.

Miller, D., Keller, B. T. and Borchardt, R. T. (1994b) "Identification and distribution of insulin receptors in cultured bovine brain microvessel endothelial cells: Possible function in insulin processing in the blood brain barrier," *J. Cellular Physiol.*, in press.

Morgan, B. A. and Gainor, J. A., (1989) *Ann. Rep. Med. Chem.*, 24, 243.

Nellins, H. (1991), "Paracellular intestinal transport: modulation of absorption," *Adv. Drug Deliv. Res.*, 7, 339–364 and references contained therein.

Ng, K. Y. and Borchardt, R. T. (1993) "Biotin transport in a human intestinal epithelial cell line (Caco-2)," *Life Sci.*, 53, 1121–1127.

Ng, K. Y., Miller, D. W., Kato, A., Pachter, and Borchardt, R. T. (1994) "Improved methodology for the isolation and culturing of bovine brain microvessel endothelial cells," *In Vitro Cell Dev. Biol.*, submitted.

Nonomura, M., Fukuta, M., Takakura, Y. T., Miller, D. and Borchardt, R. T. (1994) "Natriuretic peptide receptors on cultured bovine brain microvessel endothelial cells. Receptor identification and distribution," *Biochim. Biophys. Acta.*, submitted.

Ohno, K., Pettigrew, K. D. and Rapoport, S. I. (1978) "Lower limits of cerebrovascular permeability to nonelectrolytes in the conscious rat," *Am. J. Physiol.*, 235, H299-H307.

Oliyai, R. and Stella, V. J. (1993) "Prodrugs of peptides and proteins for improved formulation and delivery," *Annu. Rev. Pharmacol. Toxicol.*, 32, 521–544, and references cited therein.

Ono, M. and Itoh, I. (1988), "A new deprotection method for levulinyl protecting groups under neutral conditions", *Chem. Lettt.*, 585–558.

Plattner, J. J. and Norbeck, D. J. (1990) in *Drug Discovery Technologies* (C. R. Clark and D. H. Moos, Eds.), Wiley, New York, pp. 92–126.

Rabel, S. R., Stobaugh, J. F., Heinig, R. and Bostick, J. M. (1993a) "Improvements in detection sensitivity for the determination of ivermectin in plasma using chromatographic techniques and laser-induced fluorescence detection with automated derivatization," *J. Chromatogr.*, 617, 79–86.

Rabel, S. R., Trueworthy, R. and Stobaugh, J. F. (1993b) "Recent developments utilizing capillary electrophoresis with laser-induced fluorescence for the determination of 6-mercaptopurine metabolites," *J. High Res. Chromatogr.*, 16, 326–328.

Raeissi, S. and Audus, K. L. (1989) "Permeability of delta sleep-inducng peptide through monolayers of bovine brain microvessle endothelial cells," *J. Pharm. Pharmacol.*, 41, 848–852.

Raeissi, S. and Borchardt, R. T. (1993) "Cultured human adenocarcinoma cells (Caco-2) as a model to study the mechanism by which adjuvants enhance intestinal permeability of drugs," *S.T.P. Pharma Sci.*, 3, 56–62.

Ramaswami, V., Haaseth, R., Matsunaga, T. O., Hruby, V. J. and O'Brien, D. J. (1992) "Opioid peptide interactions with lipid bilayer membranes," *Biochim. Biophys. Acta*, 1109, 195–202.

Ronald, R. C., Lansinger, J. M., Lillie, T. S. and Wheeler, C. J. (1982) "Total synthesis of frustulosium and aurocitria," *J. Org. Chem.*, 47, 2541–2549.

Rosenfeld, R. G., Pham, H., Keller, B., Borchardt, R. T. and Pardridge, W. M. (1987) "Structural comparison of receptors for insulin, insulin-like growth factor I and II (IGF-I and IGF-II) in brain and blood brain barrier," *Biochem. Biophys. Res. Commun.*, 149, 159–166.

Rubas, W., Jezyk, N. and Grass, G. M. (1993) "Comparison of the permeability characteristics of a human colonic epithelial (Caco-2) cell line to colon of rabbit, monkey and dog intestine and human drug absorption," *Pharm. Res.*, 10, 113–118.

Saha, A. K., Schultz, P. and Rapoport, H. (1989) "1,1'-Carbonylbis(3-methylimidazolium) triflate: An efficient reagent for aminoacylations," *J. Am. Chem. Soc.*, 111, 4856–4859.

Sasaki, Y and Coy, D. H. (1987) "Solid phase synthesis of peptides containing the $CH_2NH$ peptide bond isostere," *Peptides*, 8, 119–121.

Sasaki, Y., Matsui, M., Fujita, H., Hosono, M., Taguchi, M., Suzuki, K., Sakurada, S., Sato, T., Sakurada, T. and Kisara, K. (1985) "The analgesic activity of D-$Arg^2$-dermorphin and its N-terminal tetrapeptide analogs after subcutaneous administration in mice," *Neuropeptides*, 5, 391–394.

Schiller, P. W. (1991) "Development of receptor-specific opioid peptide analogues," *Prog. Med. Chem.*, 28, 301–340.

Schiller, P. W. (1993) "Development of receptor-selective opioid peptide analogs as pharmacologic tools and as potential drugs," *Handbook Exp. Pharmacol.*, 104, 681–710.

Schiller, P. W., Nguyen, T. M. -D., Maziak, L. and Lemieux, C. (1985) "A novel cyclic opioid peptide analog showing high preference for μ receptors," *Biochem. Biophys. Res. Comm.*, 127, 558–564.

Schiller, P. W., Weltrowska, G., Nguyen, T. M., Wilkes, B. C., Chung, N. G. and Lemieux, C. (1993) "TIPP[ψ]: A highly potent and stable pseudopeptide δ opioid receptor antagonist with extraordinary d selectivity," *J. Med. Chem.*, 36, 3182–3187.

Scriba, G. K. E. and Borchardt, R. T. (1989a) "Metabolism of 1-methyl-4-phenyl-1,2,3,6-tetrahydropyridine (MPTP) by bovine brain capillary endothelial cell monolayers," *Brain Res.*, 501, 175–178.

Scriba, G. K. E. and Borchardt, R. T. (1989b) "Metabolism of catecholamine esters by cultured bovine brain microvessel endothelial cells," *J. Neurochem.*, 53, 610–615.

Shah, M. V., Audus, K. L. and Borchardt, R. T. (1989) "The application of bovine brain microvessel endothelial cell monolayers grown onto polycarbonate membranes in vitro to estimate the potential permeability of solutes through the blood brain barrier," *Pharm. Res.*, 6, 623–627.

Smith, Q. R. (1989) "Quantitation of blood-brain barrier permeability," in *Implications of the Blood-Brain Barrier and its Manipulation*, Vol. 1 (E. A. Neuwelt, Ed.) Plenum, New York, pp. 85–118.

Smith, K. R. and Borchardt, R. T. (1989) "Permeability and mechanism of albumin, cationized albumin and glycosylated albumin transcellular transport across monolayers of cultured brain capillary endothelial cells," *Pharm. Res.*, 6, 466–473.

Smith, K. R., Kato, A. and Borchardt, R. T. (1988) "Characterization of specific receptors for atrial natriuretic factor on cultured bovine brain capillary endothelial cells," *Biochem. Biophys. Res. Commun.*, 157, 308–314.

Stevenson, C. L., Donlan, M. E., Friedman, A. R. and Borchardt, R. T. (1993a) "Solution conformation of $Leu^{27}$ hGFG(1–32)$NH_2$ and its deamidation products by 2D-NMR," *Int. J. Peptide Protein Res.*, 42, 24–32.

Stevenson, C. L., Friedman, A. R., Kubiak, T. M., Donlan, M. and Borchardt, R. T. (1993b) "Effect of secondary structure on the role of deamidation of several growth hormone-releasing factor analogs," *Int. J. Peptide Protein Res.*, 42, 497–503.

Stewart, J. M. and Young, J. D. (1984) *Solid Phase Peptide Synthesis*, Pierce Chemical Company, Rockford, Ill.

Takakura, Y., Kuentzel, S. L., Raub, T., Davies, A., Baldwin, S. A. and Borchardt, R. T. (1991a) "Hexose uptake in primary cultures of bovine brain microvessel endothelial cells. I. Basic characteristics and effects of D-glucose and insulin," *Biochim. Biophys. Acta.*, 1070, 1–10.

Takakura, Y., Kuentzel, S. L., Raub, T., Davies, A., Baldwin, S. A. and Borchardt, R. T. (1991b) "Hexose uptake in primary cultures of bovine brain microvessel endothelial cells. II. Effect of conditioned media from astroglial and glioma cells," *Biochim. Biophys. Acta.*, 1070, 11–19.

Takakura, Y., Audus, K. L. and Borchardt, R. T. (1992) "Blood-brain barrier: transport studies in isolated capillaries and in cultured brain endothelial cells," *Adv. Pharmacol.*, 22, 137–165 and references contained therein.

Takasato, Y., Rapoport, S. I. and Smith, Q. R. (1984) "An in situ brain perfusion technique to study cerebrovascular transport in the rat," *Am. J. Physiol.*, 247, 11484–11493.

Tang, A. S., Chikhale, P. J., Shah, P. K. and Borchardt, R. T. (1993) "Utilization of a human intestinal epithelial cell culture system (Caco-2) for evaluating cytoprotective agents," *Pharm. Res.*, 10, 1620–1626.

Tidd, D. M. (1990) "A Potential Role for Antisense Oligonucleotide Analogs in the Development of Oncogene Targeted Cancer-Chemotherapy," *Anti-Cancer Research* 1647.

Tsuji, A., Terasabi, T., Takabatake, Y., Tenda, Y., Tamai, I., Yamashima, T., Moritani, S., Tsuruo, T. and Yamashita, J. (1992) "P-glycoprotein as the drug efflux pump in primary cultured bovine brain capillary endothelial cells," *Life Sci.*, 51, 1427–1437.

Tung, R. D. and Rich, D. H. (1985) "Bis(2-oxo-3-oxazolidinyl) phosphinic chloride (1) as a coupling reagent for N-alkyl amino acids," *J. Am. Chem. Soc.*, 107, 4342–4343.

Ueda, Y., Mikkilineni, A. B., Knipe, J. O., Rose, W. C., Casazza, A. M. and Vyas, D. M. (1993) "Novel water soluble phosphate prodrugs of Taxol® possessing in vivo antitumor activity," *Bioorg. Med. Chem. Lett.*, 3, 1761–1766.

Van Bree, J. V. M. M., Audus, K. L. and Borchardt, R. T. (1988) "Carrier-mediated transport of baclofen across monolayers of bovine brain endothelial cells in primary culture," *Pharm. Res.*, 5, 369–371.

Vanderah, T. W., Wild, K. D., Takemori, A. E., Sultana, M., Portoghese, P. S., Bowen, W. D., Mosberg, H. I. and Porreca, F. (1992) "Mediation of swim-stress antinociception by the opioid delta2 receptor in the mouse," *J. Pharmacol. Exp. Ther.*, 262, 190–197.

Vander Velde, D. G., Georg, G. I., Grunewald, G. L., Gunn, C. W. and Mitscher, L. A. (1993) "Hydrophobic collapse of taxol and taxotere solution conformations in mixtures of water and organic solvents," *J. Amer. Chem. Soc.*, 115, 11650–11651.

Wilson, G., Hassam, J. F., Dix, C. J., Williamson, I., Shah, R., Mackay, M. and Artursson, P. (1990), "Transport and permeability properties of human Caco-2 cells: An in vitro model of the intestinal epithelial cell barrier," *J. Control. Release*, 11, 25–40.

Wang, B. and Borchardt, R. T. (1993) "The development of a novel redox sensitive protecting group for amines and alcohols" 206th American Chemical Society National Meeting in Chicago, Ill., Aug. 22–27, 1993, Abstract #139 (Organic section) and highlighted in C&EN Sep. 13, 1993 issue, page 41.

Wang, B., Liu, S., Borchardt, R. T., "A novel redox sensitive protecting group for amines which utilizes a facilitated lactonization reaction", *J. Org. Chem.* 1995, 60, 539–543.

Wang, S. S. (1973) "p-Alkoxybenzyl alcohol resin and p-alkoxybenzyloxycarbonylhydrazide resin for solid phase synthesis of protected peptide fragments" *J. Am. Chem. Soc.* 95, 1328–1333.

Wild, R. D., Fong, L., McNutt, R. W., Chang, K. J., Toth, G., Borsodi, A., Yamamura, H. I. and Porreca, F. (1993) "Opioid delta receptor binding of BW 373u86, a nonpeptide delta agonist, is not regulated by guanine nucleotides and sodium, *Eur. J. Pharmacol., Mol. Pharmacol. Sec.*, 246, 289–292.

Wolfe, J. L., Vander Velde, D., and Borchardt, R. T. (1992) *J. Org. Chem.*, 57, 6138.

---

What is claimed is:

1. A cyclic prodrug of a biologically active peptide or peptide nucleic acid, wherein the N-terminal amino group and the C-terminal carboxyl group of said biologically active peptide or peptide nucleic acid are linked via a linker, or wherein the C-terminal carboxyl group of said peptide is linked to a side chain amino group or a side chain hydroxyl group via a linker, or wherein a side chain carboxyl group of said peptide is linked to a side chain amino group or a side chain hydroxyl group via a linker, and wherein said linker is selected from the group consisting of compounds of the formula:

Scheme 4

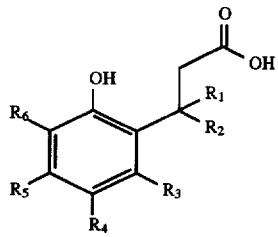
(I)

wherein
$R_1$=CH$_3$, alkyl, phenyl, benzyl, halogen
$R_2$=CH$_3$, alkyl, phenyl, benzyl, halogen
$R_3$=CH$_3$, alkyl, alkenyl, phenyl, benzyl, halogen
$R_4$=OH, H, NO$_2$
$R_5$=H, CH$_3$, alkyl, alkenyl, phenyl, benzyl, halogen
$R_6$=H, CH$_3$, alkyl, alkenyl, phenyl, benzyl, halogen;

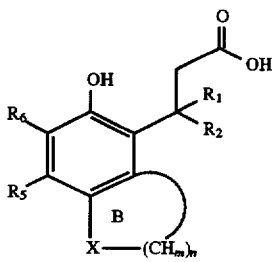
(II)

wherein
$R_1$=CH$_3$, alkyl, alkenyl, phenyl, benzyl, halogen
$R_2$=CH$_3$, alkyl, alkenyl, phenyl, benzyl, halogen
$R_5$=H, CH$_3$, alkyl, alkenyl, phenyl, benzyl, halogen
$R_6$=H, CH$_3$, alkyl, alkenyl, phenyl, benzyl, halogen,
Ring B can be aliphatic or aromatic
n=1,2,3,4 ... 10
m=can be 1 or 2 depending if ring B is aliphatic, has double bond(s) or aromatic
X=O, S, NH, N-alkyl;

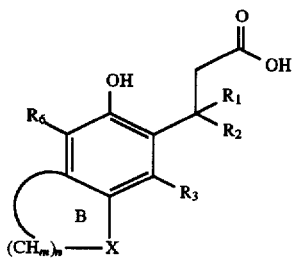
(III)

wherein
$R_1$=CH$_3$, alkyl, alkenyl, phenyl, benzyl, halogen
$R_2$=CH$_3$, alkyl, alkenyl, phenyl, benzyl, halogen
$R_3$=H, CH$_3$, alkyl, alkenyl, phenyl, benzyl, halogen
$R_6$=H, CH$_3$, alkyl, alkenyl, phenyl, benzyl, halogen,
Ring B can be aliphatic or aromatic
n=1,2,3,4 ... 10
m=can be 1 or 2 depending if ring B is aliphatic or contains double bond(s) or aromatic X=O, S, NH, N-alkyl;

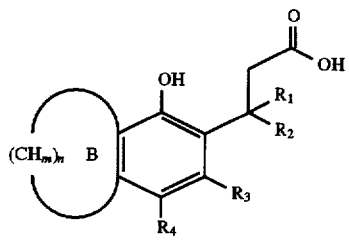
(IV)

wherein
$R_1$=CH$_3$, alkyl, alkenyl, phenyl, benzyl, halogen
$R_2$=CH$_3$, alkyl, alkenyl, phenyl, benzyl, halogen
$R_3$=CH$_3$, alkyl, alkenyl, benzyl, halogen
$R_4$=OH, H, NO$_2$
Ring B can be aliphatic or aromatic
n=1,2,3,4 ... 10
m=can be 1 or 2 depending if ring B is aliphatic or contains double bond(s) or aromatic;

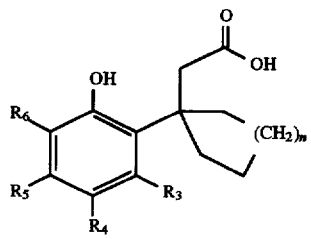
(V)

wherein
$R_3$=CH$_3$, alkyl, alkenyl, phenyl, benzyl, halogen
$R_4$=OH, H, NO$_2$
$R_5$=H, CH$_3$, alkyl, alkenyl, phenyl, benzyl, halogen
$R_6$H, CH$_3$, alkyl, alkenyl, phenyl, benzyl, halogen
n=1,2,3,4 ... 10;

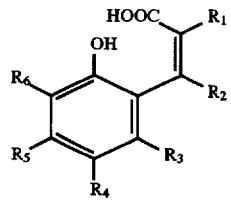
(VI)

wherein
$R_1$=CH$_3$, alkyl, alkenyl, phenyl, benzyl, halogen
$R_2$=CH$_3$, alkyl, alkenyl, phenyl, benzyl, halogen
$R_3$=CH$_3$, alkyl, alkenyl, phenyl, benzyl, halogen
$R_4$=OH, H, NO$_2$
$R_5$=CH$_3$, alkyl, alkenyl, phenyl, benzyl, halogen
$R_6$=H, CH$_3$, alkyl, alkenyl, phenyl, benzyl, halogen;

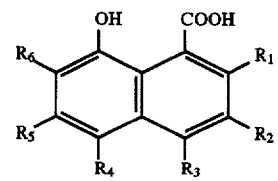
(VII)

wherein
$R_1$=CH$_3$, alkyl, alkenyl, phenyl, benzyl, halogen
$R_2$=CH$_3$, alkyl, alkenyl, phenyl, benzyl, halogen $R_1$=CH$_3$, alkyl, alkenyl, phenyl, benzyl, halogen
$R_4$=OH, H, NO$_2$
$R_5$=CH$_3$, alkyl, alkenyl, phenyl, benzyl, halogen
$R_6$=H, CH$_3$, alkyl, alkenyl, phenyl, benzyl, halogen;

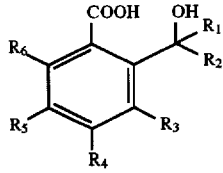
(VIII)

wherein $R_1$=CH$_3$, alkyl, alkenyl, phenyl, benzyl, halogen
$R_2$=CH$_3$, alkyl, alkenyl, phenyl, benzyl, halogen
$R_3$=CH$_3$, alkyl, alkenyl, phenyl, benzyl, halogen
$R_4$=OH, H, NO$_2$
$R_5$=H, CH$_3$, alkyl, phenyl, benzyl, halogen
$R_6$=H, CH$_3$, alkyl, alkenyl, phenyl, benzyl, halogen;

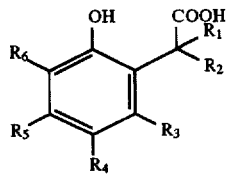
(IX)

wherein $R_1$=CH$_3$, alkyl, alkenyl, phenyl, benzyl, halogen
$R_2$=CH$_3$, alkyl, alkenyl, phenyl, benzyl, halogen
$R_3$=CH$_3$, alkyl, alkenyl, phenyl, benzyl, halogen
$R_4$=OH, H, NO$_2$
$R_5$=H, CH$_3$, alkyl, alkenyl, phenyl, benzyl, halogen
$R_6$H, CH$_3$, alkyl, alkenyl, phenyl, benzyl, halogen;

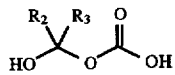
(X)

wherein $R_2$=H, CH$_3$, alkyl, alkenyl, phenyl, benzyl
$R_3$=H, CH$_3$, alkyl, alkenyl, phenyl, benzyl;

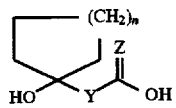
(XI)

wherein
n=0, 1, . . . 15

Y=S, O
Z=S, O; and

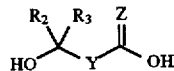
(XII)

wherein $R_2$=H, CH$_3$, alkyl, alkenyl, phenyl, benzyl
$R_3$=H, CH$_3$, alkyl, alkenyl, phenyl, benzyl,
Y=S, O
Z=S, O.

2. The cyclic prodrug of claim 1, wherein said biologically active peptide is a peptide mimetic, a peptide active in the central nervous system, a peptide useful for treating cardiovascular disease, an antimicrobial peptide, a peptide useful in antitumor therapy, or a hormone; and said peptide nucleic acid is an antiviral injection or anticancer agent.

3. The cyclic prodrug of claim 2, wherein said peptide active in the central nervous system is a peptide active for sedating, a peptide having cholecystokinin anti-anxiolytic activity, neurotensin, an opioid receptor-specific peptide, or a badykinin antagonist; said peptide useful for treating cardiovascular disease is an angiotensin converting enzyme inhibitor, a renin modulator, a renin inhibitor, a peptide mimetic renin inhibitor, a vasoactive peptide, or a peptide useful in antithrombic therapy; said antimicrobial peptide is a cecropin, magainin, or gramacidin; said peptide useful in antitumor therapy is a mitogenic growth factor; and said hormone is a growth hormone or an enzyme inhibitor.

4. The cyclic prodrug of claim 3, wherein said peptide active for sedating is Delta Sleep Inducing Peptide;

said vasoactive peptide is endothelin, a tachykinin, atrial natriuretic peptide, a zinc metalloproteinase inhibitor, a calcitonin-related peptide, Neuropeptide Y, vassopressin, or oxytocin; and said peptide useful in antithrombic therapy is an RGD peptide or a thrombin inhibitor.

5. A pharmaceutical composition, comprising an effective amount of said cyclic prodrug of claim 1, and a pharmaceutically acceptable carrier, excipient, or diluent.

* * * * *